United States Patent
Cundiff et al.

(10) Patent No.: US 12,369,922 B2
(45) Date of Patent: Jul. 29, 2025

(54) SURGICAL INSTRUMENTS INCLUDING A SET OF CUTTING BURRS FOR PERFORMING AN OSTEOTOMY

(71) Applicant: Fusion Orthopedics, LLC, Mesa, AZ (US)

(72) Inventors: Adam J. Cundiff, Gilbert, AZ (US); Nathan G. Peterson, Gilbert, AZ (US); Eli W. Jacobson, Chandler, AZ (US)

(73) Assignee: Fusion Orthopedics, LLC

( * ) Notice: Subject to any disclaimer, the term of this patent is extended or adjusted under 35 U.S.C. 154(b) by 461 days.

(21) Appl. No.: 17/832,418

(22) Filed: Jun. 3, 2022

(65) Prior Publication Data

US 2022/0304701 A1    Sep. 29, 2022

Related U.S. Application Data

(63) Continuation-in-part of application No. 16/459,545, filed on Jul. 1, 2019, now Pat. No. 11,376,017, and a
(Continued)

(51) Int. Cl.
*A61B 17/14*         (2006.01)
*A61B 17/15*         (2006.01)
(Continued)

(52) U.S. Cl.
CPC .......... *A61B 17/142* (2016.11); *A61B 17/151* (2013.01); *A61B 17/1659* (2013.01); *A61B 17/1671* (2013.01); *A61B 17/7082* (2013.01); *A61B 17/8095* (2013.01); *A61B 34/20* (2016.02); *A61B 34/30* (2016.02); *A61B 34/32* (2016.02); *G06T 3/02* (2024.01); *G06T 3/147* (2024.01); *G06T 7/30* (2017.01); *G06T 7/33* (2017.01); *A61B 2017/00477* (2013.01); *A61B 17/1617* (2013.01); *A61B 17/1757* (2013.01); *A61B 2034/107* (2016.02); *A61B 2034/2055* (2016.02); *A61B 2034/2057* (2016.02); *A61B 2034/2059* (2016.02); *A61B 2034/2065* (2016.02); *A61B 2034/2068* (2016.02); *A61B 2034/2072* (2016.02); *A61B 90/361* (2016.02); *A61B 2090/363* (2016.02); *A61B 2090/364* (2016.02); *A61B 2090/367* (2016.02); *A61B 2090/373* (2016.02); *A61B 2090/376* (2016.02); *A61B 2090/3762* (2016.02); *A61B 2090/3966* (2016.02); *A61B 2090/3983* (2016.02);
(Continued)

(58) Field of Classification Search
CPC .......................... A61B 17/142; A61B 17/1659
See application file for complete search history.

(56) References Cited

U.S. PATENT DOCUMENTS 4,625,725 A * 12/1986 Davison ............. A61B 17/1659
                                                        407/29.1
4,872,452 A * 10/1989 Alexson ............. A61B 17/1659
                                                        407/29.1
(Continued)

*Primary Examiner* — David W Bates

(57) ABSTRACT

Surgical instruments and methods for performing an osteotomy are disclosed herein. A surgical instrument includes a body with a distal end, a proximal end, a first surface, and a second surface. The surgical instrument can include cutting burrs positioned on the first surface and/or the second surface. The surgical instrument can include cutting burrs positioned on the first surface and cutting blades positioned on the second surface.

18 Claims, 35 Drawing Sheets

Related U.S. Application Data continuation-in-part of application No. 17/538,781, filed on Nov. 30, 2021, now Pat. No. 12,035,927, which is a continuation of application No. 16/537,495, filed on Aug. 9, 2019, now Pat. No. 11,253,273, which is a continuation-in-part of application No. 16/459,555, filed on Jul. 1, 2019, now Pat. No. 11,253,272.

(51) Int. Cl.

| | | |
|---|---|---|
| *A61B 17/16* | (2006.01) | |
| *A61B 17/70* | (2006.01) | |
| *A61B 17/80* | (2006.01) | |
| *A61B 34/20* | (2016.01) | |
| *A61B 34/30* | (2016.01) | |
| *A61B 34/32* | (2016.01) | |
| *G06T 3/02* | (2024.01) | |
| *G06T 3/147* | (2024.01) | |
| *G06T 7/30* | (2017.01) | |
| *G06T 7/33* | (2017.01) | |
| *A61B 17/00* | (2006.01) | |
| *A61B 17/17* | (2006.01) | |
| *A61B 34/10* | (2016.01) | |
| *A61B 90/00* | (2016.01) | |
| *A61F 2/46* | (2006.01) | |

(52) U.S. Cl.
CPC ... *A61F 2/4611* (2013.01); *G06T 2207/10028* (2013.01); *G06T 2207/10081* (2013.01); *G06T 2207/10088* (2013.01); *G06T 2207/20221* (2013.01); *G06T 2207/30101* (2013.01); *G06T 2207/30204* (2013.01)

(56) References Cited

U.S. PATENT DOCUMENTS

| | | | | |
|---|---|---|---|---|
| 4,922,898 A * | 5/1990 | Dunn | ............... | A61F 2/4657 606/85 |
| 4,963,155 A * | 10/1990 | Lazzeri | ............... | A61F 2/3609 606/85 |
| 5,006,121 A * | 4/1991 | Hafeli | ............... | A61B 17/1659 606/85 |
| 5,019,082 A * | 5/1991 | Frey | ............... | A61B 17/1659 606/85 |
| 5,087,261 A | 2/1992 | Ryd | | |
| 5,122,142 A * | 6/1992 | Pascaloff | ............... | A61B 17/142 D24/146 |
| 5,342,365 A * | 8/1994 | Waldman | ............... | A61B 17/1659 407/29.1 |
| D361,029 S * | 8/1995 | Goris | ............... | D24/146 |
| 5,601,556 A * | 2/1997 | Pisharodi | ............... | A61F 2/4611 606/62 |
| 5,665,091 A * | 9/1997 | Noble | ............... | A61B 17/1659 606/85 |
| 5,681,315 A * | 10/1997 | Szabo | ............... | A61B 17/1659 606/85 |
| 5,697,889 A * | 12/1997 | Slotman | ............... | A61B 17/025 600/210 |
| 5,707,374 A * | 1/1998 | Schmidt | ............... | A61B 17/1659 606/85 |
| 6,083,228 A * | 7/2000 | Michelson | ............... | A61B 17/1659 606/79 |
| 6,120,508 A * | 9/2000 | Grunig | ............... | A61B 17/1659 606/85 |
| 6,267,594 B1 * | 7/2001 | Hugo | ............... | A61B 17/1637 433/119 |
| 6,383,188 B2 * | 5/2002 | Kuslich | ............... | A61B 17/1617 606/80 |
| 8,888,784 B1 * | 11/2014 | Murphy | ............... | B26B 3/04 606/171 |
| 8,939,981 B1 * | 1/2015 | Anderson | ............... | A61B 17/14 606/82 |
| 9,241,730 B2 * | 1/2016 | Babaev | ............... | A61B 17/142 |
| 10,159,499 B2 | 12/2018 | Dacosta et al. | | |
| 2002/0019638 A1 * | 2/2002 | Grimard | ............... | B23C 3/18 606/85 |
| 2002/0133185 A1 * | 9/2002 | Danger | ............... | A61B 17/142 606/178 |
| 2002/0133186 A1 * | 9/2002 | Kullmer | ............... | B23D 61/025 606/178 |
| 2003/0032971 A1 * | 2/2003 | Hausmann | ............... | A61B 17/142 606/178 |
| 2003/0045884 A1 * | 3/2003 | Robie | ............... | A61B 17/1671 606/90 |
| 2003/0125739 A1 * | 7/2003 | Bagga | ............... | A61L 27/446 606/907 |
| 2004/0098000 A1 * | 5/2004 | Kleinwaechter | ...... | B23D 61/123 D24/146 |
| 2004/0215197 A1 * | 10/2004 | Smith | ............... | A61B 17/1671 606/79 |
| 2004/0243134 A1 * | 12/2004 | Walker | ............... | A61B 17/1659 606/79 |
| 2006/0129160 A1 * | 6/2006 | Liu | ............... | A61B 17/1757 606/85 |
| 2007/0010822 A1 * | 1/2007 | Zalenski | ............... | A61B 17/1671 606/79 |
| 2007/0123893 A1 * | 5/2007 | O' Donoghue | ...... | A61B 17/142 606/82 |
| 2007/0233131 A1 | 10/2007 | Song | | |
| 2008/0027449 A1 * | 1/2008 | Gundlapalli | ........ | A61B 17/1624 606/82 |
| 2011/0125174 A1 * | 5/2011 | Babaev | ............... | A61B 17/14 606/169 |
| 2012/0277801 A1 * | 11/2012 | Marik | ............... | A61B 17/025 606/279 |
| 2013/0237843 A1 * | 9/2013 | Linares | ............... | A61B 17/1606 606/176 |
| 2014/0018811 A1 * | 1/2014 | Mootien | ............... | B27B 5/30 83/13 |
| 2016/0128716 A1 * | 5/2016 | Cao | ............... | A61B 17/1659 606/84 |
| 2017/0027586 A1 * | 2/2017 | Ferro | ............... | A61B 17/142 |
| 2018/0132868 A1 | 5/2018 | Dacosta et al. | | |
| 2020/0178999 A1 * | 6/2020 | Stabilini | ........ | A61B 17/320068 |

* cited by examiner

SURGICAL INSTRUMENTS INCLUDING A SET OF CUTTING BURRS FOR PERFORMING AN OSTEOTOMY

REFERENCE TO RELATED APPLICATIONS

This application is a Continuation-In-Part of and claims priority to U.S. patent application Ser. No. 16/459,545, now U.S. Pat. No. 11,376,017, filed on Jul. 1, 2019, and is also a Continuation-In-Part of and claims priority to U.S. patent application Ser. No. 17/538,781, filed on Nov. 30, 2021, which is a Continuation of and claims priority to U.S. patent application Ser. No. 16/537,495, now U.S. Pat. No. 11,253,273, filed on Aug. 9, 2019, which is a Continuation-In-Part of and claims priority to U.S. patent application Ser. No. 16/459,555, now U.S. Pat. No. 11,253,272, filed on Jul. 1, 2019, the contents of each of which are incorporated herein by reference in their entirety.

FIELD OF THE TECHNOLOGY

The present technology relates generally to surgical cutting apparatus, and more particularly to, surgical instruments for performing osteotomies.

BACKGROUND

Surgical cutting instruments come in many shapes and sizes. In performing an osteotomy with a single-sided device, the user (e.g., a physician, surgeon, etc.) is often required to perform multiple cuts and/or passes to achieve a desired shape and/or osteotomy. Further, multiple cuts and/or passes with using a surgical instrument can result in inconsistencies in shape and/or size of the resulting osteotomy in different patients. In other words, it takes more time to perform a osteotomy than is otherwise needed and/or there is a degree of inconsistency and/or inaccuracy when a traditional surgical instrument is utilized to perform an osteotomy.

SUMMARY

Various embodiments provide surgical instruments and methods for performing an osteotomy. A surgical instrument includes a body with a distal end, a proximal end, a first surface, and a second surface. The surgical instrument can include cutting burrs positioned on the first surface and/or the second surface. The surgical instrument can include cutting burrs positioned on the first surface and cutting blades positioned on the second surface.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which.

DETAILED DESCRIPTION OF THE DRAWINGS

Figure 1A:
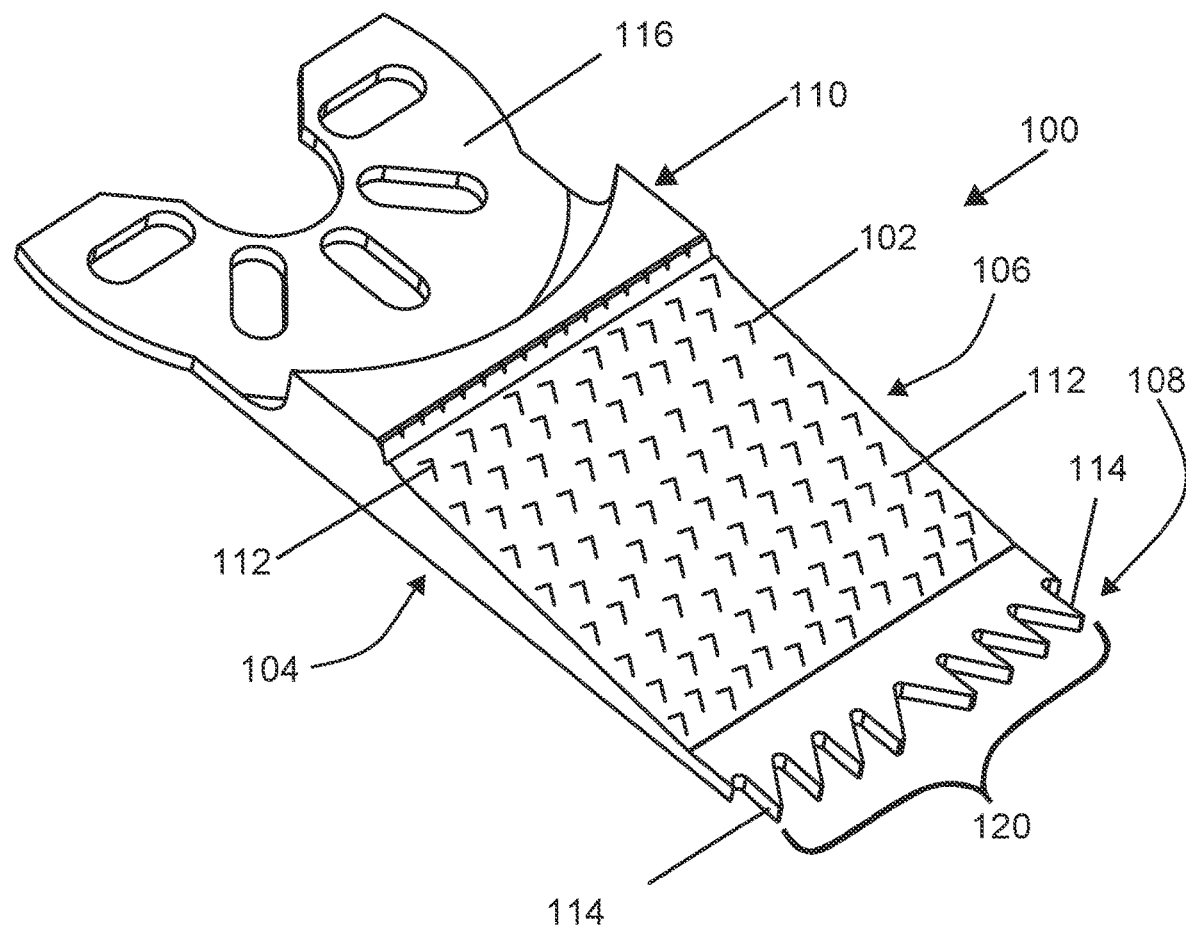
FIGS. 1A through 1E are schematic diagrams illustrating various embodiments of a surgical instrument including cutting burrs on a top surface.
Figure 1B:
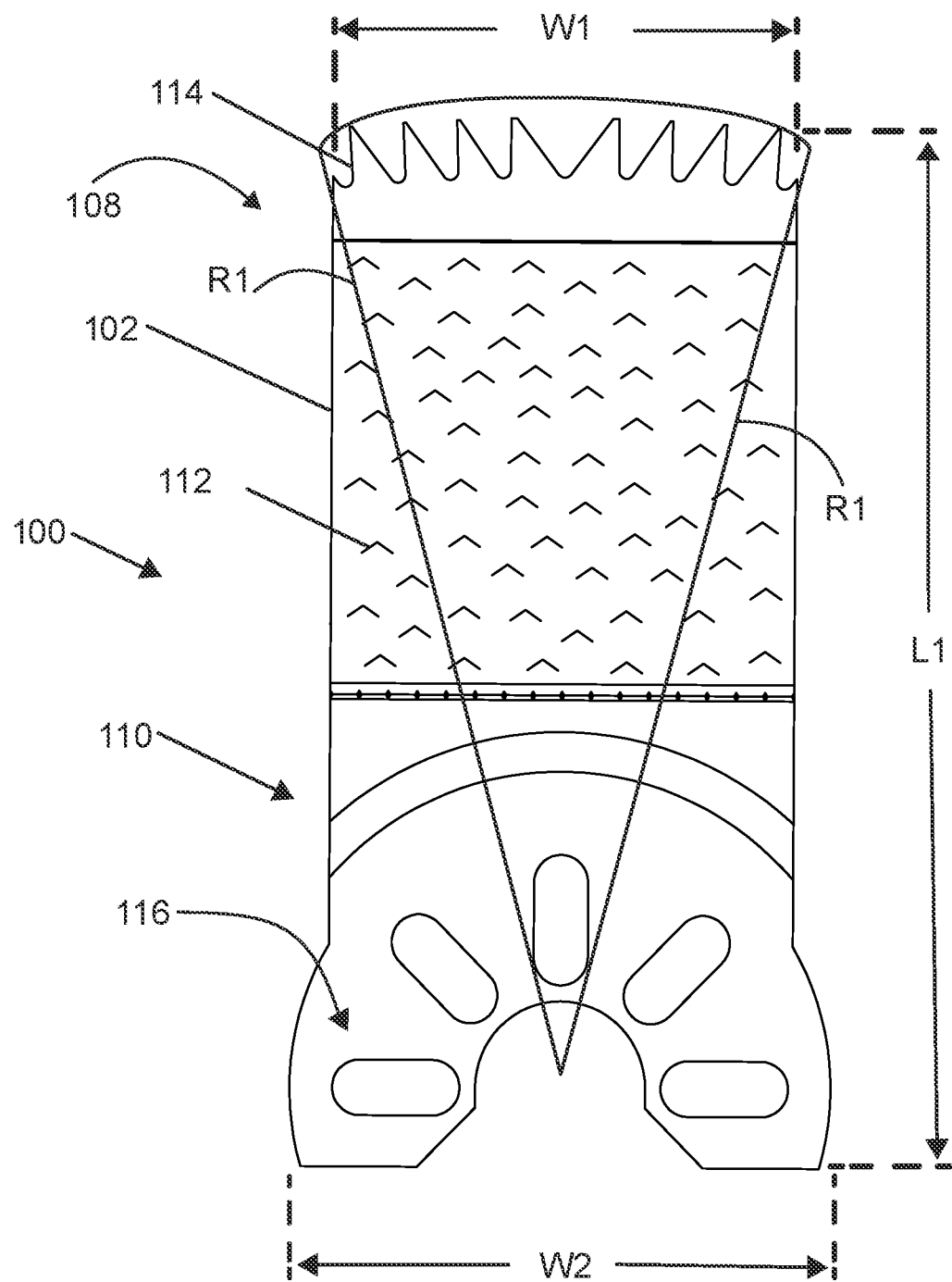

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

Aspects of the embodiments are described below with reference to schematic flowchart diagrams and/or schematic block diagrams of methods, apparatuses, and systems according to embodiments. The schematic flowchart diagrams and/or schematic block diagrams in the Figures illustrate the structure, functionality, and operation of possible implementations of apparatuses, systems, and methods according to various embodiments.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The present technology may include any type of surgical instrument and is not limited to the style of surgical instrument depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1A through 1E are schematic diagrams illustrating various views of various embodiments of a surgical instrument 100. In various embodiments, the surgical instrument 100 can be utilized to perform a wedge-shaped osteotomy. Further, the wedge-shaped osteotomy can be achieved with a single cut or pass utilizing the surgical instrument 100.

A surgical instrument 100 may be constructed of any suitable material that can cut bone. In various embodiments, the surgical instrument 100 is constructed of a sterilized suitable material that can cut bone. In some embodiments, the surgical instrument 100 includes stainless steel, among other suitable materials and combinations of materials that are possible and contemplated herein. In additional or alternative embodiments, the surgical instrument 100 includes surgical grade stainless steel, among other suitable surgical grade materials and combinations of materials that are possible and contemplated herein.

At least in the illustrated embodiment, the surgical instrument 100 includes, among other features, a body 102 including at least a bottom surface 104, a top surface 106, a distal end 108, and a proximal end 110, a set of cutting burrs 112 positioned on the body 102, a set of cutting teeth 114 positioned on the distal end 108, and an attachment mechanism 116 positioned on the proximal end 110. A body 102 may include any suitable dimensions that can perform an osteotomy. The dimensions may include any suitable dimensions that are capable of performing an osteotomy on a human.

In various embodiments, the body 102 includes a length L1 (see FIG. 1B) in the range of about 15 mm to about 70 mm, among other ranges of length and/or lengths that are possible and contemplated herein. In some embodiments, the body 102 includes a length L1 of about 20 mm, among other lengths that are possible and contemplated herein.

The body 102 further includes a width W1 (see FIG. 1B) at the distal end 108 and a width W2 (see FIG. 1B) at the proximal end 110. In various embodiments, the width W1 is in the range of about 5 mm to about 30 mm, among other ranges of widths and/or widths that are possible and contemplated herein. In some embodiments, the width W1 is about 7.5 mm, among other widths that are possible and contemplated herein. In additional or alternative embodiments, the width W2 is in the range of about 5 mm to about 70 mm, among other ranges of widths and/or widths that are possible and contemplated herein. In some embodiments, the width W2 is about 11 mm, among other widths that are possible and contemplated herein.

In some embodiments, the width W1 and the width W2 are the same width or substantially the same width. In other embodiments, the width W2 is greater than the width W1 such that the proximate end 110 is wider than the distal end 108 or, alternatively, the distal end 108 is narrower than the proximate end 110 (e.g., the width W1 is less than the width W2). That is, in various embodiments, the surgical instrument 100 includes a tapered shape and/or tapers from the distal end 108 to the proximate end 110.

A bottom surface 104 may include any suitable shape and/or profile that can facilitate or assist the surgical instrument 100 in performing an osteotomy (e.g., a wedge-shaped osteotomy). In various embodiments, the bottom surface 104 includes a flat or substantially flat surface, among other profiles and/or planes that are possible and contemplated herein.

A top surface 106 may include any suitable profile upon which a set of cutting burrs 112 can be positioned. In various embodiments, the top surface 106 includes a slope 118 (see FIGS. 1C, 1D, and 1E) that extends upward and/or away from the bottom surface 104 and the distal end 108. The slope 118 may include any suitable grade (e.g., rise over run) that can facilitate and/or assist the surgical instrument 100 in performing an osteotomy and particularly, a wedge-shaped osteotomy. That is, the top surface 106 and/or surgical instrument 100 may include any suitable grade that can facilitate and/or assist the surgical instrument 100 in performing a wedge-shaped osteotomy in one cut and/or one pass.

Figure 1C:
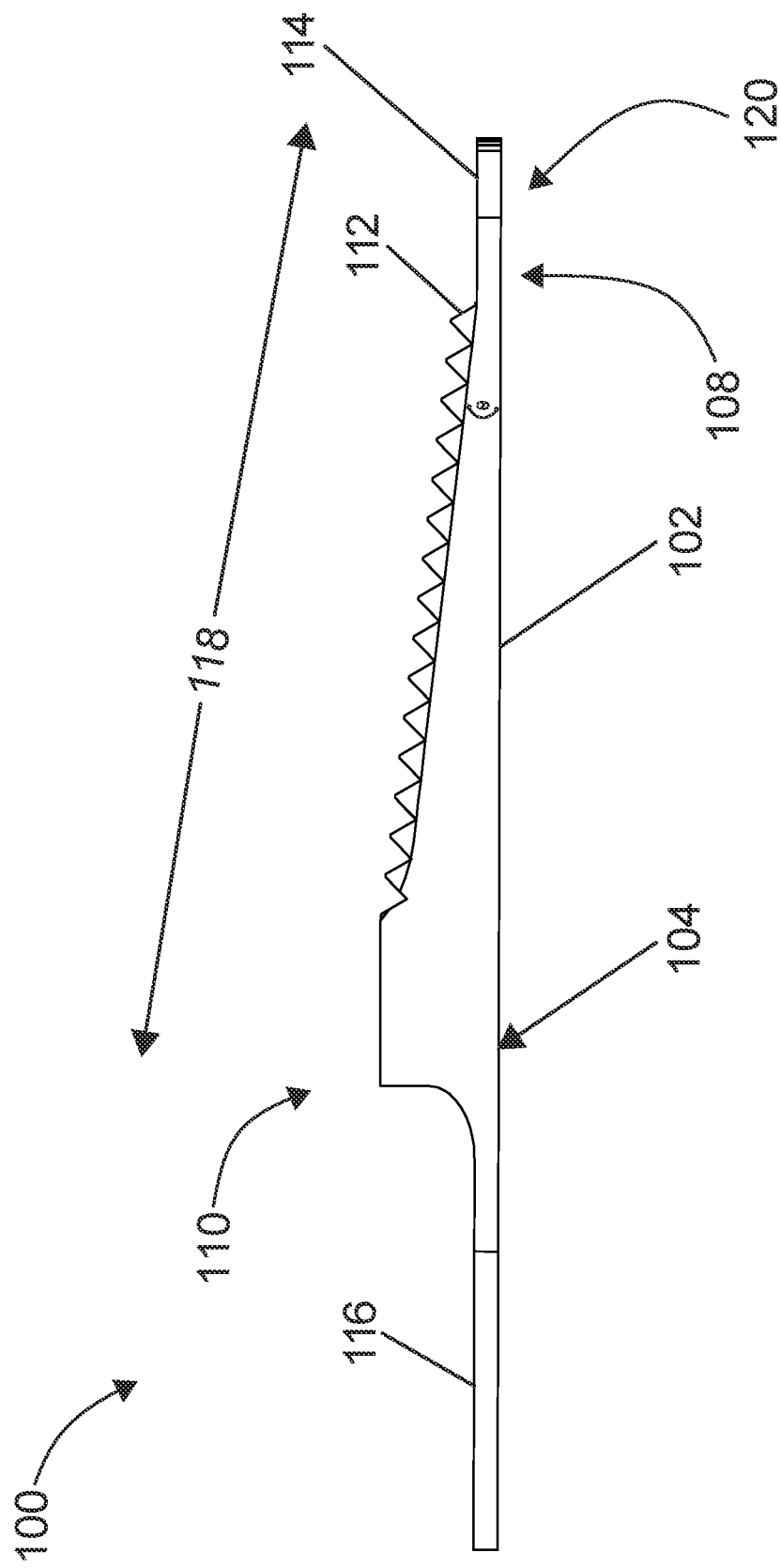
Figure 1D:
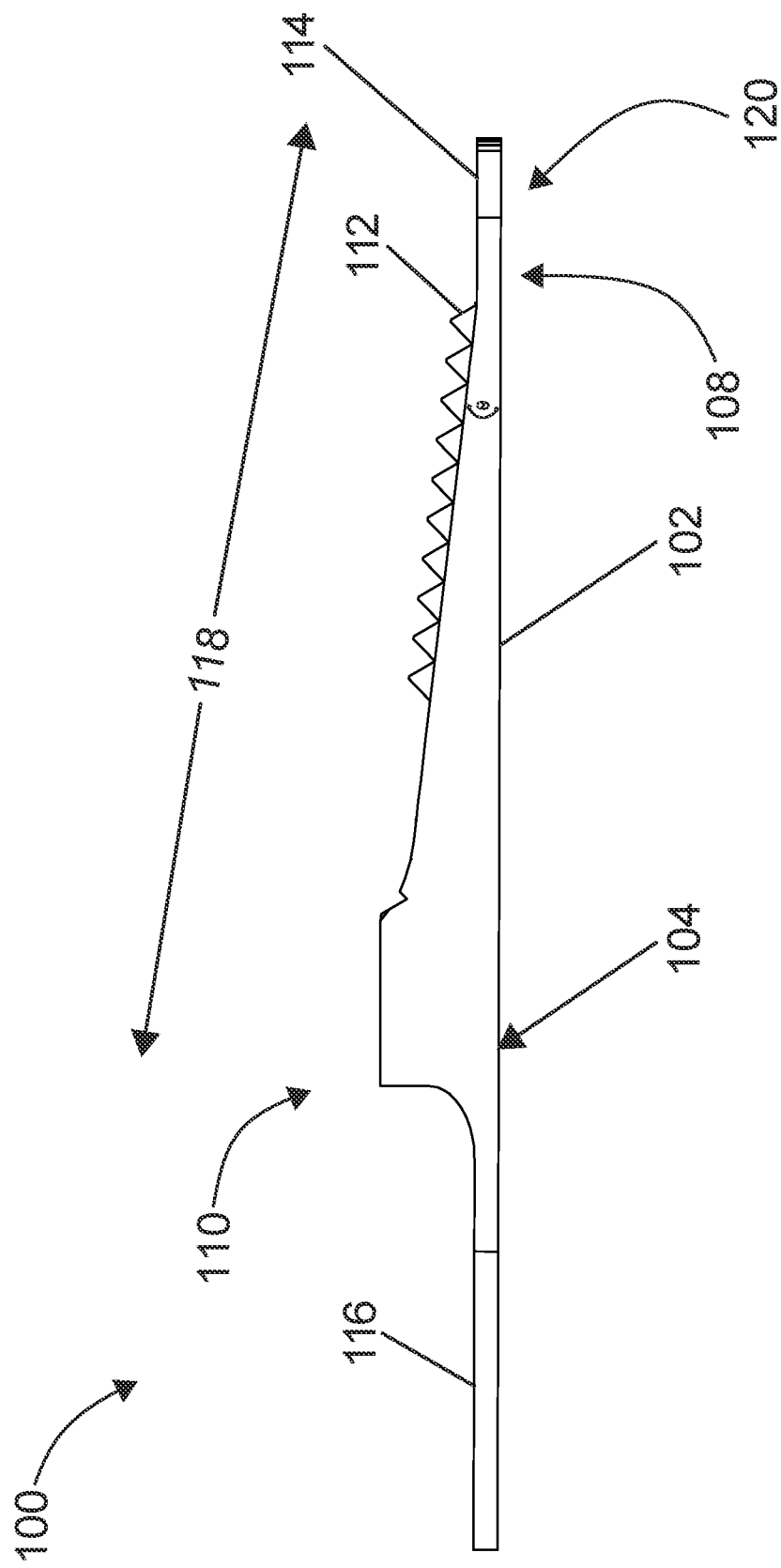
Figure 1E:
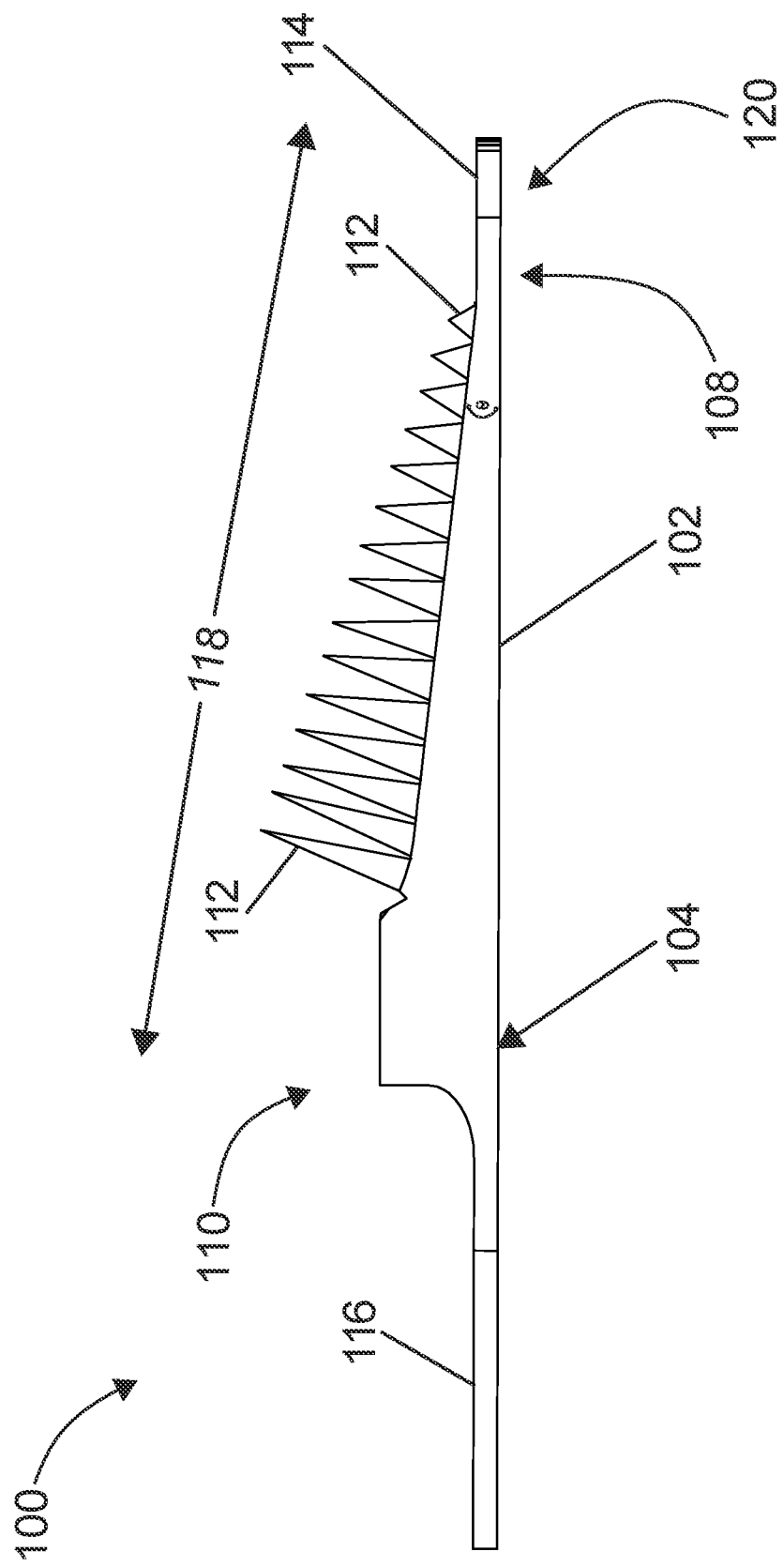

In various embodiments, the slope 118 includes a grade in the range of about zero degrees (0° or flat) to about fifteen degrees (15°), among other ranges of grades, grades, and/or slopes that are possible and contemplated herein. In other words, an angle $\theta$ in the range of about 0° to about 15° (e.g., the angle $\theta$=0°, 1°, 2°, 3°, 4°, 5°, 6°, 7°, 8°, 9°, 10°, 11°, 12°, 13°, 14°, or 15° and/or the angle $\theta\approx$0°, 1°, 2°, 3°, 4°, 5°, 6°, 7°, 8°, 9°, 10°, 11°, 12°, 13°, 14°, or) 15° is defined between the top surface 106 and the bottom surface 104 beginning at the distal end 108 and extending upward and toward the proximate end 110, as shown in FIGS. 1C, 1D, and 1E. In some embodiments, the slope 118 includes a grade of about seven (7°) degrees (e.g., the angle $\theta$=7° or the angle $\theta\approx$7°), among other suitable grades and/or slopes that are possible and contemplated herein.

As illustrated, the top surface 106 includes a set of cutting burrs 112 positioned thereon. The set of cutting burrs 112 may be positioned on the top surface 106 in a patterned configuration or a non-patterned configuration. A patterned configuration (see also surgical instruments 200 and/or 300) may include any suitable pattern of cutting burrs 112 that can assist in and/or facilitate performing an osteotomy and particularly, a wedge-shaped osteotomy. A non-patterned configuration may include any suitable distribution of cutting burrs 112 that can assist in and/or facilitate performing an osteotomy and particularly, a wedge-shaped osteotomy.

A set of cutting burrs 112 may include any suitable quantity of cutting burrs 112 that can facilitate and/or assist the surgical instrument 100 in performing an osteotomy and particularly, a wedge-shaped osteotomy. In various embodiments, the top surface 106 includes a suitable quantity of cutting burrs 112 so that the surgical instrument 100 can perform a wedge-shaped osteotomy in one cut and/or one pass. In various embodiments, the top surface 106 includes a quantity of cutting burrs 112 in the range of about 3 cutting burrs 112 to about 1000 cutting burrs 112, among other ranges of quantities of cutting burrs 112 and/or quantities of cutting burrs 112 that are possible and contemplated herein. In some embodiments, the top surface 106 includes 50 cutting burrs 112, among other quantities of cutting burrs 112 that are possible and contemplated herein.

While the surgical instrument 100 is shown with a top surface 106 including a specific quantity of cutting burrs 112, the various embodiments of the surgical instrument 100 are not limited to the illustrated quantity of cutting burrs 112. That is, various other embodiments of a surgical instrument 100 can include a different quantity of cutting burrs 112 such that the top surface 106 can include a greater quantity of cutting burrs 112 or a smaller quantity of cutting burrs 112 than the illustrated quantity of cutting burrs 112.

In some embodiments, the cutting burrs 112 may be included on the entirety or substantially the entirety of the top surface 106. In other embodiments, the cutting burrs 112 may be included on a portion of the top surface 106 (see FIG. 1D) or at least a portion of the top surface 106.

The portion of the top surface 106 including the cutting burrs 112 may include any suitable sized portion that can produce a wedge-shaped osteotomy. Various embodiments of the surgical instrument 100 may include varying sized portions of the top surface 106 including the cutting burrs 112 so that different sized and/or wedge-shaped osteotomies can be obtained.

A cutting burr 112 may include any suitable shape that can facilitate and/or assist the surgical instrument 100 in performing an osteotomy (e.g., a wedge-shaped osteotomy). In various embodiments, a cutting burr 112 can include a diamond shape, a pointed shape (e.g., a shape that comes to a sharp point), a flame shape, a bullet shape, a cone shape, a tapered shape, or an egg shape, among other suitable shapes that can facilitate cutting bone that are possible and contemplated herein. In additional or alternative embodiments, a cutting burr 112 may be considered the same as or similar to a cutting tooth and/or cutting teeth.

In some embodiments, all of the cutting burrs 112 in the set of cutting burrs 112 on the top surface 106 include the same or substantially the same shape. In alternative embodiments, at least two cutting burrs 112 in the set of cutting burrs 112 on the top surface 106 include different shapes or substantially different shapes. In one non-limiting example, at least one cutting burr 112 includes the diamond shape and at least one cutting burr 112 includes the pointed shape (or other non-diamond shape), among other shapes and/or combinations of shapes that are possible and contemplated herein.

In additional or alternative embodiments, a set of cutting burrs 112 can include at least two subsets of cutting burrs 112 in which a first subset includes two or more cutting burrs 112 including the diamond shape, the flame shape, the pointed shape, the bullet shape, the cone shape, the tapered shape, or the egg shape and at least a second subset includes two or more cutting burrs 112 including a different one of the diamond shape, the flame shape, the pointed shape, the bullet shape, the cone shape, the tapered shape, or the egg shape. In a non-limiting example, a first subset of cutting burrs 112 includes the diamond shape and a second subset of cutting burrs 112 includes the flame shape (or other non-diamond shape), among other shapes and/or combination of shapes that are possible and contemplated herein.

In further additional or alternative embodiments, the first subset of cutting burrs 112 and the second subset of cutting burrs 112 including different shapes include the same quantity of cutting burrs 112. In other embodiments, the first subset of cutting burrs 112 and the second subset of cutting burrs 112 including different shapes include different quantities of cutting burrs 112.

In yet further additional or alternative embodiments, the cutting burrs 112 in the first subset and the cutting burrs 112 in the second subset including different shapes may be distributed on and/or around the top surface 106 of the body 102 in a non-patterned configuration. In other embodiments, the cutting burrs 112 in the first subset of cutting burrs 112 and the cutting burrs 112 in the second subset of cutting burrs 112 including different shapes may be deliberately positioned and/or grouped on and/or around the top surface 106 of the body 102.

In one non-limiting example, the cutting burrs 112 including the diamond shape may be grouped together at a position at or near the distal end 108 (or away from the proximate end 110) or grouped together at a position at or near the proximate end 110 (or away from the distal end 108) and the cutting burrs 112 including an egg shape (or other non-diamond shape) may be positioned opposite the cutting burrs 112 including the diamond shape, among other shapes and/or combinations of shapes that are possible and contemplated herein. In another non-limiting example, a greater quantity of the cutting burrs 112 including the diamond shape may be grouped together at a position at or near the distal end 108 (or away from the proximate end 110) than is grouped together at a position at or near the proximate end 110 (or away from the distal end 108) and the cutting burrs 112 including the non-diamond shape may be positioned opposite the cutting burrs 112 including the diamond shape or vice-versa, among other shapes and/or combinations of shapes that are possible and contemplated herein.

A cutting burr 112 may include any suitable height that can facilitate and/or assist the surgical instrument 100 in performing an osteotomy (e.g., a wedge-shaped osteotomy). In various embodiments, the cutting burrs 112 can include a height in the range of about 0.1 mm to about 30 mm, among other suitable heights that can facilitate cutting bone that are possible and contemplated herein. In some embodiments, the cutting burrs 112 include a height of 0.75 mm.

In some embodiments, all of the cutting burrs 112 in the set of cutting burrs 112 on the top surface 106 can include the same or substantially the same height (see FIG. 1C). In alternative embodiments, at least two cutting burrs 112 in the set of cutting burrs 112 on the top surface 106 include different heights or substantially different heights (see FIG. 1E). In additional or alternative embodiments, a set of cutting burrs 112 can include at least two subsets of cutting burrs 112 in which a first subset includes two or more cutting burrs 112 including a first height that is taller than at least a second subset that includes two or more cutting burrs 112.

In further additional or alternative embodiments, the first subset of cutting burrs 112 and the second subset of cutting burrs 112 including different heights can include the same quantity of cutting burrs 112. In other further additional or alternative embodiments, the first subset of cutting burrs 112 and the second subset of cutting burrs 112 including different heights can include different quantities of cutting burrs 112.

In yet further additional or alternative embodiments, the cutting burrs 112 in the first subset of cutting burrs 112 and the cutting burrs 112 in the second subset of cutting burrs 112 including different heights may be randomly distributed on and/or around the top surface 106 of the body 102. In other embodiments, the cutting burrs 112 in the first subset of cutting burrs 112 and the cutting burrs 112 in the second subset of cutting burrs 112 including different heights may be deliberately positioned and/or grouped on and/or around the top surface 106 of the body 102.

In one non-limiting example, the cutting burrs 112 including the greater height may be grouped together at a position at or near the proximate end 110 (or away from the distal end 108) and the cutting burrs 112 including the smaller height may be positioned at the distal end 108 (or away from the proximate end 110). In another non-limiting example, a greater quantity of the cutting burrs 112 including the smaller height may be grouped together at a position at or near the distal end 108 (or away from the proximate end 110) than is grouped together at a position at or near the proximate end 110 (or away from the distal end 108) and the cutting burrs 112 including the greater height may be positioned opposite the cutting burrs 112 including the smaller height.

As shown, the distal end 108 includes a set of cutting teeth 114 (e.g., a single tooth 114 or multiple teeth 114) positioned thereon. A set of cutting teeth 114 may include any suitable quantity of teeth 114 that can assist in and/or facilitate initiating an osteotomy when oscillated and particularly, a wedge-shaped osteotomy.

In various embodiments, the set of cutting teeth 114 includes a quantity of cutting teeth 114 in the range of one (1) cutting tooth 114 to about 50 cutting teeth 114, among other ranges of quantities and/or quantities of cutting teeth 114 that are possible and contemplated herein. In some embodiments, a set of cutting teeth 114 includes about 8 cutting teeth 114, among other quantities of cutting teeth 114 that are possible and contemplated herein.

In some embodiments, the set of cutting teeth 114 is positioned on the distal end 110 in a straight line or substantially straight line. In other embodiments, the set of cutting teeth 114 is positioned along a curve on the distal end 110 defined by a radius R1.

The radius R1 may be any suitable radius and/or curvature that can assist in and/or facilitate initiating an osteotomy (e.g., a wedge-shaped osteotomy) when oscillated. In various embodiments, the radius R1 is in the range of about 5 mm to about 80 mm, among other ranges of lengths and/or lengths that can define an amount and/or degree of curvature that are possible and contemplated herein. In some embodiments, the radius R1 is about 25 mm, among other lengths that can define an amount and/or degree of curvature that are possible and contemplated herein.

In some embodiments, the set of cutting teeth 114 on the distal end may define a cutting tip 120 that can initiate an osteotomy. Further, the cutting burrs 112 positioned along the single-plane slope 118 may define a cutting slope 118 that can perform the osteotomy to produce a wedge-shaped cut. In various embodiments, the coordination of the cutting tip 120 and the cutting slope 118 can allow the surgical instrument 100 to produce a wedge-shaped osteotomy in a single cut and/or single pass.

As further shown, the proximal end 110 includes an attachment mechanism 116 positioned thereon. The attachment mechanism 116 may include any suitable size dimensions, shape, and/or configuration that enables attachments of the surgical instrument 100 to another surgical instrument (not shown). That is, while the attachment mechanism 116 is shown as including particular relative size dimensions, shapes, and configurations, the various embodiments of the surgical instrument 100 are not limited to the illustrated attachment mechanism 116. That is, other embodiments of the surgical instrument 100 may include one or more different relative size dimension(s), shapes, and/or configurations.

FIGS. 2A through 2E are schematic diagrams illustrating various views of one embodiment of a surgical instrument 200. In various embodiments, the surgical instrument 200 can be utilized to perform a wedge-shaped osteotomy. Further, a wedge-shaped osteotomy can be achieved with a single cut or pass utilizing the surgical instrument 200.

A surgical instrument 200 may be constructed of any suitable material that can cut bone. In various embodiments, the surgical instrument 200 is constructed of a sterilized suitable material that can cut bone. In some embodiments, the surgical instrument 200 includes stainless steel, among other suitable materials that are possible and contemplated herein. In additional or alternative embodiments, the surgical instrument 200 includes surgical grade stainless steel, among other suitable surgical grade materials that are possible and contemplated herein.

At least in the illustrated embodiment, the surgical instrument 200 includes, among other features, a body 202 including at least a bottom surface 204, a top surface 206, a distal end 208, and a proximal end 210, a set of cutting burrs 212 positioned on the body 202 and arranged in multiple rows 222 (e.g., a plurality of rows 222), a set of cutting teeth 214 positioned on the distal end 208, and an attachment mechanism 216 positioned on the proximal end 210. A body 202 may include any suitable dimensions that can perform an osteotomy. In various embodiments, the body 202 includes dimensions that are suitable for performing an osteotomy on a human.

In various embodiments, the body 202 includes a length L2 (see FIG. 2B) in the range of about 15 mm to about 70 mm, among other ranges of length and/or lengths that are possible and contemplated herein. In some embodiments, the body 202 includes a length L2 of about 20 mm, among other lengths that are possible and contemplated herein.

The body 202 further includes a width W3 (see FIG. 2B) at the distal end 208 and a width W4 (see FIG. 2B) at the proximal end 210. In various embodiments, the width W3 is in the range of about 5 mm to about 30 mm, among other ranges of widths and/or widths that are possible and contemplated herein. In some embodiments, the width W3 is about 7.5 mm, among other widths that are possible and contemplated herein. In additional or alternative embodiments, the width W4 is in the range of about 5 mm to about 70 mm, among other ranges of widths and/or widths that are possible and contemplated herein. In some embodiments, the width W4 is about 11 mm, among other widths that are possible and contemplated herein.

In some embodiments, the width W3 and the width W4 are the same width or substantially the same width. In other embodiments, the width W4 is greater than the width W3 such that the proximate end 210 is wider than the distal end 208 or, alternatively, the distal end 208 is narrower than the proximate end 210 (e.g., the width W3 is less than the width W4). That is, in various embodiments, the surgical instrument 200 includes a tapered shape and/or tapers from the distal end 208 to the proximate end 210.

A bottom surface 204 may include any suitable shape and/or profile that can facilitate or assist the surgical instrument 200 in performing an osteotomy (e.g., a wedge-shaped osteotomy). In various embodiments, the bottom surface 204 includes a flat or substantially flat surface, among other profiles and/or planes that are possible and contemplated herein.

A top surface 206 may include any suitable profile upon which a set of cutting burrs 212 can be positioned. In various embodiments, the top surface 206 includes a slope 218 (see FIGS. 2C, 2D, and 2E) that extends upward and/or away from the bottom surface 204. The slope 218 may include any suitable grade (e.g., rise over run) that can facilitate and/or assist the surgical instrument 200 in performing an osteotomy and particularly, a wedge-shaped osteotomy. That is, the top surface 206 and/or surgical instrument 200 may include any suitable grade that can facilitate and/or assist the surgical instrument 200 in performing a wedge-shaped osteotomy in one cut and/or one pass.

Figure 2A:
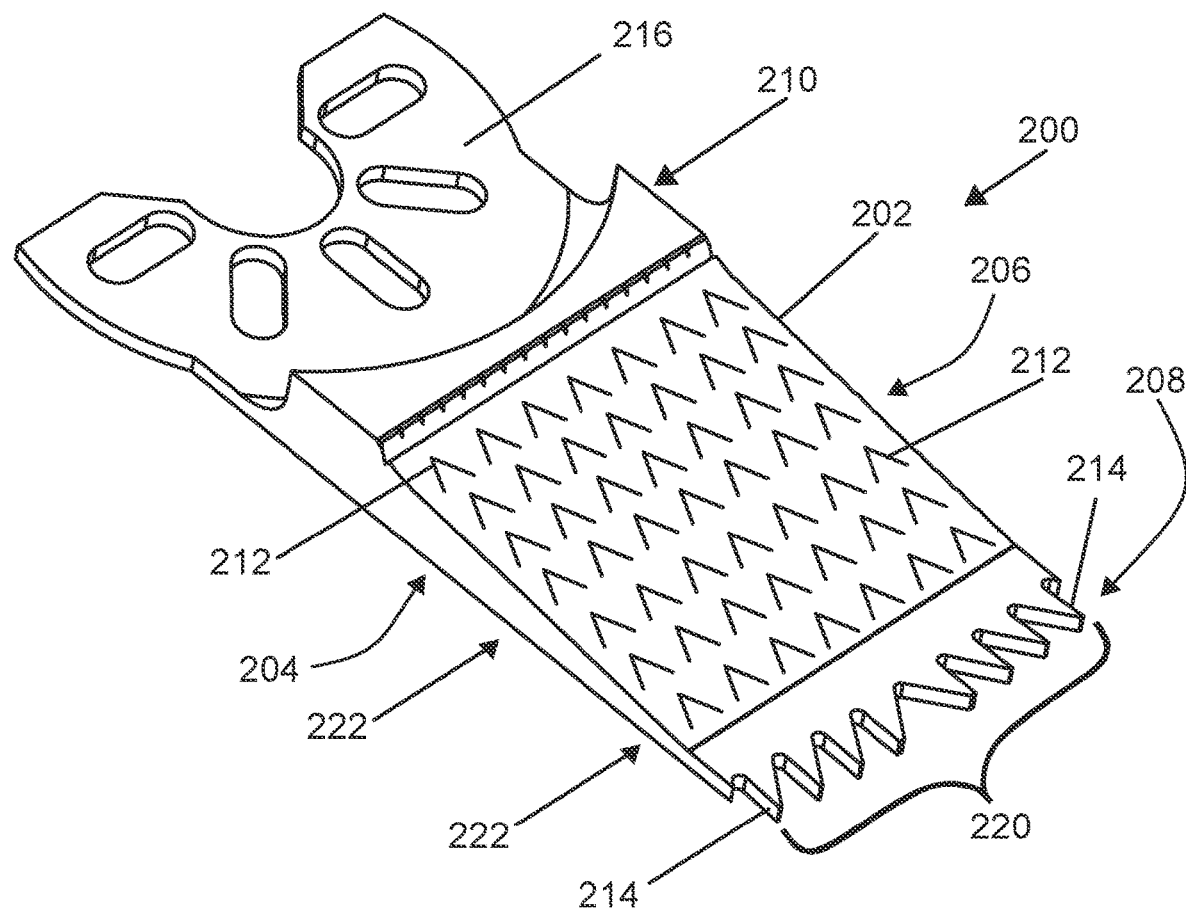
FIGS. 2A through 2E are schematic diagrams illustrating various other embodiments of a surgical instrument including cutting burrs on a top surface.
Figure 2B:
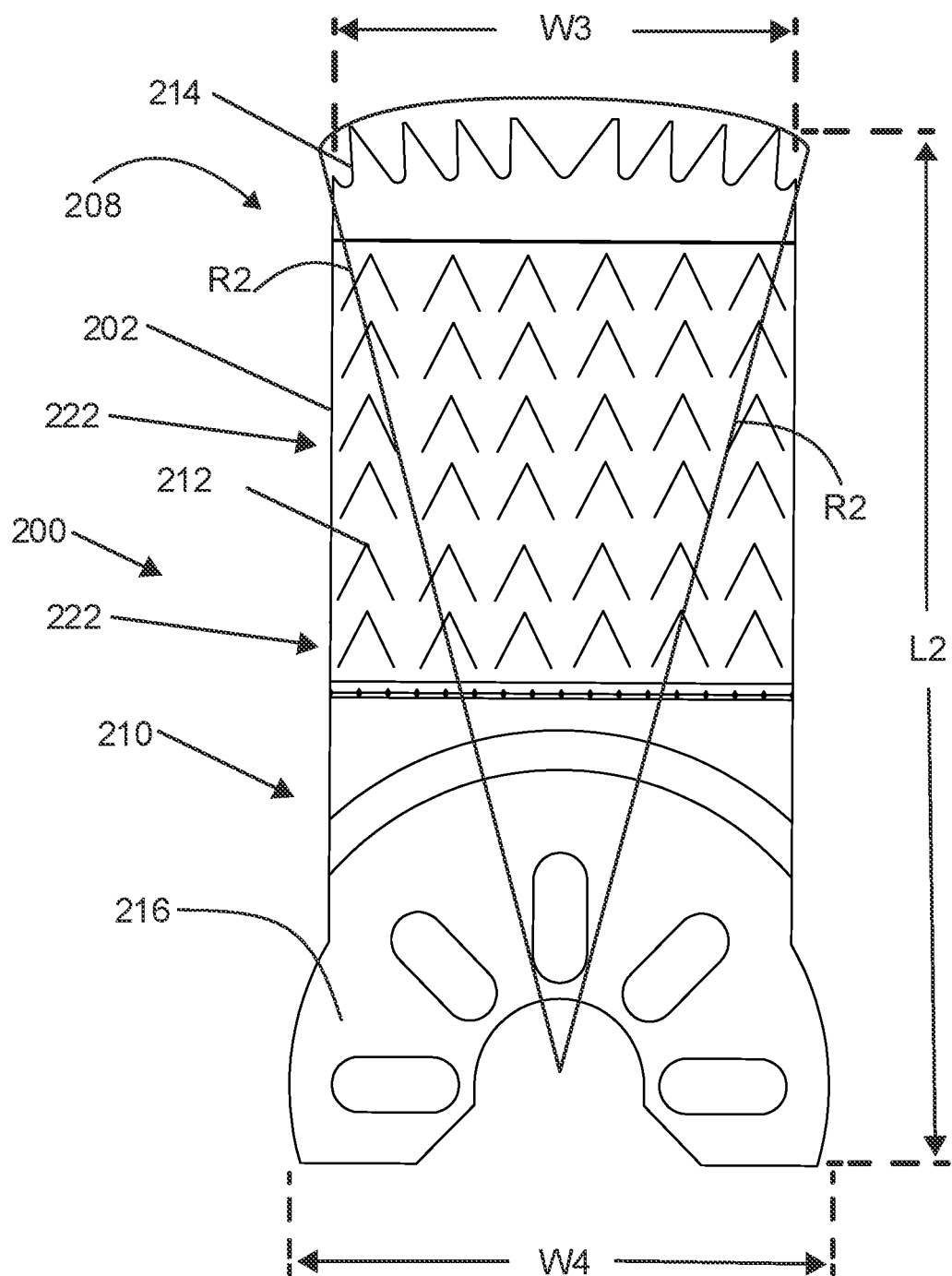
Figure 2C:
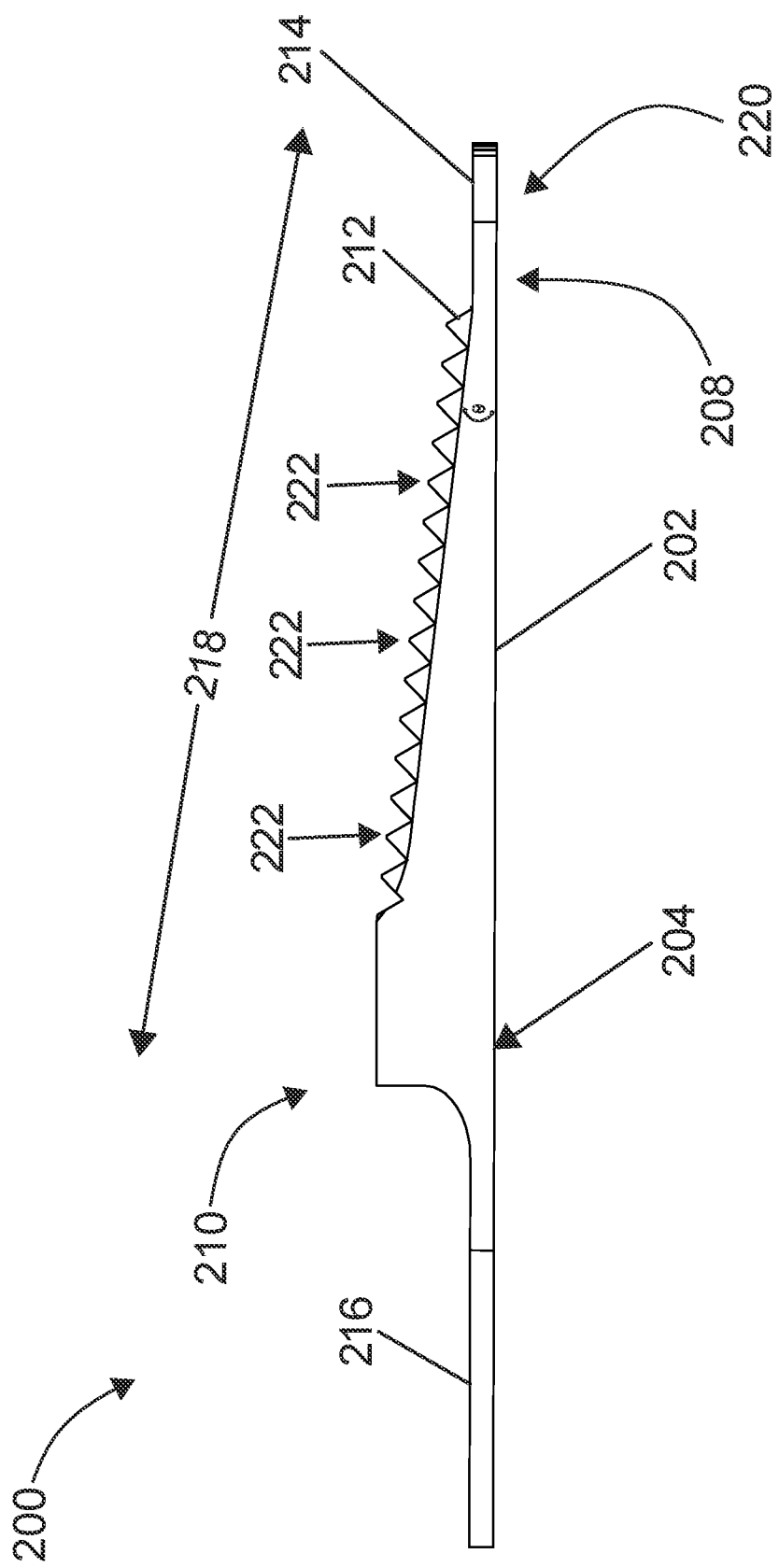
Figure 2D:
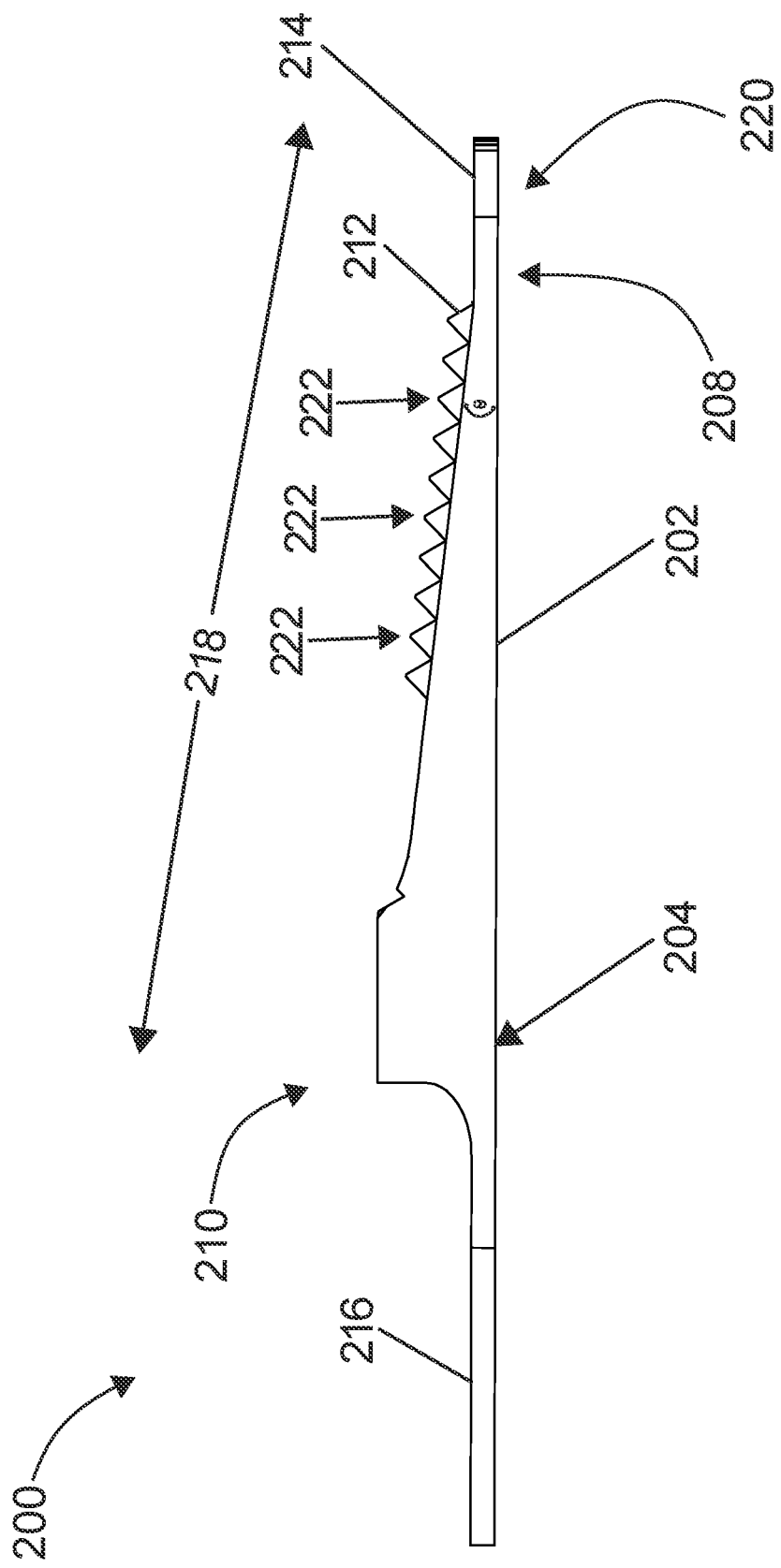
Figure 2E:
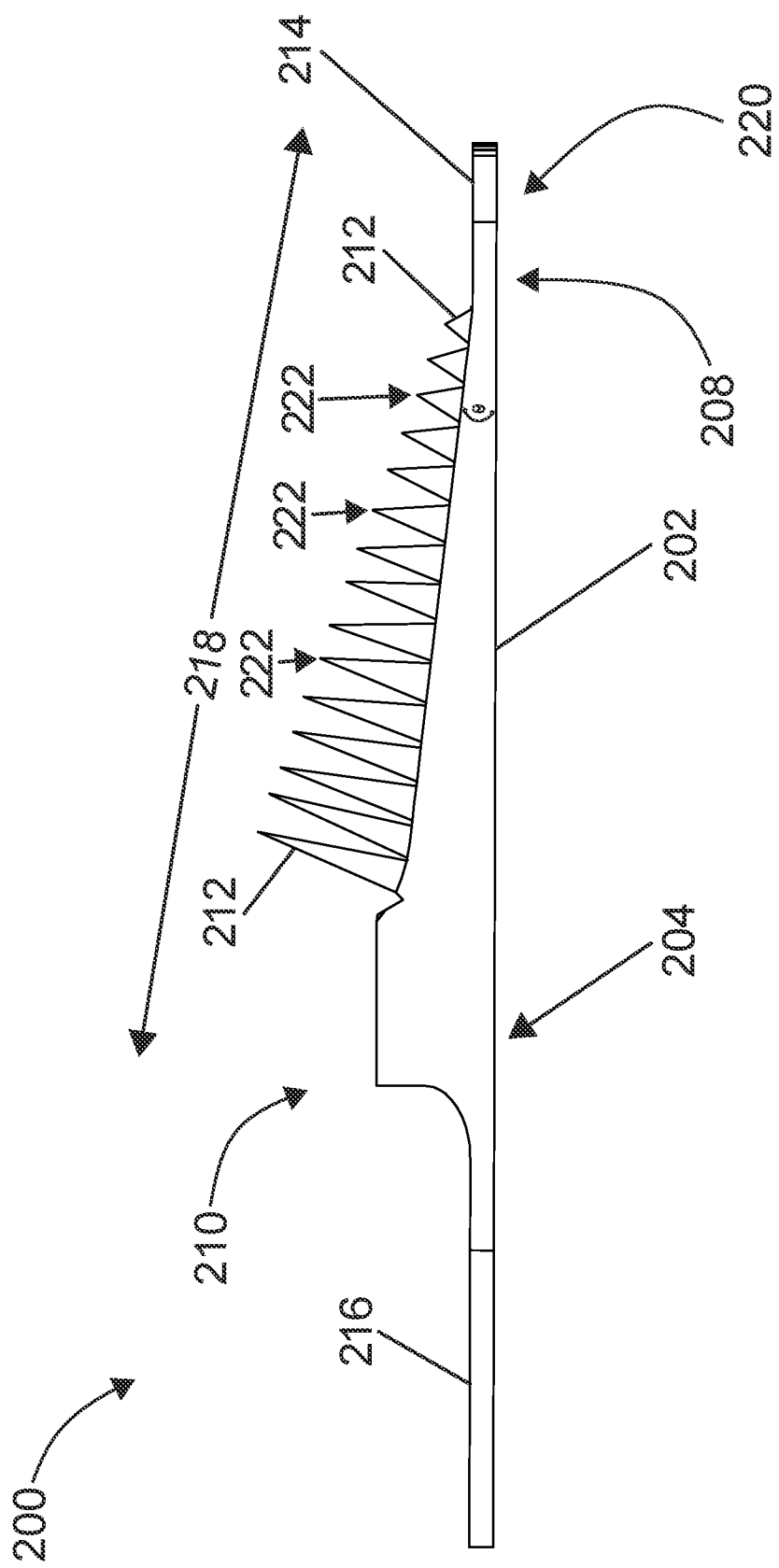

In various embodiments, the slope 218 includes a grade in the range of about 0° (or flat) to about 15°, among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 206 and the bottom surface 204 beginning at the distal end 208 and extending upward and toward the proximate end 210, as shown in FIGS. 2C, 2D, and 2E. In some embodiments, the slope 218 includes a grade of about 7° degrees (e.g., the angle θ=7° or the angle θ≈7°), among other suitable grades and/or slopes that are possible and contemplated herein.

As illustrated, the top surface 206 includes a set of rows 222 of cutting burrs 212 arranged thereon. The top surface 206 may include any quantity of rows 222 of cutting burrs 212 that can facilitate and/or assist the surgical instrument 200 in performing an osteotomy and particularly, a wedge-shaped osteotomy.

In various embodiments, a set of rows 222 can include a quantity of rows 222 in the range of about two (2) rows 222 of cutting burrs 212 to about 40 rows 222 of cutting burrs 212, among other ranges of quantities and/or quantities that are possible and contemplated herein. In some embodiments, a set of rows 222 includes 12 rows 222 of cutting burrs 212, among other quantities that are possible and contemplated herein.

A row 222 of cutting burrs 212 may include any suitable quantity of cutting burrs 212 that can facilitate and/or assist the surgical instrument 200 in performing an osteotomy and particularly, a wedge-shaped osteotomy. In various embodiments, each row 222 of cutting burrs 212 includes a suitable quantity of cutting burrs 212 so that the surgical instrument 200 can perform a wedge-shaped osteotomy in one cut and/or one pass.

In some embodiments, the top surface 206 includes a quantity of rows 222 of cutting burrs 212 in the range of 1 row 222 of two (2) cutting burrs 212 (e.g., 1×2 cutting burrs 212) to 50 rows 222 of 20 cutting burrs 212 (e.g., 50×20 cutting burrs 212), among other ranges and/or sized matrices that are possible and contemplated herein. In one embodiment, the top surface 206 includes 12 rows 222 of 12 cutting burrs 212 (e.g., 12×12 cutting burrs 212), among other sized matrices that are possible and contemplated herein.

In various embodiments, each row 222 of cutting burrs 212 includes the same quantity of cutting burrs 212. Here, each row 222 of cutting burrs 212 can include a quantity of cutting burrs 212 in the range of about two (2) cutting burrs 212 to about 40 cutting burrs 212, among other ranges of quantities and/or quantities that are possible and contemplated herein. In some embodiments, each row 222 of cutting burrs 212 includes 12 cutting burrs 212, among other quantities that are possible and contemplated herein.

In alternative embodiments, two or more rows 222 of cutting burrs 212 include different quantities of cutting burrs 212. In some embodiments, a first row 222 of cutting burrs 212 can include a quantity of cutting burrs 212 in the range of about two (2) cutting burrs 212 to about 40 cutting burrs 212, among other ranges of quantities and/or quantities that are possible and contemplated herein, and a second row 222 of cutting burrs 212 can include a different quantity of cutting burrs 212 in the range of cutting burrs 212.

While the surgical instrument 200 is shown as including 7 rows 222 of cutting burrs 212, the various embodiments of the surgical instrument 200 are not limited to 7 rows 222 of cutting burrs 212. That is, various other embodiments of a surgical instrument 200 can include a different quantity of rows 222 of cutting burrs 212 such that the top surface 206 can include a greater quantity of rows 222 of cutting burrs 212 than 7 rows 222 of cutting burrs 212 or a smaller quantity of rows 222 of cutting burrs 212 than 7 rows 222 of cutting burrs 212.

In some embodiments, the rows 222 of cutting burrs 212 may be included on the entirety or substantially the entirety of the top surface 206. In other embodiments, the rows 222 of cutting burrs 212 may be included on a portion of the top surface 206 (see FIG. 2D) or at least a portion of the top surface 206.

The portion of the top surface 206 including the rows 222 of cutting burrs 212 may include any suitable sized portion that can produce a wedge-shaped osteotomy. Various embodiments of the surgical instrument 200 may include varying sized portions of the top surface 206 including the rows 222 of cutting burrs 212 so that different sized and/or wedge-shaped osteotomies can be obtained.

A cutting burr 212 may include any suitable shape that can facilitate and/or assist the surgical instrument 200 in performing an osteotomy (e.g., a wedge-shaped osteotomy). In various embodiments, a cutting burr 212 can include a diamond shape, a pointed shape, a flame shape, a bullet shape, a cone shape, a tapered shape, and an egg shape, among other suitable shapes that can facilitate cutting bone that are possible and contemplated herein. In additional or alternative embodiments, a cutting burr 212 may be considered the same as or similar to a cutting tooth and/or cutting teeth.

In some embodiments, all of the cutting burrs 212 in each of the rows 222 of cutting burrs 212 on the top surface 206 include the same or substantially the same shape. In alternative embodiments, at least two rows 222 of cutting burrs 212 on the top surface 206 include different shapes or substantially different shapes. In one non-limiting example, at least one row 222 of cutting burrs 212 includes the diamond shape and at least one row 222 of cutting burrs 212 includes the pointed shape (or other non-diamond shape), among other shapes and/or combinations of shapes that are possible and contemplated herein.

In additional or alternative embodiments, the rows 222 of cutting burrs 212 can be positioned on the top surface 106 in a pattern. The pattern may include any suitable pattern that can assist in and/or facilitate performing an osteotomy. In some embodiments, the pattern may include rows 222 of cutting burrs 212 with different shapes in an alternating pattern to provide alternating rows of cutting burrs 212.

In further additional or alternative embodiments, the rows 222 of cutting burrs 212 different shapes may include the same quantity of cutting burrs 212. In other additional or alternative embodiments, the rows 222 of cutting burrs 212 including different shapes may include different quantities of cutting burrs 212.

In yet further additional or alternative embodiments, the rows 222 of cutting burrs 212 may be deliberately positioned and/or grouped on and/or around the top surface 206 of the body 202. In one non-limiting example, the row(s) 222 of cutting burrs 212 including the diamond shape may be grouped together at a position at or near the distal end 208 (or away from the proximate end 210) or grouped together at a position at or near the proximate end 210 (or away from the distal end 208) and the row(s) 222 of cutting burrs 212 including a non-diamond shape may be positioned opposite the row(s) 222 of cutting burrs 212 including the diamond shape, among other shapes and/or combinations of shapes that are possible and contemplated herein. In another non-limiting example, a greater quantity of rows 222 of cutting burrs 212 including the diamond shape may be grouped together at a position at or near the distal end 208 (or away from the proximate end 210) than is grouped together at a position at or near the proximate end 210 (or away from the distal end 208) and the row(s) 222 of cutting burrs 212 including the non-diamond shape may be positioned opposite the row(s) 222 of cutting burrs 212 including the diamond shape or vice-versa, among other shapes and/or combinations of shapes that are possible and contemplated herein.

A cutting burr 212 may include any suitable height that can facilitate and/or assist the surgical instrument 200 in performing an osteotomy (e.g., a wedge-shaped osteotomy). In various embodiments, the cutting burrs 212 can include a height in the range of about 0.1 mm to about 30 mm, among other suitable heights that can facilitate cutting bone that are possible and contemplated herein. In some embodiments, the cutting burrs 212 include a height of 0.75 mm.

In some embodiments, all of the cutting burrs 212 in the set of cutting burrs 212 on the top surface 206 include the same or substantially the same height (see FIG. 2C). In alternative embodiments, at least two rows 222 of cutting burrs 212 on the top surface 206 include different heights or substantially different heights such that a first row 222 includes a first height that is taller than at least a second row 222.

In various embodiments, the row(s) 222 of cutting burrs 212 including the greater height may be grouped together at a position at or near the proximate end 210 (or away from the distal end 208) and the row(s) 222 of cutting burrs 212 including the smaller height may be positioned at the distal end 208 (or away from the proximate end 210). In additional or alternative embodiments, a greater quantity of rows 222 of cutting burrs 212 including the smaller height may be grouped together at a position at or near the distal end 208 (or away from the proximate end 210) than is grouped together at a position at or near the proximate end 210 (or away from the distal end 208) and the cutting burrs 212 including the greater height may be positioned opposite the cutting burrs 212 including the smaller height.

In further additional or alternative embodiments, the rows 222 of cutting burrs 212 on the top surface 206 each include a different height or a substantially different height. In some embodiments, the rows 222 of cutting burrs 212 include a gradually increasing height from the distal end 108 to the proximal end 110 (e.g., see FIG. 2E).

As shown, the distal end 208 includes a set of cutting teeth 214 (e.g., a single tooth 214 or multiple teeth 214) positioned thereon. A set of cutting teeth 214 may include any suitable quantity of teeth 214 that can assist in and/or facilitate initiating an osteotomy when oscillated and particularly, a wedge-shaped osteotomy.

In various embodiments, the set of cutting teeth 214 includes a quantity of cutting teeth 114 in the range of one cutting tooth 214 to about 50 cutting teeth 214, among other ranges of quantities and/or quantities of cutting teeth 214 that are possible and contemplated herein. In some embodiments, a set of cutting teeth 214 includes about 8 cutting teeth 214, among other quantities of cutting teeth 214 that are possible and contemplated herein.

In some embodiments, the set of cutting teeth 214 is positioned on the distal end 210 in a straight line or substantially straight line. In other embodiments, the set of cutting teeth 214 is positioned along a curve on the distal end 210 defined by a radius R2.

The radius R2 may be any suitable radius and/or curvature that can assist in and/or facilitate initiating an osteotomy (e.g., a wedge-shaped osteotomy) when oscillated. In various embodiments, the radius R2 is in the range of about 5 mm to about 80 mm, among other ranges of lengths and/or lengths that can define an amount and/or degree of curvature that are possible and contemplated herein. In some embodiments, the radius R2 is about 25 mm, among other lengths that can define an amount and/or degree of curvature that are possible and contemplated herein.

In some embodiments, the set of cutting teeth 214 on the distal end may define a cutting tip 220 that can initiate an osteotomy. Further, the cutting burrs 212 positioned along the single-plane slope 218 may define a cutting slope 218 that can perform the osteotomy to produce a wedge-shaped cut. In various embodiments, the coordination of the cutting tip 220 and the cutting slope 218 can allow the surgical instrument 200 to produce a wedge-shaped osteotomy in a single cut and/or single pass.

As further shown, the proximal end 210 includes an attachment mechanism 216 positioned thereon. The attachment mechanism 216 may include any suitable size dimensions, shape, and/or configuration that enables attachments of the surgical instrument 200 to another surgical instrument (not shown). That is, while the attachment mechanism 216 is shown as including particular relative size dimensions, shapes, and configurations, the various embodiments of the surgical instrument 200 are not limited to the illustrated attachment mechanism 216. That is, other embodiments of the surgical instrument 200 may include one or more different relative size dimension(s), shapes, and/or configurations.

FIGS. 3A through 3E are schematic diagrams illustrating various views of one embodiment of a surgical instrument 300. In various embodiments, the surgical instrument 300 can be utilized to perform a wedge-shaped osteotomy. Further, a wedge-shaped osteotomy can be achieved with a single cut or pass utilizing the surgical instrument 300.

A surgical instrument 300 may be constructed of any suitable material that can cut bone. In various embodiments, the surgical instrument 300 is constructed of a sterilized suitable material that can cut bone. In some embodiments, the surgical instrument 300 includes stainless steel, among other suitable materials that are possible and contemplated herein. In additional or alternative embodiments, the surgical instrument 300 includes surgical grade stainless steel, among other suitable surgical grade materials that are possible and contemplated herein.

At least in the illustrated embodiment, the surgical instrument 300 includes, among other features, a body 302 including at least a bottom surface 304, a top surface 306, a distal end 308, and a proximal end 310, a set of cutting burrs 312 positioned on the body 302 and arranged in multiple columns 322 (e.g., a plurality of columns 322), a set of cutting teeth 314 positioned on the distal end 308, and an attachment mechanism 316 positioned on the proximal end 310. A body 302 may include any suitable dimensions that can perform an osteotomy. In various embodiments, the body 302 includes dimensions that are suitable for performing an osteotomy on a human.

In various embodiments, the body 302 includes a length L3 (see FIG. 3B) in the range of about 15 mm to about 70 mm, among other ranges of length and/or lengths that are possible and contemplated herein. In some embodiments, the body 302 includes a length L3 of about 20 mm, among other lengths that are possible and contemplated herein.

The body 302 further includes a width W5 (see FIG. 3B) at the distal end 308 and a width W6 (see FIG. 3B) at the proximal end 310. In various embodiments, the width W5 is in the range of about 5 mm to about 30 mm, among other ranges of widths and/or widths that are possible and contemplated herein. In some embodiments, the width W5 is about 7.5 mm, among other widths that are possible and contemplated herein. In additional or alternative embodiments, the width W6 is in the range of about 5 mm to about 70 mm, among other ranges of widths and/or widths that are possible and contemplated herein. In some embodiments, the width W6 is about 11 mm, among other widths that are possible and contemplated herein.

In some embodiments, the width W5 and the width W6 are the same width or substantially the same width. In other embodiments, the width W6 is greater than the width W5 such that the proximate end 310 is wider than the distal end 308 or, alternatively, the distal end 308 is narrower than the proximate end 310 (e.g., the width W5 is less than the width W6). That is, in various embodiments, the surgical instrument 300 includes a tapered shape and/or tapers from the distal end 308 to the proximate end 310.

A bottom surface 304 may include any suitable shape and/or profile that can facilitate or assist the surgical instrument 300 in performing an osteotomy (e.g., a wedge-shaped osteotomy). In various embodiments, the bottom surface 304 includes a flat or substantially flat surface, among other profiles and/or planes that are possible and contemplated herein.

A top surface 306 may include any suitable profile upon which a set of cutting burrs 312 can be positioned. In various embodiments, the top surface 306 includes a slope 318 (see FIGS. 3C, 3D, and 3E) that extends upward and/or away from the bottom surface 304. The slope 318 may include any suitable grade (e.g., rise over run) that can facilitate and/or assist the surgical instrument 300 in performing an osteotomy and particularly, a wedge-shaped osteotomy. That is, the top surface 306 and/or surgical instrument 300 may include any suitable grade that can facilitate and/or assist the surgical instrument 300 in performing a wedge-shaped osteotomy in one cut and/or one pass.

Figure 3A:
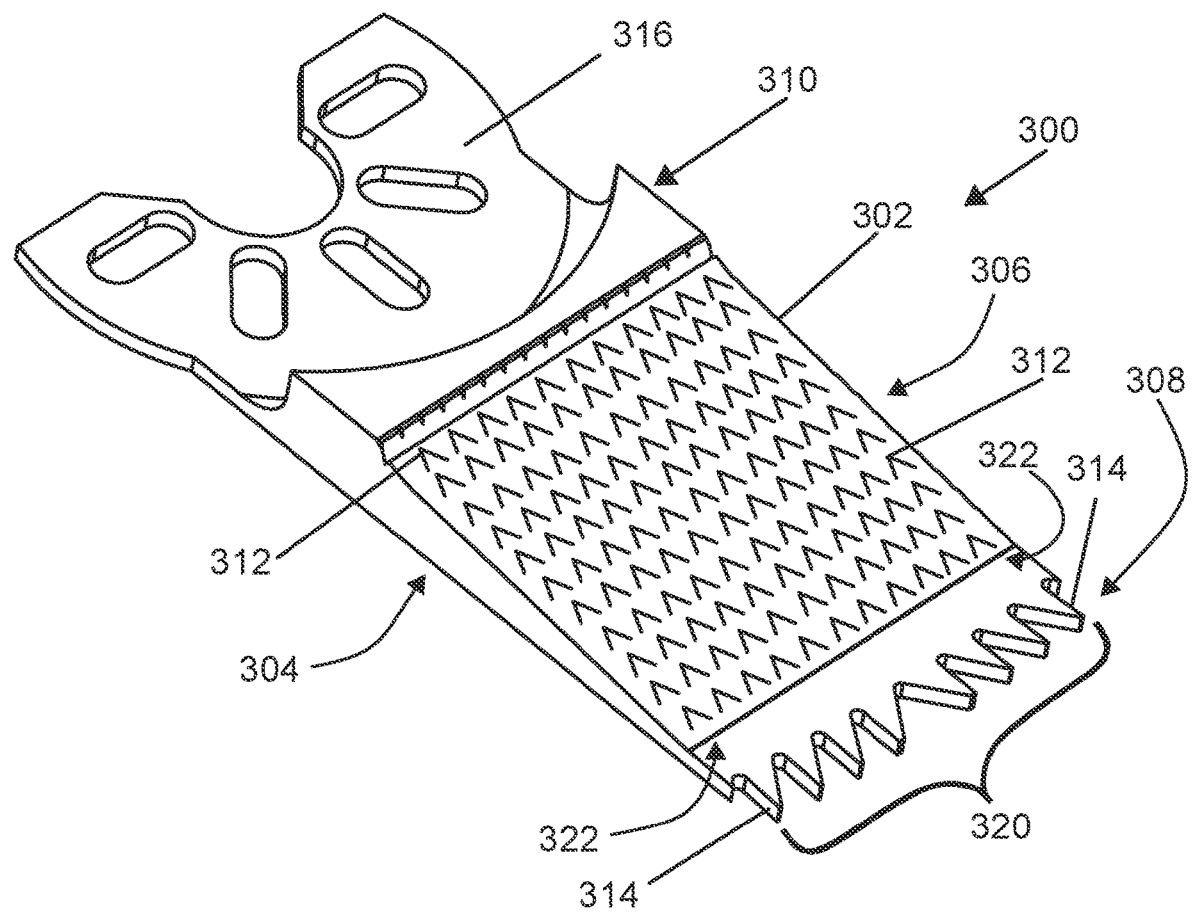
FIGS. 3A through 3E are schematic diagrams illustrating various further embodiments of a surgical instrument including cutting burrs on a top surface.
Figure 3B:
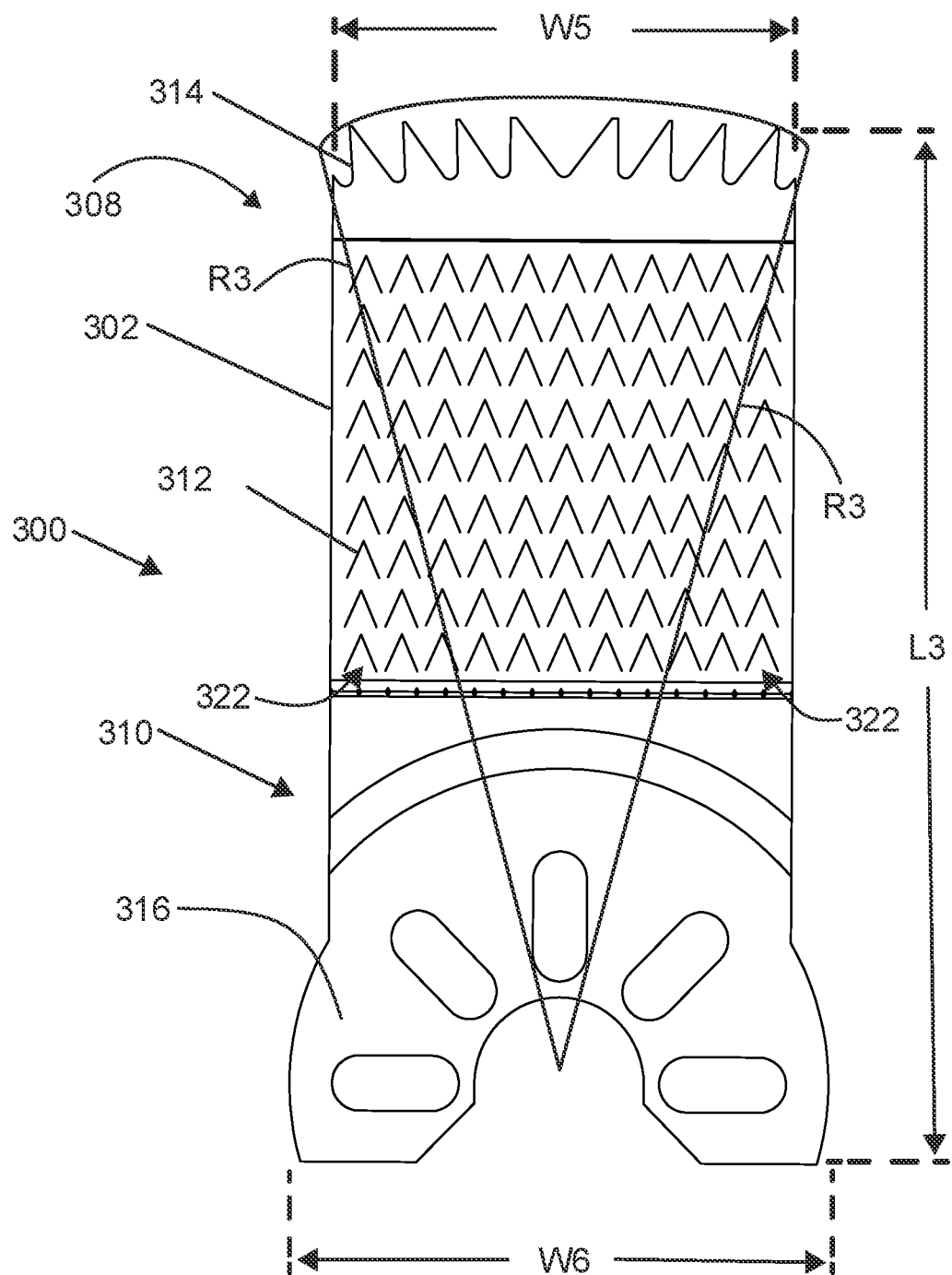
Figure 3C:
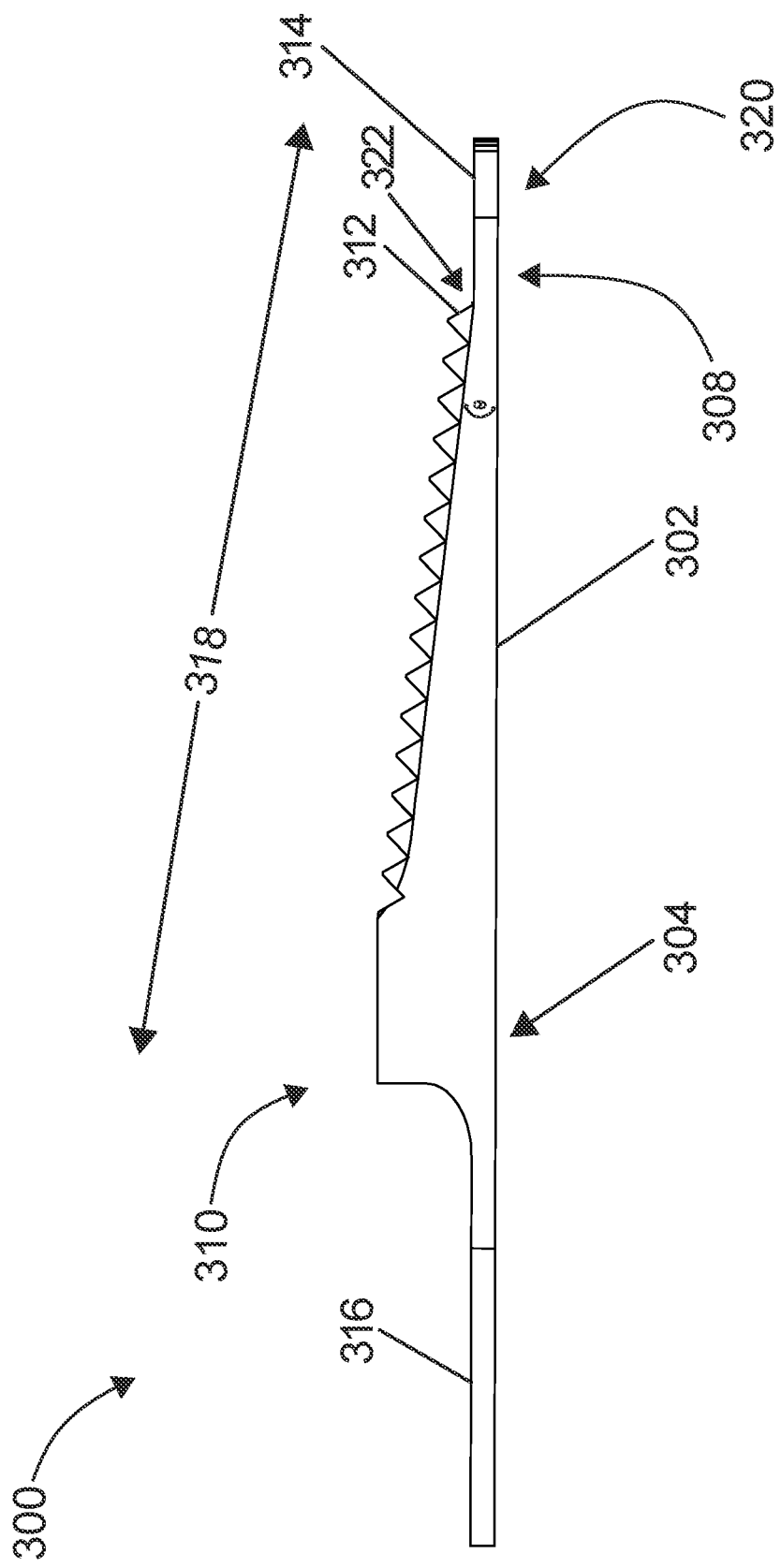
Figure 3D:
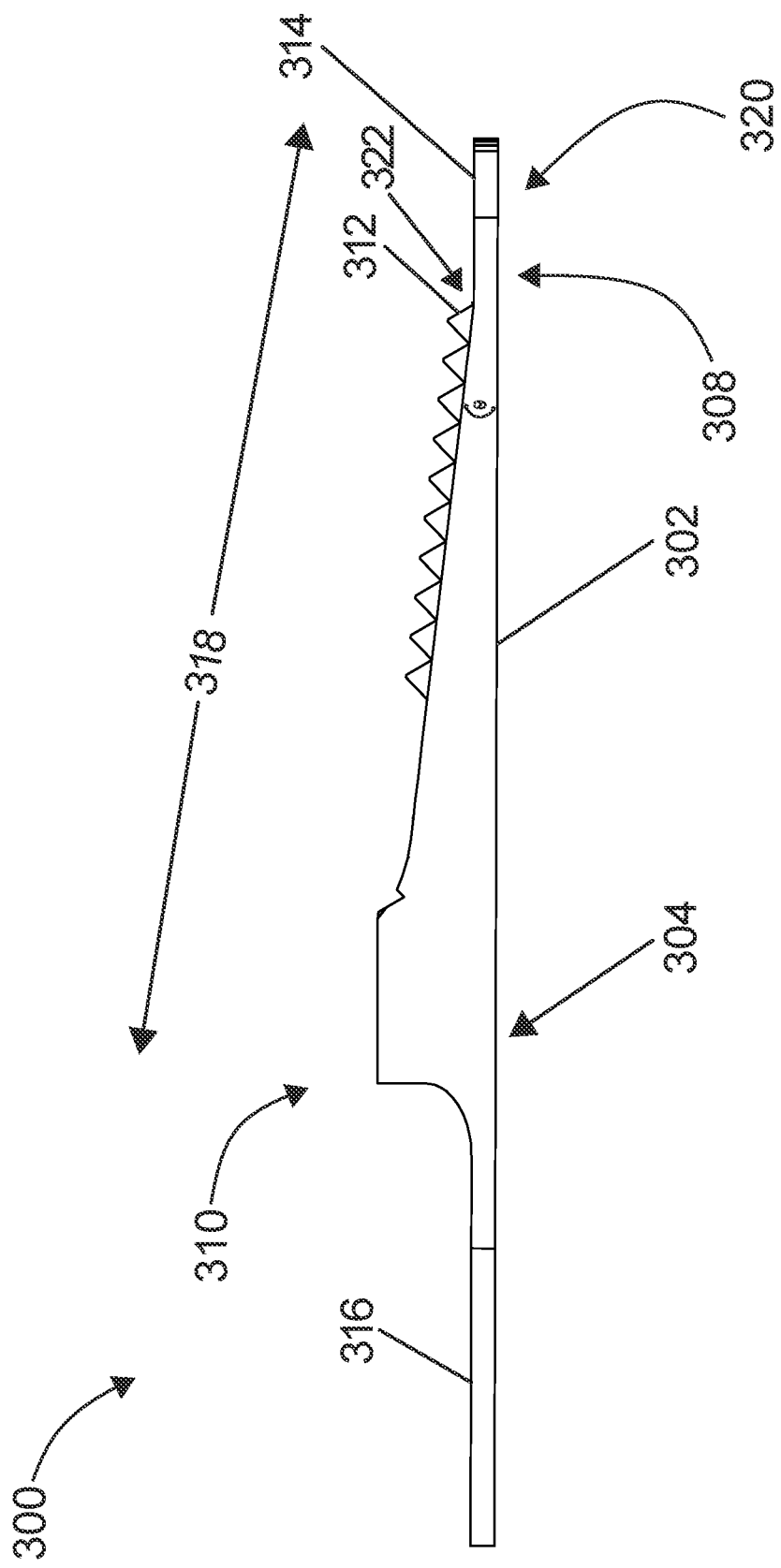
Figure 3E:
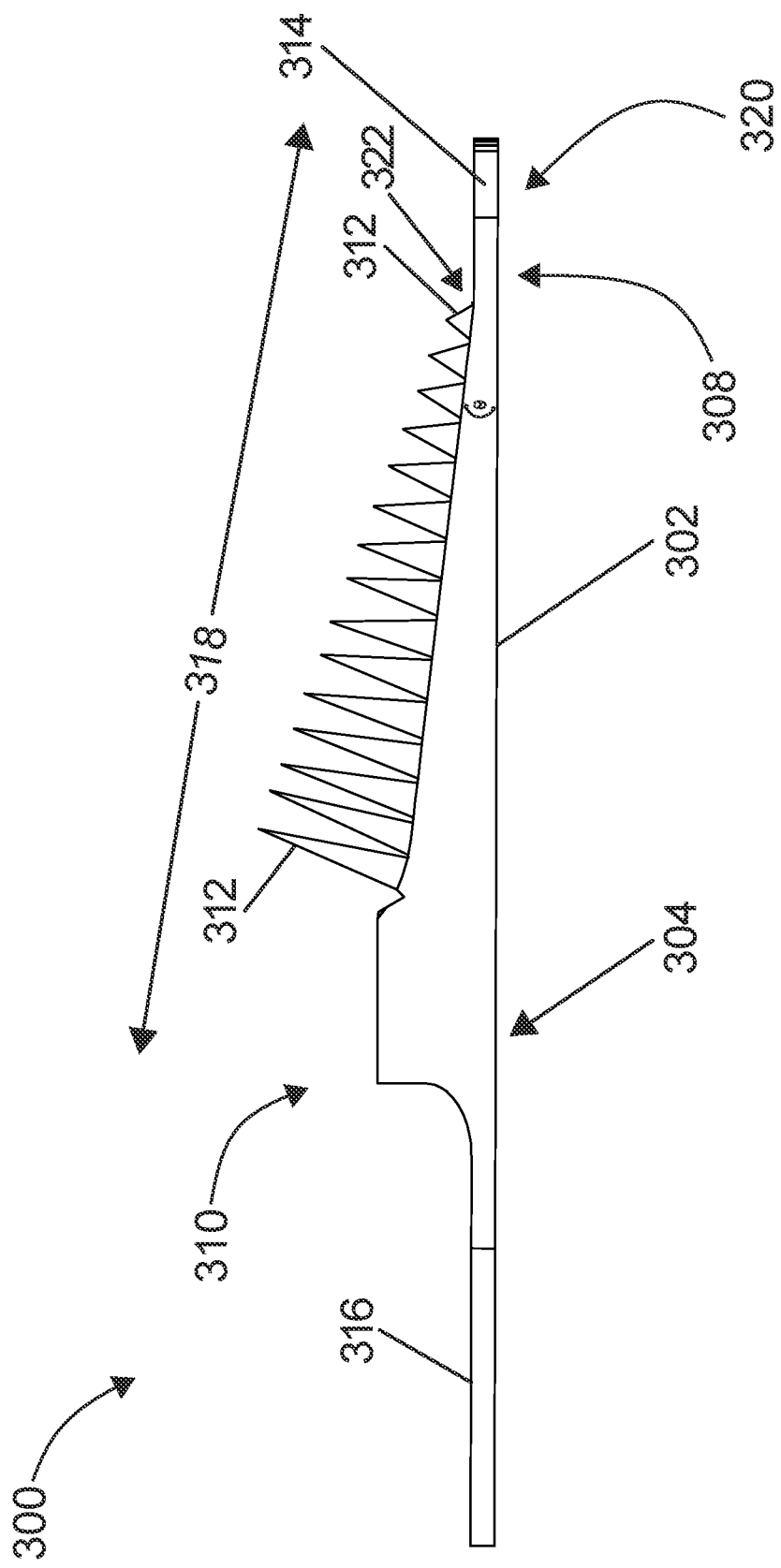

In various embodiments, the slope 318 includes a grade in the range of about 0° (or flat) to about 15°, among other ranges of grades, grades, and/or slopes that are possible and contemplated herein. In other words, an angle $\theta$ in the range of about 0° to about 15° (e.g., the angle $\theta$=0°, 1°, 2°, 3°, 4°, 5°, 6°, 7°, 8°, 9°, 10°, 11°, 12°, 13°, 14°, or 15° and/or the angle $\theta$≈0°, 1°, 2°, 3°, 4°, 5°, 6°, 7°, 8°, 9°, 10°, 11°, 12°, 13°, 14°, or 15°) is defined between the top surface 306 and the bottom surface 304 beginning at the distal end 308 and extending upward and toward the proximate end 310, as shown in FIGS. 3C, 3D, and 3E. In some embodiments, the slope 318 includes a grade of about 7° degrees (e.g., the angle $\theta$=7° or the angle $\theta$≈7°), among other suitable grades and/or slopes that are possible and contemplated herein.

As illustrated, the top surface 306 includes a set of columns 322 of cutting burrs 312 arranged thereon. The top surface 306 may include any quantity of columns 322 of cutting burrs 312 that can facilitate and/or assist the surgical instrument 300 in performing an osteotomy and particularly, a wedge-shaped osteotomy. In various embodiments, a set of columns 322 can include a quantity of columns 322 in the range of about two (2) columns 322 of cutting burrs 312 to about 40 columns 322 of cutting burrs 312, among other ranges of quantities and/or quantities that are possible and contemplated herein. In some embodiments, a set of columns 322 includes 12 columns 322 of cutting burrs 312, among other quantities that are possible and contemplated herein.

A column 322 of cutting burrs 312 may include any suitable quantity of cutting burrs 312 that can facilitate and/or assist the surgical instrument 300 in performing an osteotomy and particularly, a wedge-shaped osteotomy. In various embodiments, each column 322 of cutting burrs 312 includes a suitable quantity of cutting burrs 312 so that the surgical instrument 300 can perform a wedge-shaped osteotomy in one cut and/or one pass.

In some embodiments, the top surface 306 includes a quantity of columns 322 of cutting burrs 312 in the range of 1 column 322 of two (2) cutting burrs 312 (e.g., 1×2 cutting burrs 312) to 20 columns 322 of 50 cutting burrs 312 (e.g., 20×50 cutting burrs 312), among other ranges and/or sized matrices that are possible and contemplated herein. In one embodiment, the top surface 306 includes 12 columns 322 of 12 cutting burrs 312 (e.g., 12×12 cutting burrs 312), among other sized matrices that are possible and contemplated herein.

In various embodiments, each column 322 of cutting burrs 312 includes the same quantity of cutting burrs 312. Here, each column 322 of cutting burrs 312 can include a quantity of cutting burrs 312 in the range of about 3 cutting burrs 312 to about 40 cutting burrs 312, among other ranges of quantities and/or quantities that are possible and contemplated herein. In some embodiments, each column 322 of cutting burrs 312 includes 11 cutting burrs 312, among other quantities that are possible and contemplated herein.

In alternative embodiments, two or more columns 322 of cutting burrs 312 include different quantities of cutting burrs 312. In some embodiments, a first column 322 of cutting burrs 312 can include a quantity of cutting burrs 312 in the range of about 3 cutting burrs 312 to about 40 cutting burrs 312, among other ranges of quantities and/or quantities that are possible and contemplated herein, and a second column 322 of cutting burrs 312 can include a different quantity of cutting burrs 312 in the range of cutting burrs 312.

While the surgical instrument 300 is shown as including 11 columns 322 of cutting burrs 312, the various embodiments of the surgical instrument 300 are not limited to 11 columns 322 of cutting burrs 312. That is, various other embodiments of a surgical instrument 300 can include a different quantity of columns 322 of cutting burrs 312 such that the top surface 306 can include a greater quantity of columns 322 of cutting burrs 312 than 11 columns 322 of cutting burrs 312 or a smaller quantity of columns 322 of cutting burrs 312 than 11 columns 322 of cutting burrs 312.

In some embodiments, the columns 322 of cutting burrs 312 may be included on the entirety or substantially the entirety of the top surface 306. In other embodiments, the columns 322 of cutting burrs 312 may be included on a portion of the top surface 306 (see FIG. 3D) or at least a portion of the top surface 306.

The portion of the top surface 306 including the columns 322 of cutting burrs 312 may include any suitable sized portion that can produce a wedge-shaped osteotomy. Various embodiments of the surgical instrument 300 may include varying sized portions of the top surface 306 including the columns 322 of cutting burrs 312 so that different sized and/or wedge-shaped osteotomies can be obtained.

A cutting burr 312 may include any suitable shape that can facilitate and/or assist the surgical instrument 300 in performing an osteotomy (e.g., a wedge-shaped osteotomy). In various embodiments, a cutting burr 312 can include a diamond shape, a pointed shape, a flame shape, a bullet shape, a cone shape, a tapered shape, and an egg shape, among other suitable shapes that can facilitate cutting bone that are possible and contemplated herein. In additional or alternative embodiments, a cutting burr 312 may be considered the same as or similar to a cutting tooth and/or cutting teeth.

In some embodiments, all of the cutting burrs 312 in each of the columns 322 of cutting burrs 312 on the top surface 306 include the same or substantially the same shape. In alternative embodiments, at least two columns 322 of cutting burrs 312 on the top surface 306 include different shapes or substantially different shapes. In one non-limiting example, at least one column 322 of cutting burrs 312 includes the diamond shape and at least one column 322 of cutting burrs 312 includes the pointed shape (or other non-diamond shape), among other shapes and/or combinations of shapes that are possible and contemplated herein.

In additional or alternative embodiments, the columns 322 of cutting burrs 312 can be positioned on the top surface 106 in a pattern. The pattern may include any suitable pattern that can assist in and/or facilitate performing an osteotomy. In some embodiments, the pattern may include columns 322 of cutting burrs 312 with different shapes in an alternating pattern to provide alternating columns of cutting burrs 312.

In further additional or alternative embodiments, the columns 322 of cutting burrs 312 different shapes may include the same quantity of cutting burrs 312. In other additional or alternative embodiments, the columns 322 of cutting burrs 312 including different shapes may include different quantities of cutting burrs 312.

A cutting burr 312 may include any suitable height that can facilitate and/or assist the surgical instrument 300 in performing an osteotomy (e.g., a wedge-shaped osteotomy). In various embodiments, the cutting burrs 312 can include a height in the range of about 0.1 mm to about 30 mm, among other suitable heights that can facilitate cutting bone that are possible and contemplated herein. In some embodiments, the cutting burrs 312 include a height of 0.75 mm.

In some embodiments, all of the cutting burrs 312 in the set of cutting burrs 312 on the top surface 306 include the same or substantially the same height (see FIG. 3C). In alternative embodiments, at least one column 322 on the top surface 306 includes cutting burrs 312 with different heights or substantially different heights such that a first cutting burr 312 includes a height that is taller than at least a second cutting burr 312 in the column 322.

In various embodiments, the cutting burr(s) 312 including the greater height may be located at a position in its/their respective column 322 that at or near the proximate end 310 (or away from the distal end 308) and the cutting burr(s) 312 including the smaller height may be positioned at the distal end 308 (or away from the proximate end 310). In some embodiments, the columns 322 of cutting burrs 312 include a set of cutting burrs 312 therein that include a gradually increasing height from the distal end 108 to the proximal end 110 (e.g., see FIG. 3E).

As shown, the distal end 308 includes a set of cutting teeth 314 (e.g., a single tooth 314 or multiple teeth 314) positioned thereon. A set of cutting teeth 314 may include any suitable quantity of teeth 314 that can assist in and/or facilitate initiating an osteotomy when oscillated and particularly, a wedge-shaped osteotomy.

In various embodiments, the set of cutting teeth 314 includes a quantity of cutting teeth 314 in the range of one cutting tooth 314 to about 50 cutting teeth 314, among other ranges of quantities and/or quantities of cutting teeth 314 that are possible and contemplated herein. In some embodiments, a set of cutting teeth 314 includes about 8 cutting teeth 314, among other quantities of cutting teeth 314 that are possible and contemplated herein.

In some embodiments, the set of cutting teeth 314 is positioned on the distal end 310 in a straight line or substantially straight line. In other embodiments, the set of cutting teeth 314 is positioned along a curve on the distal end 310 defined by a radius R3.

The radius R3 may be any suitable radius and/or curvature that can assist in and/or facilitate initiating an osteotomy (e.g., a wedge-shaped osteotomy) when oscillated. In various embodiments, the radius R3 is in the range of about 5 mm to about 80 mm, among other ranges of lengths and/or lengths that can define an amount and/or degree of curvature that are possible and contemplated herein. In some embodiments, the radius R3 is about 25 mm, among other lengths that can define an amount and/or degree of curvature that are possible and contemplated herein.

In some embodiments, the set of cutting teeth 314 on the distal end may define a cutting tip 320 that can initiate an osteotomy. Further, the cutting burrs 312 positioned along the single-plane slope 318 may define a cutting slope 318 that can perform the osteotomy to produce a wedge-shaped cut. In various embodiments, the coordination of the cutting tip 320 and the cutting slope 318 can allow the surgical instrument 300 to produce a wedge-shaped osteotomy in a single cut and/or single pass.

As further shown, the proximal end 310 includes an attachment mechanism 316 positioned thereon. The attachment mechanism 316 may include any suitable size dimensions, shape, and/or configuration that enables attachments of the surgical instrument 300 to another surgical instrument (not shown). That is, while the attachment mechanism 316 is shown as including particular relative size dimensions, shapes, and configurations, the various embodiments of the surgical instrument 300 are not limited to the illustrated attachment mechanism 316. That is, other embodiments of the surgical instrument 300 may include one or more different relative size dimension(s), shapes, and/or configurations.

FIGS. 4A through 4J are diagrams illustrating embodiments of a surgical instrument 400. At least in the illustrated embodiment, the surgical instrument 400 includes a double-sided device for cutting bone and/or tissue (e.g., a cutting device) and/or a multi-sided (e.g., two or more sided) a cutting device. While the description below refers to the surgical instrument 400 as a double-sided cutting device, the below description(s) apply equally to the various embodiments of the surgical instrument 400 that include(s) more than two sides (e.g., three (3) or more sided cutting devices).

A surgical instrument 400 may be constructed of any suitable material that can cut bone. In various embodiments, the surgical instrument 400 is constructed of a sterilized suitable material that can cut bone. In some embodiments, the surgical instrument 400 includes stainless steel, carbon steel, aluminum, and titanium, among other suitable materials and combinations of materials that are possible and contemplated herein. In additional or alternative embodiments, the surgical instrument 400 includes surgical grade stainless steel, among other suitable surgical grade materials and combinations of materials that are possible and contemplated herein.

In various embodiments, the surgical instrument 400 forms at least a portion of a cutting blade and/or cutting device. In some embodiments, the surgical instrument 400 forms at least a portion of a sagittal blade and/or sagittal saw, among other cutting blades and/or cutting devices that are possible and contemplated herein.

At least in the embodiments illustrated in FIGS. 4A through 4H, the surgical instrument 400 includes, among other features, a body 402 including at least a first surface 404 (e.g., first surfaces 404A through 404G in FIGS. 4A, 4C, 4E, 4F, 4G, 4H, and 4I, respectively), a second surface 406 (e.g., second surfaces 406A through 406G in FIGS. 4B, 4D, 4E, 4F, 4G, 4H, and 4J, respectively), a distal end 408, and a proximal end 410. A surgical instrument 400 further includes, among other features and/or elements, a set of cutting burrs 412A is positioned on the first surface 404, a set of cutting burrs 412B positioned on the second surface 406, a set of cutting teeth 414 positioned on the distal end 408, and an attachment mechanism 416 positioned on the proximal end 410.

A body 402 may include any suitable dimensions that can perform an osteotomy. In the illustrated embodiments, the body 402 includes a length L4, a width W7 at the distal end 408, and a width W8 at the proximal end 410 (see, FIGS. 4C and 4D) similar to the length L1, width W1, and a width W2 discussed above with reference to the various embodiments of the surgical instrument 100. In some embodiments, the width W7 and the width W8 are the same width or substantially the same width. In other embodiments, the width W7 is greater than the width W8 such that the proximal end 410 is wider than the distal end 408 or, alternatively, the distal end 408 is narrower than the proximal end 410 (e.g., the width W7 is less than the width W8). That is, in various embodiments, the surgical instrument 400 includes a tapered shape and/or tapers from the distal end 408 to the proximal end 410.

In the various illustrated embodiments, the first surface 404 includes a set of cutting burrs 412A positioned thereon. The set of cutting burrs 412A may be positioned on the first surface 404 in a non-patterned configuration (see, e.g., first surfaces 404A and 404B in FIGS. 4A and 4C, respectively) or one or more patterned configurations (see, e.g., first surface 404G in FIG. 4I). A non-patterned configuration may include any suitable pre-determined/planned distribution and/or random distribution of cutting burrs 412A that can assist in and/or facilitate performing an osteotomy and particularly, a wedge-shaped osteotomy, straight-cut osteotomy, and/or parallel-cut osteotomy. A patterned configuration may include any suitable pattern of cutting burrs 412A that is known or developed in the future that can assist in and/or facilitate performing an osteotomy and particularly, a wedge-shaped osteotomy, straight-cut osteotomy, and/or parallel-cut osteotomy, as described elsewhere herein.

A set of cutting burrs 412A may include any suitable quantity of cutting burrs 412A that can facilitate and/or assist the surgical instrument 400 in performing an osteotomy (e.g., a wedge-shaped osteotomy, straight-cut osteotomy, and/or parallel-cut osteotomy). In various embodiments, the first surface 404 includes a suitable quantity of cutting burrs 412A that can allow and/or enable the surgical instrument 400 to perform a wedge-shaped, straight-cut osteotomy, and/or parallel-cut osteotomy in one cut and/or one pass.

In various embodiments, the first surface 404 includes a quantity of cutting burrs 412B in the range of about three (3) cutting burrs 412A to about four thousand (4000) cutting burrs 412A, among other ranges of quantities of cutting burrs 412A and/or quantities of cutting burrs 412A less than 3 cutting burrs 412A or greater than 4000 cutting burrs 412A that are possible and contemplated herein. In some embodiments, the first surface 404 includes fifty (50) cutting burrs 412A, among other quantities of cutting burrs 412A that are possible and contemplated herein.

As further illustrated, the second surface 406 (e.g., opposite the first surface 404) includes a set of cutting burrs 412B positioned thereon. The set of cutting burrs 412B may be positioned on the second surface 406 in a patterned configuration or a non-patterned configuration similar to the set of cutting burrs 412A positioned on the first surface 404.

In various embodiments, the set of cutting burrs 412B on the second surface 406 include the same pattern and/or the same non-pattern as the set of cutting burrs 412A positioned on the first surface 404. In other embodiments, the set of cutting burrs 412B on the second surface 406 include a different pattern and/or a different non-pattern than the set of cutting burrs 412A positioned on the first surface 404. In further embodiments, the set of cutting burrs 412A on the first surface 404 include a pattern and the set of cutting burrs 412B on the second surface 406 are non-patterned or vice versa.

A set of cutting burrs 412B may include any suitable quantity of cutting burrs 412B that can facilitate and/or assist the surgical instrument 400 in performing an osteotomy and particularly, a wedge-shaped osteotomy, straight-cut osteotomy, and/or parallel-cut osteotomy. In various embodiments, the second surface 406 includes a suitable quantity of cutting burrs 412B that can allow and/or enable the surgical instrument 400 to perform a wedge-shaped, straight-cut osteotomy, and/or parallel-cut osteotomy in one cut and/or one pass.

In various embodiments, the second surface 406 includes a quantity of cutting burrs 412B in the range of about 3 cutting burrs 412 to about 4000 cutting burrs 412B, among other ranges of quantities of cutting burrs 412B and/or quantities of cutting burrs 412B that are possible and contemplated herein. In some embodiments, the second surface 406 includes 50 cutting burrs 412B, among other quantities of cutting burrs 412B that are possible and contemplated herein.

In various embodiments, the first surface 404 and the second surface 406 include the same quantity of cutting burrs 412A and 412B, respectively. In other embodiments, the first surface 404 and the second surface 406 include a different quantity of cutting burrs 412A and 412B, respectively. Here, the first surface 404 may include a greater quantity of cutting burrs 412A than the quantity of cutting burrs 412B included on the second surface 406 or vice versa.

While the surgical instrument 400 is shown with a first surface 404 including a specific quantity of cutting burrs 412B and a second surface 406 including a specific quantity of cutting burrs 412B, the various embodiments of the surgical instrument 400 are not limited to the illustrated quantity of cutting burrs 412A and 41B. That is, various other embodiments of a surgical instrument 400 can include a different quantity of cutting burrs 412A on the first surface 404 (e.g., a greater quantity or smaller quantity) and a different quantity of cutting burrs 412B on the second surface 406 (e.g., a greater quantity or smaller quantity), a different quantity of cutting burrs 412A on the first surface 404 (e.g., a greater quantity or smaller quantity) and the same quantity of cutting burrs 412B on the second surface 406, or the same quantity of cutting burrs 412A on the first surface 404 and a different quantity of cutting burrs 412B on the second surface 406 (e.g., a greater quantity or smaller quantity) than the illustrated quantities of cutting burrs 412A and 412B.

In various embodiments, the cutting burrs 412A may be included on the entirety or substantially the entirety of a first surface 404 (see, e.g., first surfaces 404A, 404B, 404C, 404E, and 404G in FIGS. 4A, 4C, 4E, 4G, and 4I, respectively) and the cutting burrs 412B may be included on the entirety or substantially the entirety of the second surface 406 (see, e.g., 406A, 406B, 406C, 406E, and 406G in FIGS. 4B, 4D, 4G, 4H, and 4J, respectively). In various other embodiments, the cutting burrs 412A may be included on a portion of a first surface 404 (see, e.g., first surfaces 404D and 404F in FIGS. 4F and 4H, respectively) and the cutting burrs 412B may be included on a portion of a second surface 406 (see, e.g., second surfaces 406D and 406F in FIGS. 4F and 4H, respectively). In other embodiments, the cutting burrs 412A may be included on the entirety or substantially the entirety of a first surface 404 (see, e.g., first surfaces 404A, 404B, 404C, 404E, and 404G in FIGS. 4A, 4C, 4E, 4G, and 4I, respectively) and the cutting burrs 412B may be included on a portion of a second surface 404 (see, e.g., second surfaces 406D and 406F in FIGS. 4F and 4H, respectively). In still other embodiments, the cutting burrs 412A may be included on a portion of a first surface 404 (see, e.g., first surfaces 404D and 404F in FIGS. 4F and 4H, respectively) and the cutting burrs 412B may be included on the entirety or substantially the entirety of the second surface 406 (see, e.g., 406A, 406B, 406C, 406E, and 406G in FIGS. 4B, 4D, 4G, 4H, and 4J, respectively).

The portion of the first surface 404D, 404F including the cutting burrs 412A and/or the portion of the second surface 406D, 406F including the cutting burrs 412B may include any suitable sized portion that can produce a wedge-shaped osteotomy, straight-cut osteotomy, and/or parallel-cut osteotomy. Various embodiments of the surgical instrument 400 may include varying sized portions of the first surface 404D, 404F and/or the second surface 406D, 406F including the cutting burrs 412A and/or 412B, respectively, so that different sized and/or wedge-shaped osteotomies, straight-cut osteotomies, and/or parallel-cut osteotomies can be obtained.

In some embodiments, the portion of the first surface 404D, 404F including the cutting burrs 412A and the portion of the second surface 406D, 406F including the cutting burrs 412B include the same sized portions. In other embodiments, the portion of the first surface 404D, 404F including the cutting burrs 412A and the portion of the second surface 406D, 406F including the cutting burrs 412B include different sized portions. In various embodiments, the portion of the first surface 404D, 404F including the cutting burrs 412A is greater in size than the portion of the second surface 406D, 406F including the cutting burrs 412B or vice versa.

A cutting burr 412A and/or 412B (also referred to herein, individually and/or collectively, as cutting burr(s) 412) may include any suitable shape that can facilitate and/or assist the surgical instrument 400 in performing an osteotomy (e.g., a wedge-shaped osteotomy, straight-cut osteotomy, and/or parallel-cut osteotomy). In various embodiments, a cutting burr 412 can include a diamond shape, a pointed shape (e.g., a shape that comes to a sharp point), a flame shape, a bullet shape, a cone shape, a tapered shape, or an egg shape, among other suitable shapes that can facilitate cutting bone that are possible and contemplated herein. In additional or alternative embodiments, a cutting burr 412 may be considered the same as or similar to a cutting tooth and/or cutting teeth.

In some embodiments, all of the cutting burrs 412A on the first surface 404 include the same or substantially the same shape. In alternative embodiments, at least two cutting burrs 412A on the first surface 404 include different shapes or substantially different shapes.

In certain embodiments, all of the cutting burrs 412B on the second surface 406 include the same or substantially the same shape. In alternative embodiments, at least two cutting burrs 412B on the second surface 406 include different shapes or substantially different shapes.

In further embodiments, the cutting burrs 412A on the first surface 404 and the cutting burrs 412B on the second surface 406 include the same or substantially the same shape. In alternative embodiments, at least one cutting burr 412A on the first surface 404 includes a different shape than at least one cutting burr 412B on the second surface 406.

A cutting burr 412 may include any suitable height that can facilitate and/or assist the surgical instrument 400 in performing an osteotomy (e.g., a wedge-shaped osteotomy, straight-cut osteotomy, and/or parallel-cut osteotomy, etc.). In various embodiments, a cutting burr 412 can include a height in the range of about 0.1 mm to about 30 mm, among other suitable heights that can facilitate cutting bone that are possible and contemplated herein. In some embodiments, a cutting burr 412 includes a height of 0.75 mm.

In various embodiments, all of the cutting burrs 412A in the set of cutting burrs 412A on the first surface 404 can include the same or substantially the same height (see, e.g., FIGS. 4A, 4B, 4E, 4F, and 4I). In alternative embodiments, at least two cutting burrs 412A in the set of cutting burrs 412A on the first surface 404 include different heights or substantially different heights (see, e.g., FIGS. 4G and 4H).

In additional or alternative embodiments, all of the cutting burrs 412B in the set of cutting burrs 412B on the second surface 406 can include the same or substantially the same height (see, e.g., FIGS. 4A, 4B, 4E, 4F, and 4I). In alternative embodiments, at least two cutting burrs 412B in the set of cutting burrs 412B on the second surface 406 include different heights or substantially different heights (see, FIGS. 4G and 4H).

In further additional or alternative embodiments, each of the cutting burrs 412A in the set of cutting burrs 412A on the first surface 404 include the same or substantially the same height as each of the cutting burrs 412B in the set of cutting burrs 412B on the second surface 406 (see, e.g., FIGS. 4A, 4B, 4E, 4F, and 4I). In other additional or alternative embodiments, at least one cutting burr 412A on the first surface 404 includes a different height than at least one cutting burr 412B on the second surface (see, e.g., FIGS. 4G and 4H).

Figure 4A:
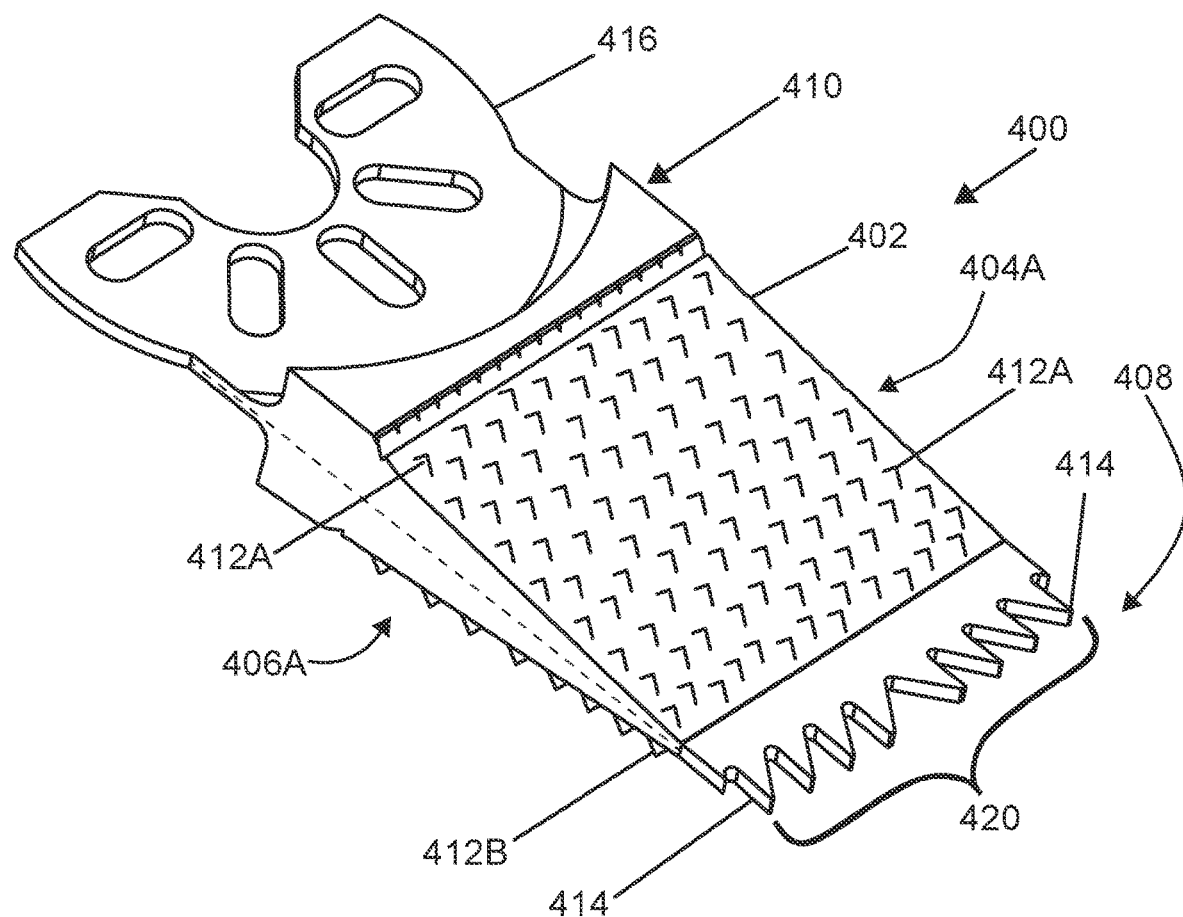
FIGS. 4A through 4J are schematic diagrams illustrating various embodiments of a double-sided surgical instrument including cutting burrs.
Figure 4B:
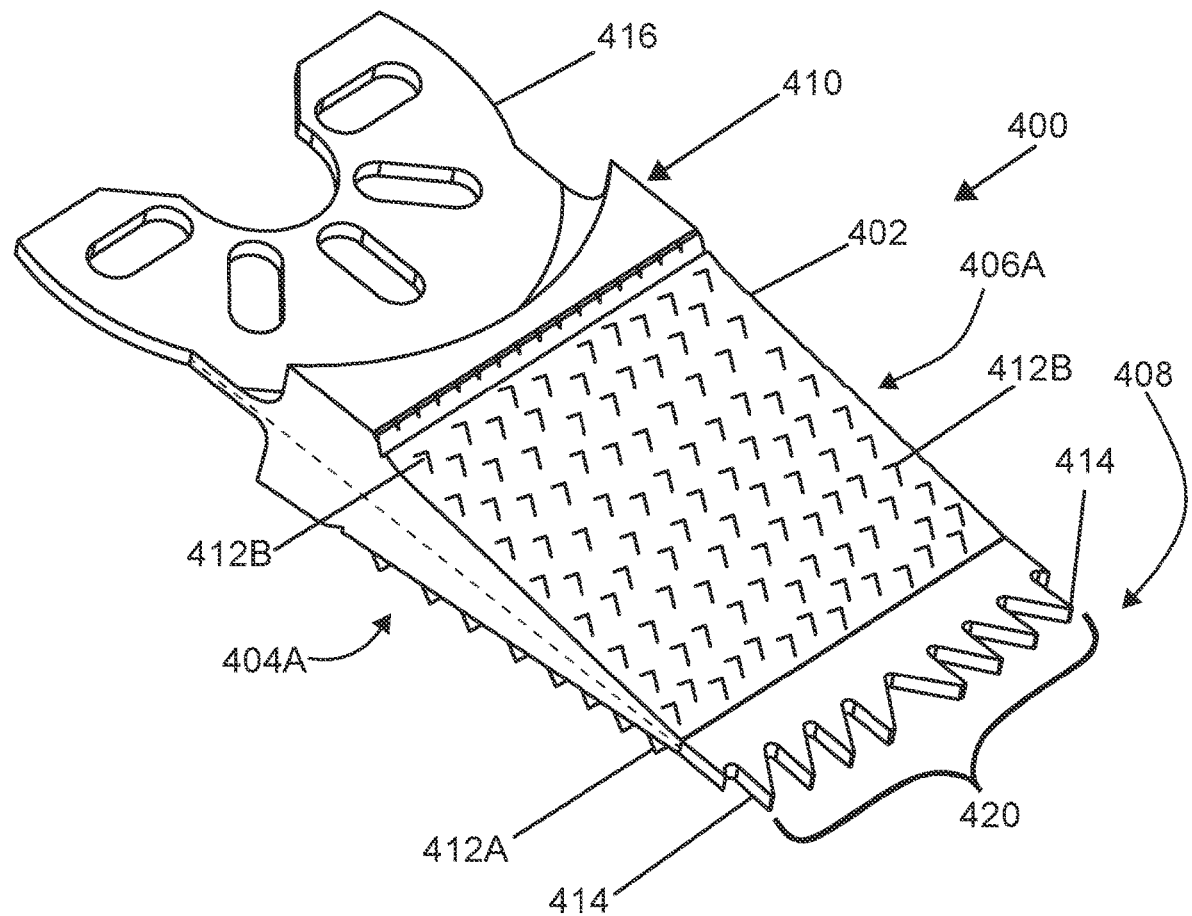
Figure 4C:
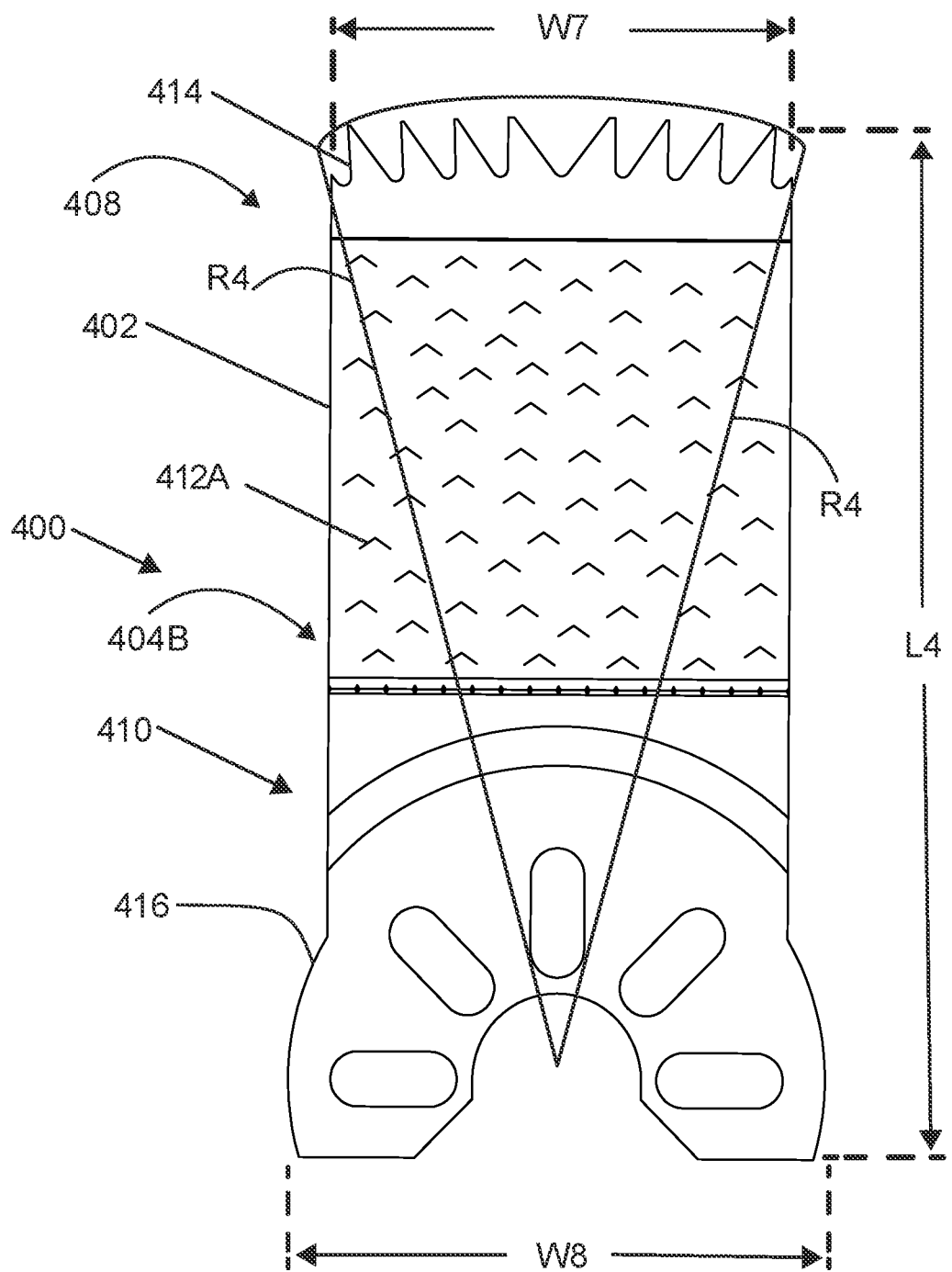
Figure 4D:
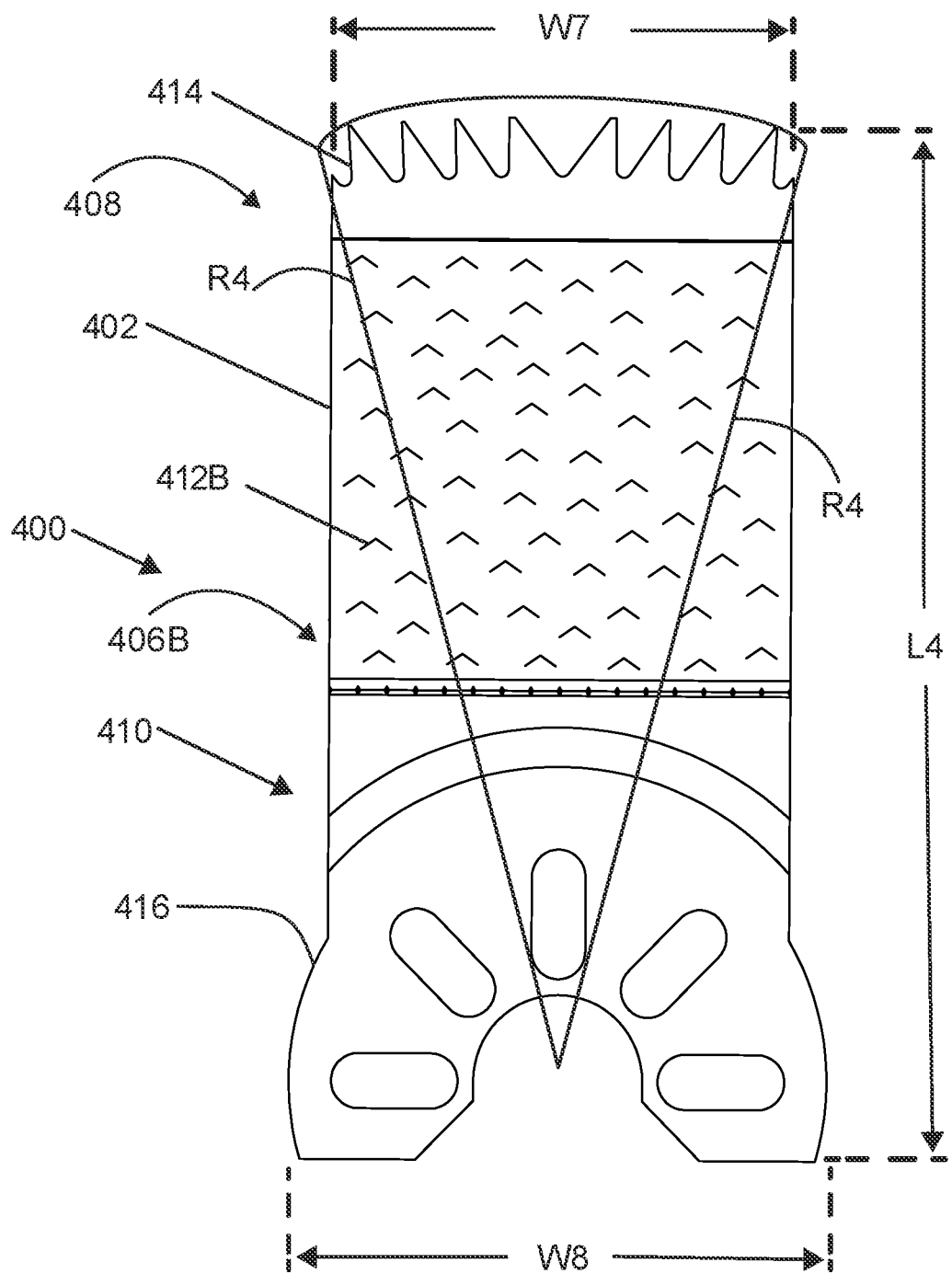
Figure 4E:
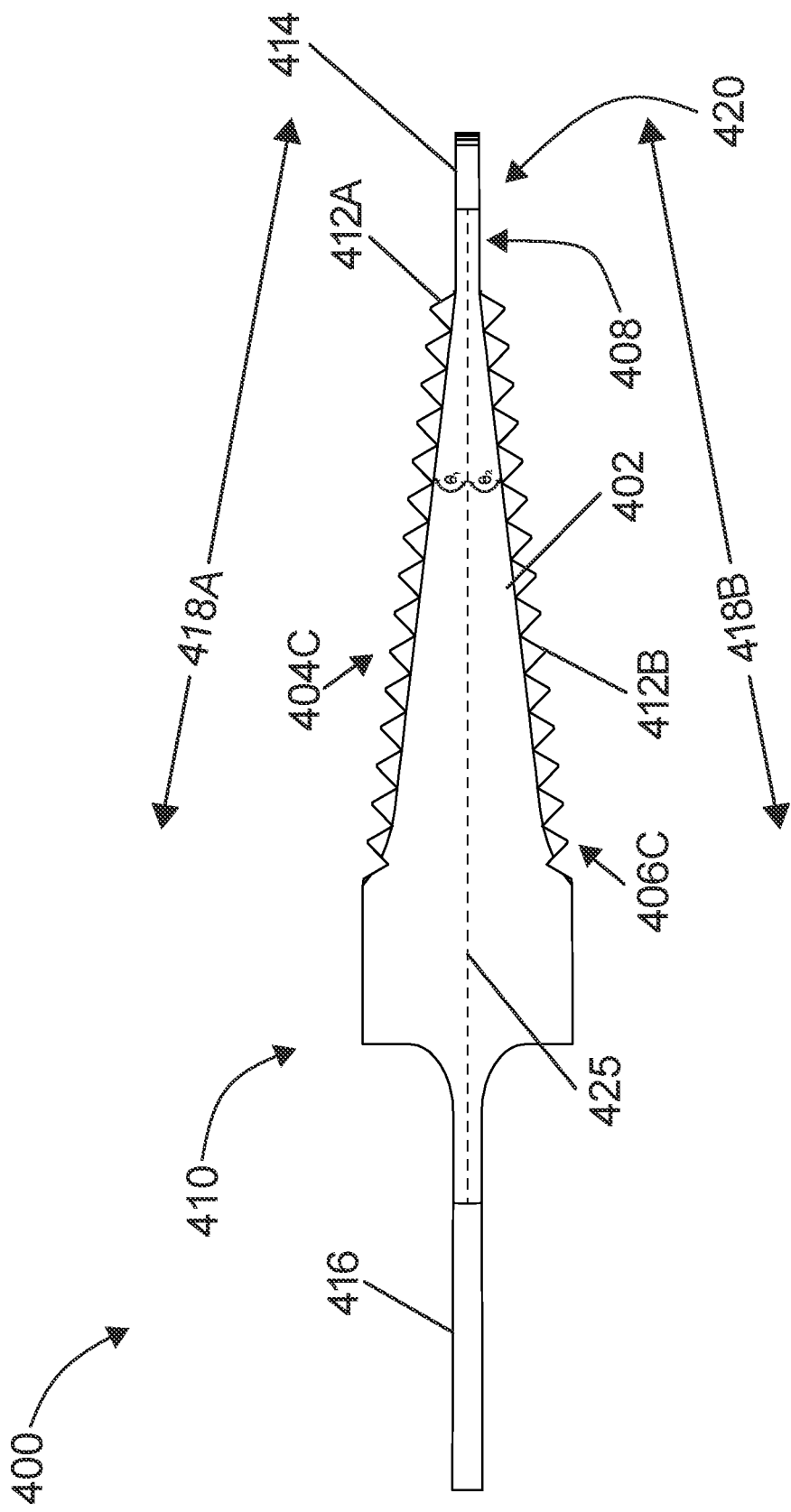
Figure 4F:
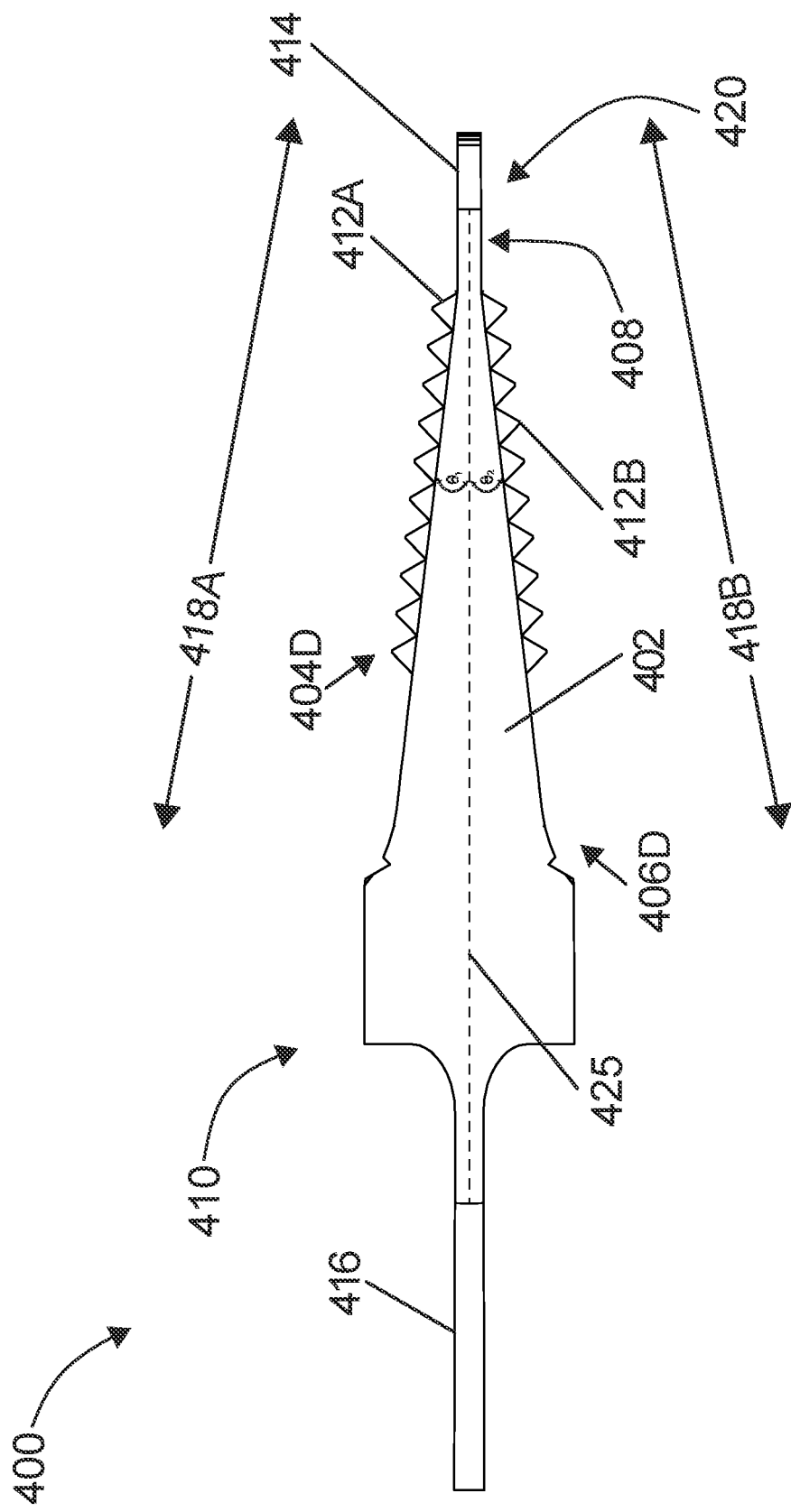
Figure 4G:
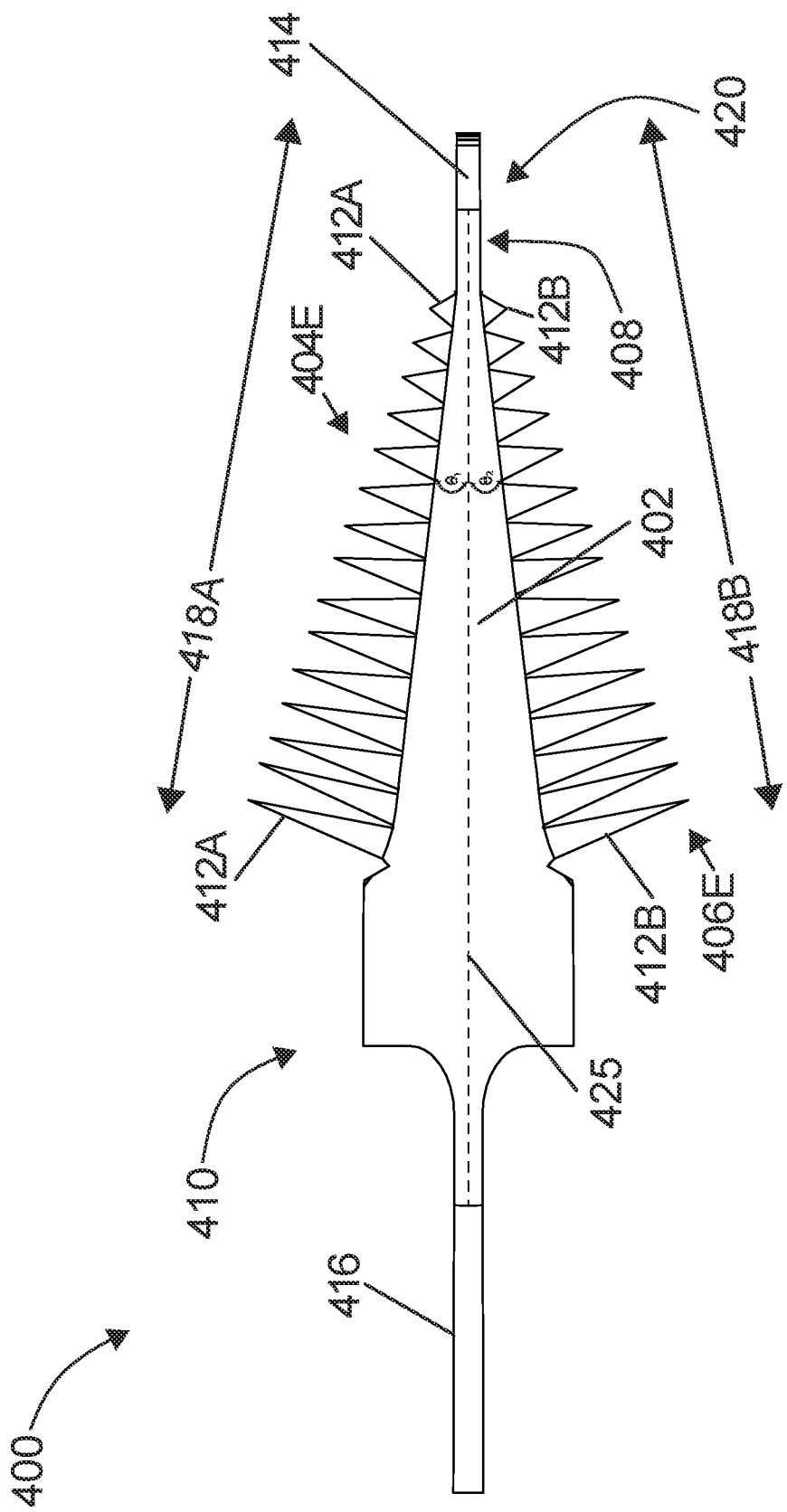
Figure 4H:
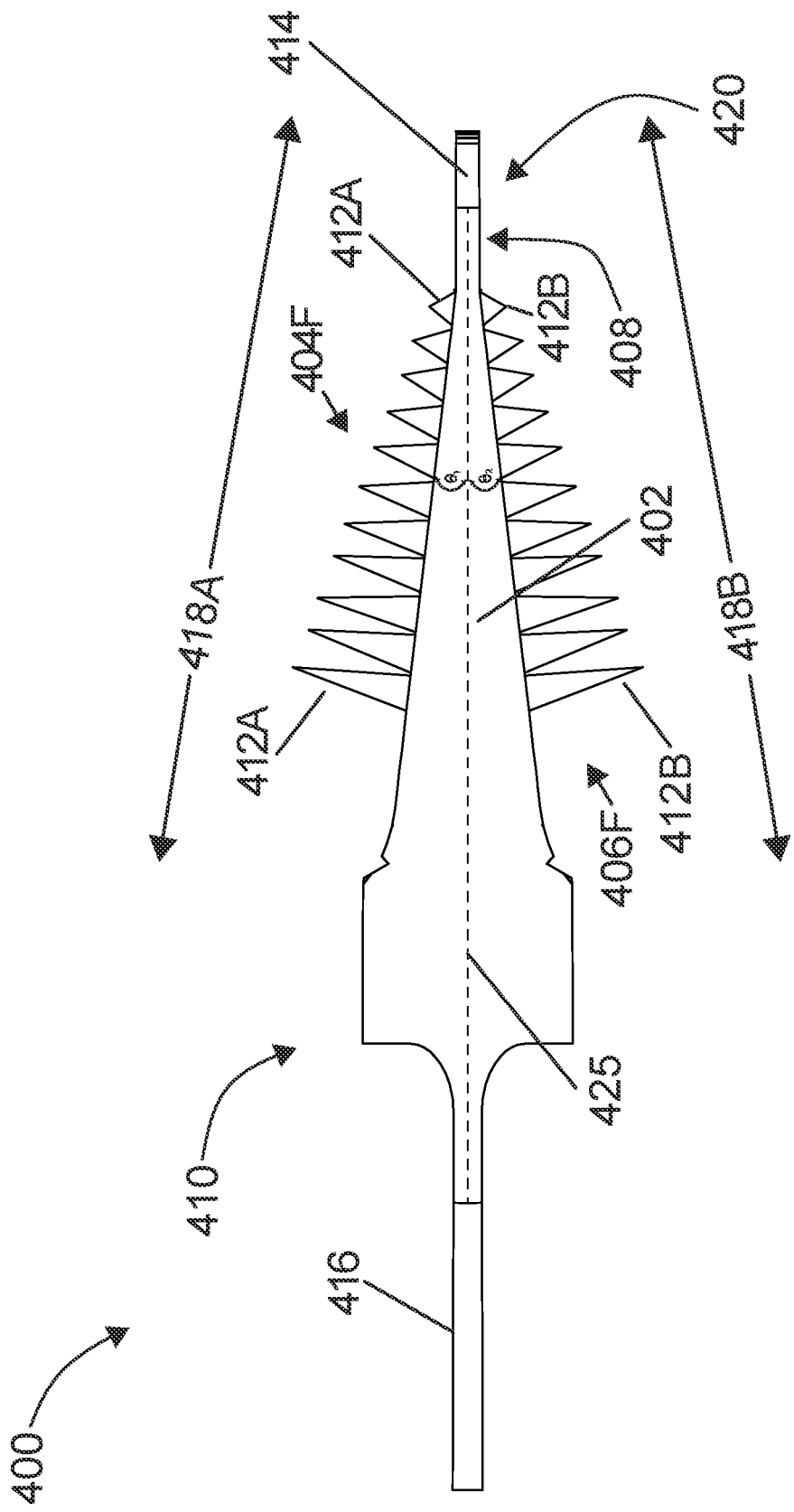

In alternative embodiments, each of the cutting burrs 412A in the set of cutting burrs 412A on the first surface 404 include the same height or substantially the same height (see. e.g., FIGS. 4A, 4B, 4E, 4F, and 4I) and at least two cutting burrs 412B in the set of cutting burrs 412B on the second surface 406 include different heights (see, e.g., FIGS. 4G and 4H). In other alternative embodiments, at least two of the cutting burrs 412A in the set of cutting burrs 412A on the first surface 404 include different heights (see, e.g., FIGS. 4G and 4H) and each of the cutting burrs 412B in the set of cutting burrs 412B on the second surface 406 include the same height or substantially the same height (see. e.g., FIGS. 4A, 4B, 4E, 4F, and 4I).

In certain embodiments, the cutting burrs 412 including the greater height(s) on the first surface 404E, 404F and/or second surface 406E, 406F may be grouped together at a position at or near the proximal end 410 (or away from the distal end 408) and the cutting burrs 412 including the smaller height(s) on the first surface 404E, 404F and/or second surface 406E, 406F may be positioned at the distal end 408 (or away from the proximal end 410) or vice versa. In additional embodiments, a greater quantity of the cutting burrs 412 including the smaller height(s) on the first surface 404E, 404F and/or second surface 406E, 406F may be grouped together at or near the distal end 408 than the quantity of the cutting burrs 412 including the taller height (s) on the first surface 404E, 404F and/or second surface 406E, 406F grouped together at or near the proximal end 410 (or away from the distal end 408) or vice versa and/or including the various possible combinations of quantities of shorter and/or taller cutting burrs 412 on the distal end 408 and/or proximal end 410 and/or the first surface 404 and/or the second surface 406 that are possible, each of which is contemplated herein.

A first surface 404 may include any suitable profile upon which a set of cutting burrs 412A can be positioned. In various embodiments, the first surface 404 includes a slope 418A that extends upward and/or away from a reference plane 425 (e.g., a flat (e.g., a 0° angle) reference plane between the first surface 404 and the second surface 406) and the distal end 408.

The slope 418A (see, e.g., FIGS. 4E, 4F, 4G, and 4H) may include any suitable grade (e.g., rise over run) with respect to the reference plane 425 that can facilitate and/or assist the surgical instrument 400 in performing an osteotomy and particularly, a wedge-shaped osteotomy, a straight-cut osteotomy, and/or a parallel-cut osteotomy. That is, the first surface 404 and/or surgical instrument 400 may include any suitable grade that can facilitate and/or assist the surgical instrument 400 in performing a wedge-shaped osteotomy, straight-cut osteotomy, and/or parallel-cut osteotomy in one cut and/or one pass.

In various embodiments, the slope 418A includes a grade in the range of about zero degrees (0° or flat) to about fifteen degrees (15°) with respect to the reference plane 425, among other ranges of grades, specific grades, and/or slopes that are possible and contemplated herein. In other words, an angle $\theta_1$ in the range of about 0° to about 45° (e.g., the angle $\theta_1$=0°, 1°, 2°, 3°, 4°, 5°, 6°, 7°, 8°, 9°, 40°, 41°, 42°, 43°, 44°, or 45° and/or the angle $\theta_1 \approx$0°, 1°, 2°, 3°, 4°, 5°, 6°, 7°, 8°, 9°, 40°, 41°, 42°, 43°, 44°, or 45°) is defined between the first surface 404 and the reference pane 425 beginning at the distal end 408 and extending upward and toward the proximal end 410, as shown in FIGS. 4E through 4H. In some embodiments, the slope 418A includes a grade of about seven degrees (7°) (e.g., the angle $\theta_1$=7° or the angle $\theta_1 \approx$7°), among other suitable grades and/or slopes that are possible and contemplated herein.

A second surface 406 may include any suitable profile upon which a set of cutting burrs 412B can be positioned. In various embodiments, the second surface 406 includes a slope 418B (see, e.g., FIGS. 4E, 4F, 4G, and 4H) that extends upward and/or away from the reference plane 425 and the distal end 408. The slope 418B may include any suitable grade (e.g., rise over run) that can facilitate and/or assist the surgical instrument 400 in performing an osteotomy and particularly, a wedge-shaped osteotomy, straight-cut osteotomy, and/or parallel-cut osteotomy. That is, the second surface 406 and/or surgical instrument 400 may include any suitable grade that can facilitate and/or assist the surgical instrument 400 in performing a wedge-shaped osteotomy, straight-cut osteotomy, and/or parallel-cut osteotomy in one cut and/or one pass.

In various embodiments, the slope 418B includes a grade in the range of about zero degrees (0° or flat) to about fifteen degrees (15°), among other ranges of grades, grades, and/or slopes that are possible and contemplated herein. In other words, an angle $\theta_2$ in the range of about 0° to about 45° (e.g., the angle $\theta$=0°, 1°, 2°, 3°, 4°, 5°, 6°, 7°, 8°, 9°, 40°, 41°, 42°, 43°, 44°, or 45° and/or the angle $\theta \approx$0°, 1°, 2°, 3°, 4°, 5°, 6°, 7°, 8°, 9°, 40°, 41°, 42°, 43°, 44°, or) 45° is defined between the second surface 406 and the reference plane 425 beginning at the distal end 408 and extending upward and toward the proximal end 410, as shown in FIGS. 4E through 4H. In some embodiments, the slope 418B includes a grade of about 7 degrees (e.g., the angle $\theta_2$=7° or the angle $\theta_2 \approx$7°), among other suitable grades and/or slopes that are possible and contemplated herein.

In various embodiments, the angles $\theta_1$ and $\theta_2$ include the same angle with respect to the reference plane 425. In alternative embodiments, the angles $\theta_1$ and $\theta_2$ include different angles with respect to the reference plane 425. In certain embodiments, the angle $\theta_1$ is greater than the angle $\theta_2$ or vice versa.

In some embodiments, the angles $\theta_1$ and $\theta_2$ are each greater than 0° such that neither of slopes 418A and 418B define a flat surface for the first surface 404 and the second surface 406 (e.g., the first surface 404 and the second surface 406 are not parallel to the reference plane 425). Here, the angles $\theta_1$ and $\theta_2$ can include the same angle greater than 0° or different angles greater than 0° with respect to the reference plane 425.

In other embodiments, angle $\theta_1$ and $\theta_2$ are each 0°. Here, the slope 418A defines a flat surface for the first surface 404 and the slope 418B defines a flat surface of the second surface 406 (e.g., first surface 404 and second surface 406 are parallel to the reference plane 425).

In still other embodiments, angle $\theta_1$ or angle $\theta_2$ is 0° and the other one of angle $\theta_1$ or angle $\theta_2$ greater than 0° with respect to the reference angle 425. Here, the slope 418A for the first surface 404 or the slope 418B for the second surface 406 defines a non-flat or sloped surface for the first surface 404 or second surface 406, respectively, with respect to the reference angle 425 and the other one of the first surface 404 or the second surface 406 includes a flat surface (e.g., is parallel to the reference angle 425).

Figure 4I:
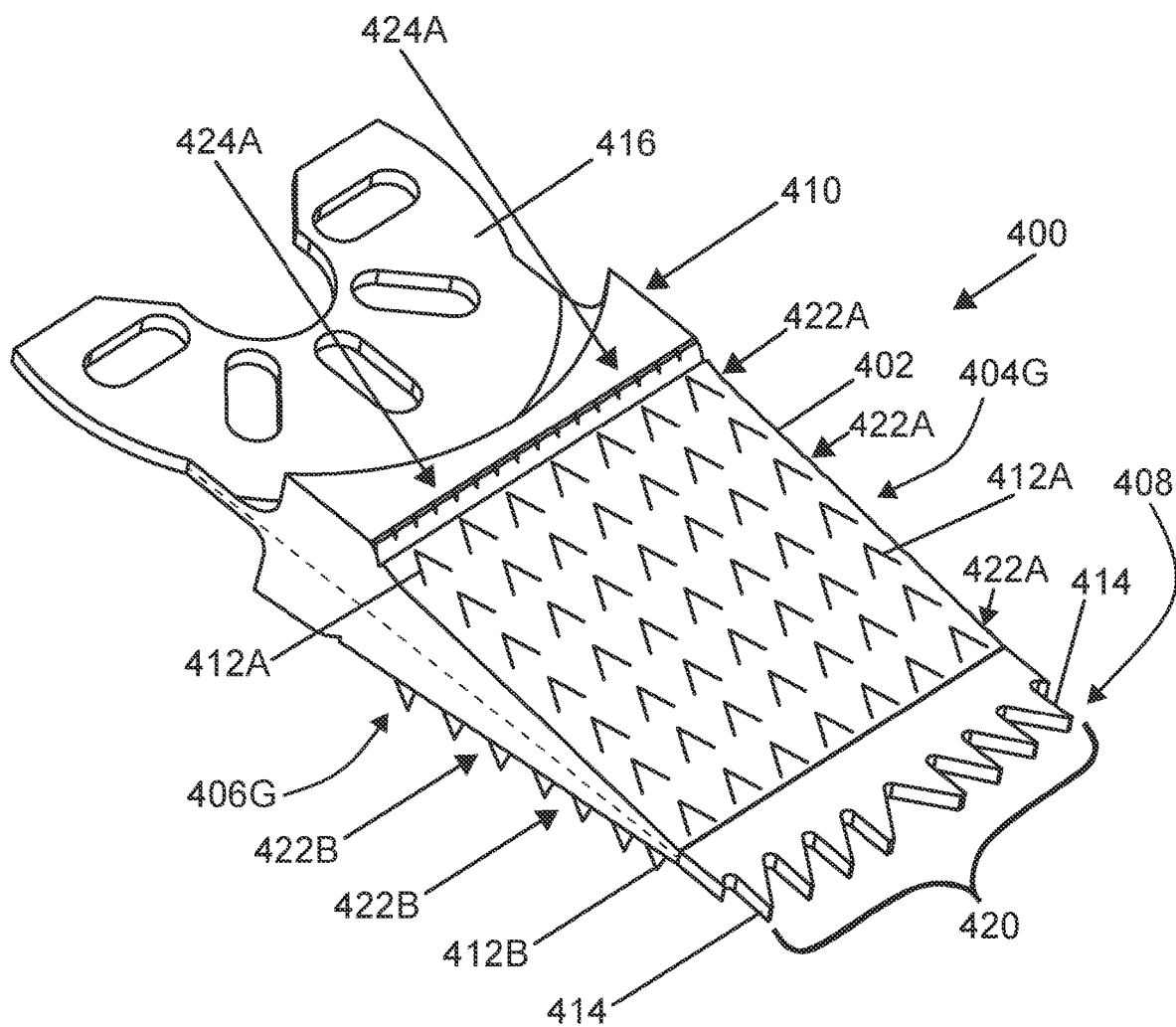

With reference to FIG. 4I, in some embodiments, the cutting burrs 412A may be positioned on the first surface 404G in one or more rows 422A, which can include any suitable quantity of rows 422A. In other embodiments, the cutting burrs 412A may be positioned on the first surface 404G in one or more columns 424A, which can include any suitable quantity of columns 424A.

In further embodiments, the cutting burrs 412A may be positioned on the first surface 404G in one or more rows 422A and one or more columns 424A, which can include any suitable quantity of rows 422A and/or any suitable quantity of columns 424A. In some embodiments, the first surface 404G includes the same quantity of rows 422A and columns 424A. In other embodiments, the first surface 404G includes a different quantity of rows 422A and columns

424A. That is, the first surface 404G may include a greater quantity or smaller quantity of rows 422A than columns 424A or vice versa.

Figure 4J:
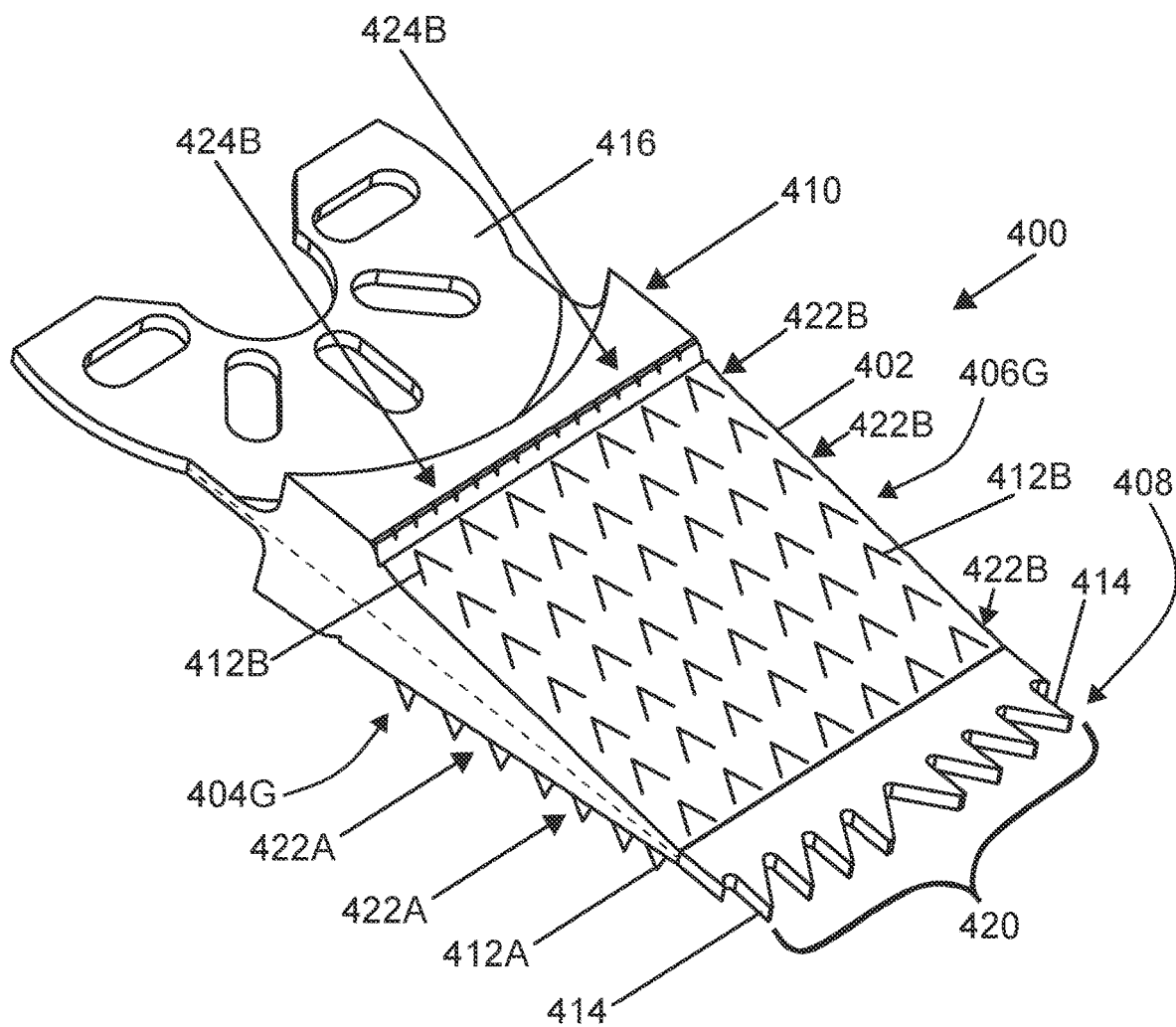

Referring to FIG. 4J, in some embodiments, the cutting burrs 412B may be positioned on the second surface 406G in one or more rows 422B, which can include any suitable quantity of rows 422B. In other embodiments, the cutting burrs 412B may be positioned on the second surface 406G in one or more columns 424B, which can include any suitable quantity of columns 424B.

In further embodiments, the cutting burrs 412B may be positioned on the second surface 406G in one or more rows 422B and one or more columns 424B, which can include any suitable quantity of rows 422B and/or any suitable quantity of columns 424B. In some embodiments, the second surface 406G includes the same quantity of rows 422B and columns 424B. In other embodiments, the second surface 406G includes a different quantity of rows 422B and columns 424B. That is, the second surface 406G may include a greater quantity or smaller quantity of rows 422B than columns 424B or vice versa.

In various embodiments, the first surface 404G and the second surface 406G each include one or more rows 422A and 422B, respectively. In some embodiments, the first surface 404G and the second surface 406G include the same quantity of rows 422A and 422B, respectively. In alternative embodiments, the first surface 404G and the second surface 406G include different quantities of rows 422A and 422B, respectively. In certain embodiments, the first surface 404G includes a greater quantity or a smaller quantity of rows 422A than the quantity of rows 422B on the second surface 406G or vice versa.

In various additional or alternative embodiments, the first surface 404G and the second surface 406G each include one or more columns 424A and 424B, respectively. In some embodiments, the first surface 404G and the second surface 406G include the same quantity of columns 424A and 424B, respectively. In alternative embodiments, the first surface 404G and the second surface 406G include different quantities of columns 424A and 424B, respectively. In certain embodiments, the first surface 404G includes a greater quantity or a smaller quantity of columns 424A than the quantity of columns 424B on the second surface 406G or vice versa.

In some embodiments, the first surface 404G includes one or more rows 422A of cutting burrs 412A, which can include any suitable quantity of rows 422A, and the second surface 406G includes one or more columns 424B of cutting burrs 412B, which can include any suitable quantity of columns 424B. The first surface 404G and the second surface 406G, in various embodiments, may include the same quantity of rows 422A and columns 424B, respectively. In other embodiments, the first surface 404G may include a greater quantity or a smaller quantity of rows 422A than the quantity of columns 424B on the second surface 406G or vice versa.

In alternative embodiments, the first surface 404G includes one or more columns 424A of cutting burrs 412A, which can include any suitable quantity of columns 424A, and the second surface 406G includes one or more rows 422B of cutting burrs 412B, which can include any suitable quantity of rows 422B. The first surface 404G and the second surface 406G, in various embodiments, may include the same quantity of columns 424A and rows 422B, respectively. In other embodiments, the first surface 404G may include a greater quantity or a smaller quantity of columns 424A than the quantity of rows 422B on the second surface 406G or vice versa.

As shown in the various embodiments illustrated in FIGS. 4A through 4J, the distal end 408 may include a set of cutting teeth 414 (e.g., a single tooth 414 or multiple teeth 414) positioned thereon, while other embodiments may not include a set of cutting teeth 414. A set of cutting teeth 414 may include any suitable quantity of teeth 414 that can assist in and/or facilitate initiating an osteotomy when oscillated and particularly, a wedge-shaped osteotomy.

In various embodiments, the set of cutting teeth 414 includes a quantity of cutting teeth 414 in the range of one (1) cutting tooth 414 to about 50 cutting teeth 414, among other ranges of quantities and/or quantities of cutting teeth 414 that are possible and contemplated herein. In some embodiments, a set of cutting teeth 414 includes about 8 cutting teeth 414, among other quantities of cutting teeth 414 that are possible and contemplated herein.

In some embodiments, the set of cutting teeth 414 is positioned on the distal end 410 in a straight line or substantially straight line. In other embodiments, the set of cutting teeth 414 is positioned along a curve on the distal end 410 defined by a radius R4.

The radius R4 (see, e.g., FIGS. 4C and 4D) may include any suitable radius and/or curvature that can assist in and/or facilitate initiating an osteotomy (e.g., a wedge-shaped osteotomy, straight-cut osteotomy, and/or parallel-cut osteotomy) when oscillated. In various embodiments, the radius R4 is in the range of about 5 mm to about 80 mm, among other ranges of lengths and/or lengths that can define an amount and/or degree of curvature that are possible and contemplated herein. In some embodiments, the radius R4 is about 25 mm, among other lengths that can define an amount and/or degree of curvature that are possible and contemplated herein.

In some embodiments, the set of cutting teeth 414 on the distal end may define a cutting tip 420 that can initiate an osteotomy. Further, the cutting burrs 412A and 412B positioned on the first surface 404 and second surface 406 can perform an osteotomy to produce a wedge-shaped cut, a straight cut, and/or a parallel cut. In various embodiments, the coordination of the cutting tip 420 and the cutting burrs 412 can allow the surgical instrument 400 to produce a large or larger wedge-shaped osteotomy, a large or larger straight cut, or combination of a wedge-shaped cut (e.g., smaller wedge cut) and a straight cut (e.g., a smaller straight cut) in a single cut and/or single pass.

As further shown, the proximal end 410 includes an attachment mechanism 416 positioned thereon. The attachment mechanism 416 may include any suitable size dimensions, shape, and/or configuration that enables attachments of the surgical instrument 400 to another surgical instrument (not shown). That is, while the attachment mechanism 416 is shown as including particular relative size dimensions, shapes, and configurations, the various embodiments of the surgical instrument 400 are not limited to the illustrated attachment mechanism 416. That is, other embodiments of the surgical instrument 400 may include one or more different relative size dimension(s), shapes, and/or configurations.

Figure 5A:
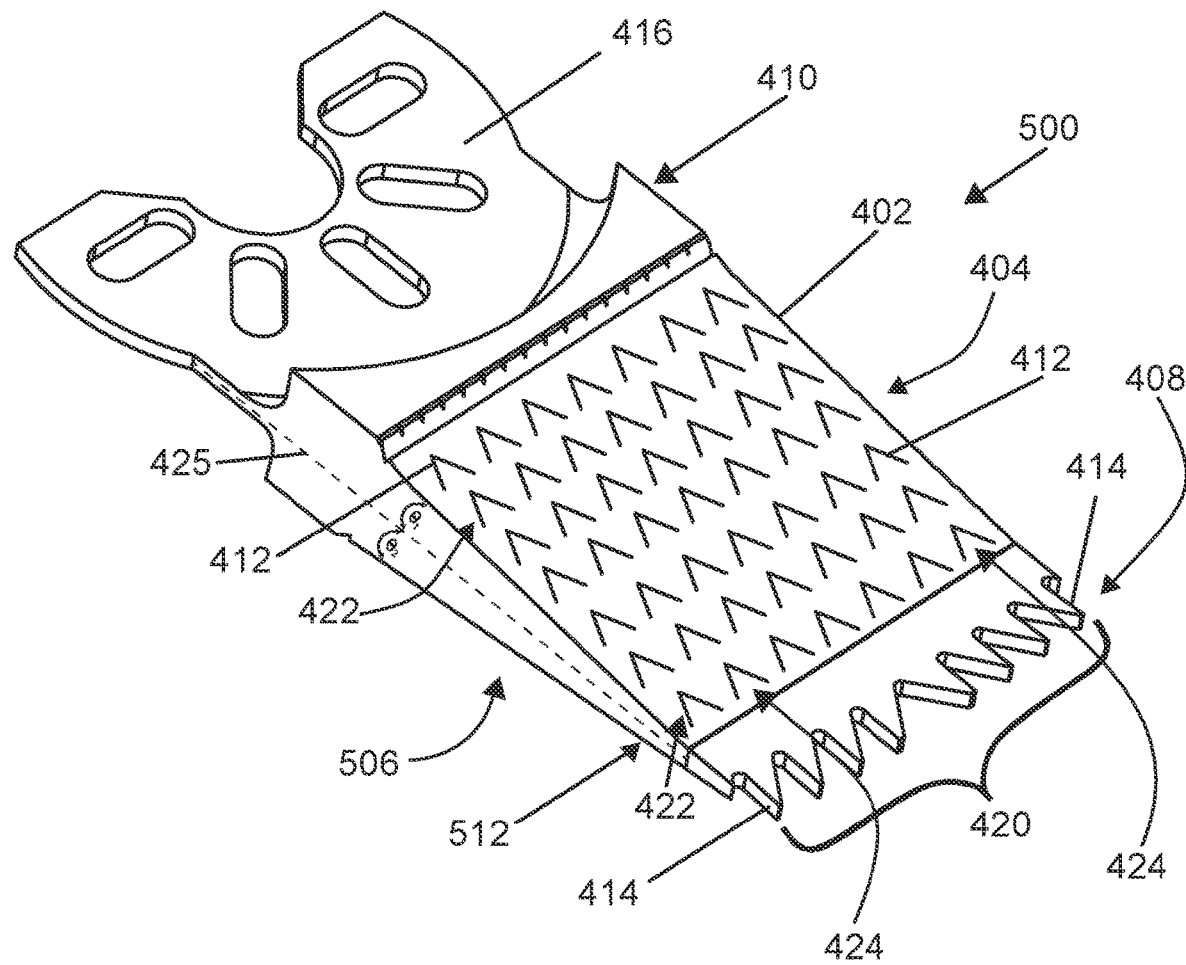
FIGS. 5A through 5C are schematic diagrams illustrating various embodiments of a double-sided surgical instrument including cutting burrs and columns of cutting blades.
Figure 5B:
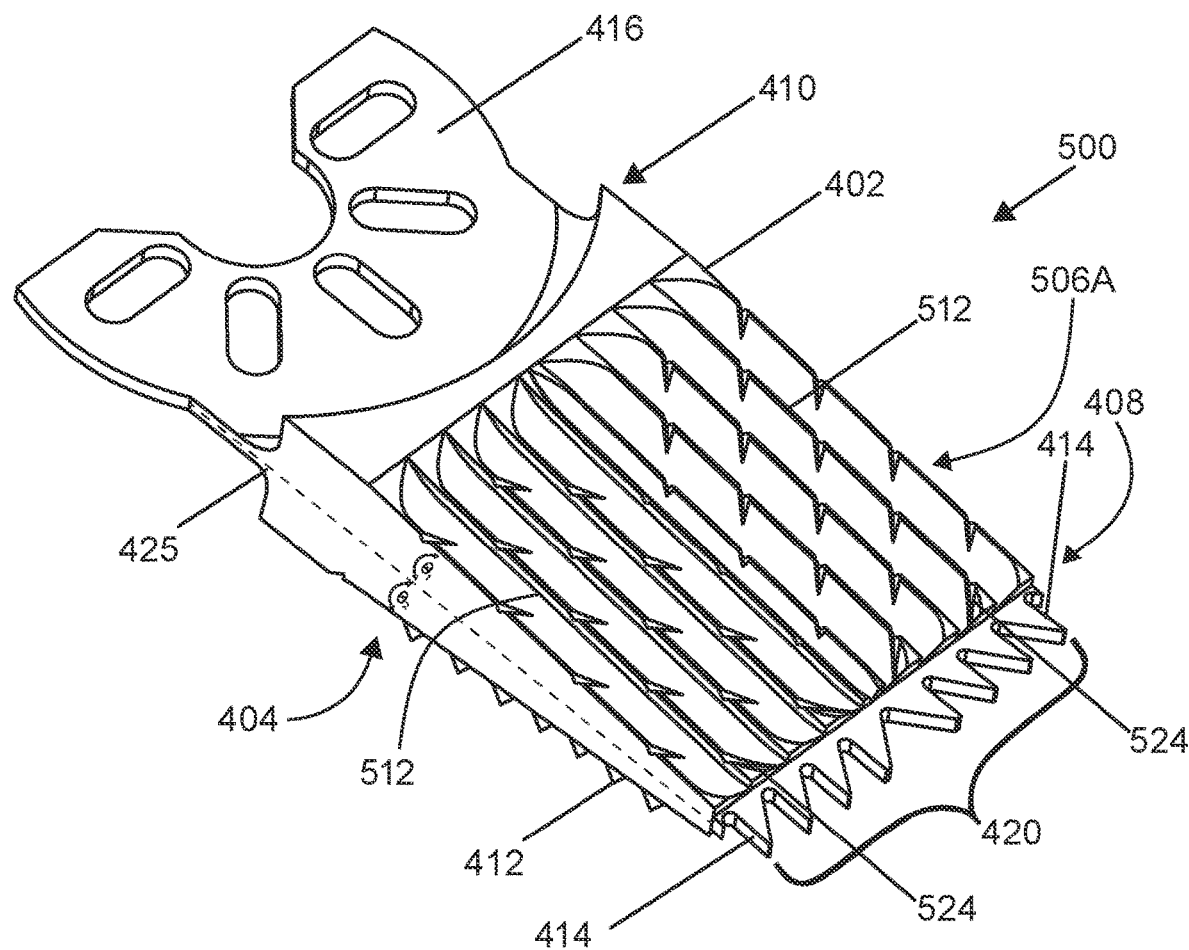
Figure 5C:
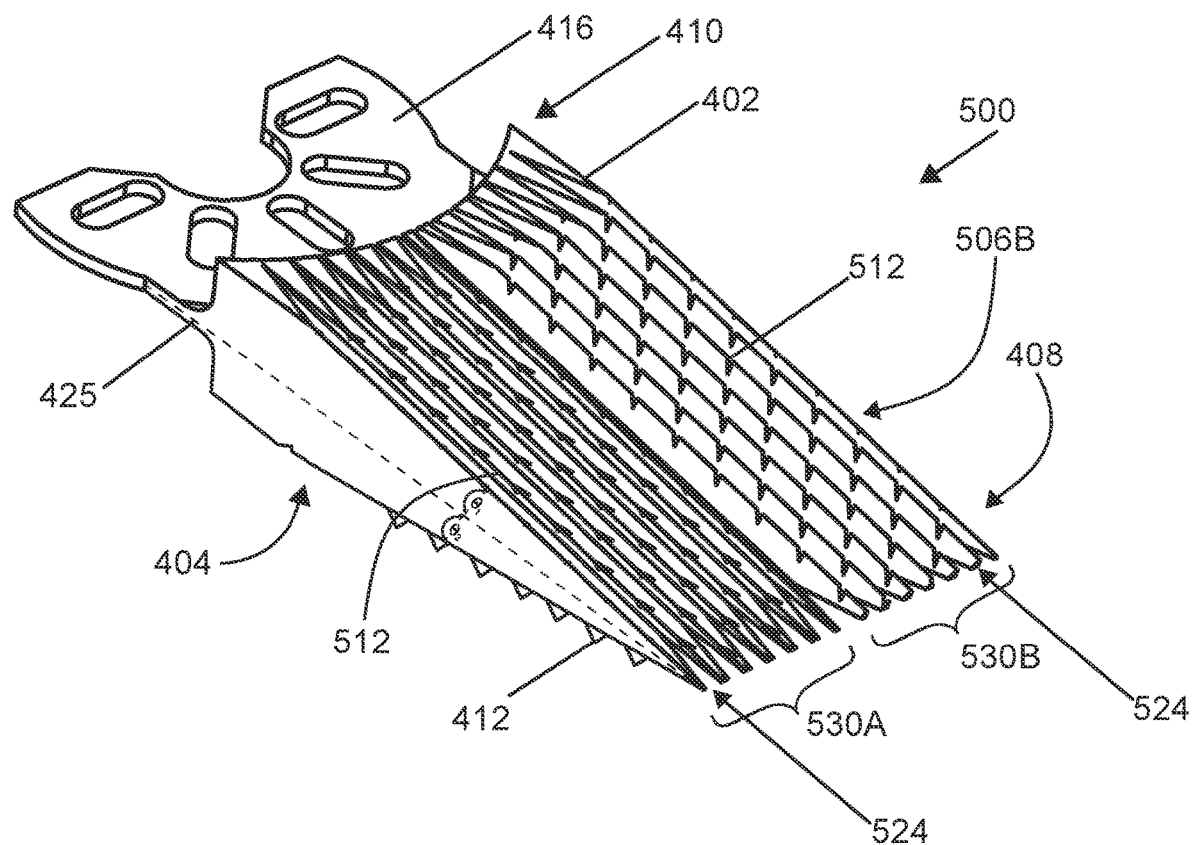

FIGS. 5A through 5C are diagrams illustrating embodiments of a surgical instrument 500. At least in the illustrated embodiment, the surgical instrument 500 includes a double-sided device for cutting bone and/or tissue (e.g., a cutting device) and/or a multi-sided (e.g., two or more sided) a cutting device. While the description below refers to the surgical instrument 500 as a double-sided cutting device, the below description(s) apply equally to the various embodiments of the surgical instrument 500 that include(s) more than two sides (e.g., three (3) or more sided cutting devices).

A surgical instrument 500 may be constructed of any suitable material that can cut bone. In various embodiments, the surgical instrument 500 is constructed of a sterilized suitable material that can cut bone. In some embodiments, the surgical instrument 500 includes stainless steel, carbon steel, aluminum, and titanium, among other suitable materials and combinations of materials that are possible and contemplated herein. In additional or alternative embodiments, the surgical instrument 500 includes surgical grade stainless steel, among other suitable surgical grade materials and combinations of materials that are possible and contemplated herein.

In various embodiments, the surgical instrument 500 forms at least a portion of a cutting blade and/or cutting device. In some embodiments, the surgical instrument 500 forms at least a portion of a sagittal blade and/or sagittal saw, among other cutting blades and/or cutting devices that are possible and contemplated herein.

At least in the embodiments illustrated in FIGS. 5A through 5C, the surgical instrument 500 includes, among other features, a body 402, a distal end 408, a proximal end 410, a set of cutting teeth 414, an attachment mechanism 416, and a cutting tip 420 similar to the body 402, distal end 408, proximal end 410, set of cutting teeth 414, attachment mechanism 416, and cutting tip 420 of the various embodiments of the surgical instrument 400 discussed herein with reference to FIGS. 4A through 4J. A surgical instrument 500 further includes, among other features and/or elements, a first surface 404 and a second surface 506 (see, e.g., FIG. 5A).

The first surface 404, in various embodiments, includes a set of cutting burrs 412 similar to any of the embodiments of a first surface 404 (e.g., first surfaces 404A through 404G) and/or embodiments of the cutting burr(s) 412 discussed with reference to FIGS. 4A through 4J. That is, the first surface 404 in the surgical instrument 500 may include any quantity of cutting burrs 412 arranged and/or positioned on the first surface 404 in any pre-set non-pattern configuration, random pattern, or patterned configuration similar to the various embodiments of the surgical instrument 400 discussed with reference to FIGS. 4A through 4J (see, e.g., cutting burrs 412 positioned and/or arranged on the first surfaces 404A through 404G). In some embodiments, the first surface 404 may include a set of cutting burrs 412 positioned and/or arranged on the first surface 404 in one or more rows 422 of cutting burrs 412 and/or one or more columns 424 of cutting burrs 412 similar to the various embodiments of the row(s) 422A of cutting burrs 412A and/or the column(s) 424A of cutting burrs 412A positioned and/or arranged on the first surface 404G (see. e.g., FIG. 4I).

In various embodiments, the second surface 506 includes a set of cutting blades 512 positioned thereon. As illustrated in at least FIGS. 5B and 5C, the set of cutting blades 512 are spaced apart and positioned vertically and/or at an angle with respect to the second surface 506 to form a set of columns 524 of cutting blades 512.

A cutting blade 512 may include any suitable structure, surface, and/or edge that is capable of cutting and/or performing an osteotomy. In some embodiments, a cutting blade 512 includes a single edge and/or a single smooth edge, among other blades and/or edges that are possible and contemplated herein.

A set of cutting blades 512 may include any suitable quantity of cutting blades 512 and/or quantity of columns 524 of cutting blades 512 that can facilitate and/or assist the surgical instrument 500 in performing an osteotomy (e.g., a wedge-shaped osteotomy, a straight-cut osteotomy, and/or a parallel-cut osteotomy). In various embodiments, the second surface 506 includes a suitable quantity of cutting blades 512 so that the surgical instrument 500 can perform an osteotomy in one cut and/or one pass.

In various embodiments, the second surface 506 includes a quantity of cutting blades 512 in the range of about 2 cutting blades 512 to about 40 cutting blades 512, among other ranges of quantities of cutting blades 512 and/or quantities of cutting blades 512 that are possible and contemplated herein. In some embodiments, the second surface 506 includes 9 cutting blades 512 (see, e.g., FIG. 5B), among other quantities of cutting blades 512 greater than or less than 9 cutting blades 512 that are possible and contemplated herein. In FIG. 5B, one or more blades 512 (e.g., 4 cutting blades 512) is/are oriented outward toward the right (e.g., is/are not perpendicular to the second surface 506), one or more blades 512 (e.g., 4 cutting blades 512) are oriented outward toward the left and/or away from the blade(s) 512 oriented outwardly toward the right (e.g., is/are not perpendicular to the second surface 506), and one or more blades 512 (e.g., a cutting blade 512) is/are oriented perpendicular to the second surface 506, among other quantities, relative quantities, and/or orientation(s) of cutting blades 512 that are possible and contemplated herein.

In other embodiments, the second surface 506 includes 14 cutting blades 512 (see, e.g., FIG. 5C), among other quantities of cutting blades 512 greater than or less than 14 cutting blades 512 that are possible and contemplated herein. In FIG. 5C, one or more blades 512 (e.g., 7 cutting blades 512) is/are oriented outwardly toward the right (e.g., is not perpendicular to the second surface 506) and one or more blades 512 (e.g., 7 cutting blades 512) is/are oriented outwardly toward the left and/or away from the blade(s) 512 oriented outwardly toward the right, among other quantities, relative quantities, and/or orientation(s) of cutting blades 512 that are possible and contemplated herein.

While the surgical instruments 500 shown in FIGS. 5B and 5C including 9 cutting blades 512 and 14 cutting blades 512, respectively, the various embodiments of the surgical instrument 500 are not limited to 9 cutting blades 512 and 14 cutting blades 512. That is, various other embodiments of a surgical instrument 500 can include a different quantity of cutting blades 512 such that the second surface 506 can include any suitable quantity of cutting blades 512 less than 9 cutting blades 512, between 9 and 14 cutting blades 512, and greater than 14 cutting blades 512.

In some embodiments, the cutting blades 512 may be included on the entirety or substantially the entirety of the second surface 506. In other embodiments, the cutting blades 512 may be included on at least a portion of the second surface 506. That is, the cutting blades 512 may extend at least partially from the distal end 408 to the proximal end 410.

The portion of the second surface 506 including the cutting blades 512 may include any suitable sized portion that can produce a wedge-shaped osteotomy, a straight-cut osteotomy, and/or a parallel-cut osteotomy. Various embodiments of the surgical instrument 500 may include varying sized portions of the second surface 506 including the cutting blades 512 so that different sized and/or shaped osteotomies can be obtained. That is, different embodiments may include cutting blades 512 with differing lengths to produce different sized and/or shaped osteotomies.

A cutting blade 512 may include any suitable shape that can facilitate and/or assist the surgical instrument 500 in performing an osteotomy (e.g., a wedge-shaped osteotomy, a straight-cut osteotomy, and/or a parallel-cut osteotomy). In various embodiments, a cutting blade 512 can include a curved blade (e.g., a vertically curved blade), a straight blade, a smooth edge blade, a single edge blade, a waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 512 can include a straight cutting edge, smooth cutting edge, and/or a serrated cutting edge, among other cutting edges that are possible and contemplated herein.

In some embodiments, all of the cutting blades 512 in the set of cutting blades 512 on the second surface 506 include the same or substantially the same shape. In alternative embodiments, at least two cutting blades 512 in the set of cutting blades 512 on the second surface 506 include different shapes or substantially different shapes. In one non-limiting example, at least one cutting blade 512 includes a straight blade and at least one cutting blade 512 includes a curved blade (or other non-straight blade), among other shapes and/or combinations of shapes that are possible and contemplated herein. In an additional or alternative non-limiting example, the straight blade(s) and/or the curved blade(s) include a serrated cutting edge.

A cutting blade 512 may include any suitable height that can facilitate and/or assist the surgical instrument 500 in performing an osteotomy (e.g., a wedge-shaped osteotomy, a straight-cut osteotomy, and/or a parallel-cut osteotomy). In various embodiments, the cutting blades 512 can include a height in the range of about 0.1 mm to about 30 mm, among other suitable heights that can facilitate cutting bone that are possible and contemplated herein. In some embodiments, the cutting blades 512 include a height of 0.75 mm.

In some embodiments, all of the cutting blades 512 in the set of cutting blades 512 on the second surface 506 include a uniform height. In certain embodiments, the second surface 506 includes a slope 418B and/or is sloped similar to one or more embodiments of the second surface 406 of the surgical instrument 400 (see, e.g., FIGS. 4E through 4H) and the cutting blades 512 on the second surface 506 include a uniform height to create one or more columns 524 of cutting blades 512 that effectively upwardly increase in height from the distal end 408 to the proximal end 410.

In alternative embodiments, the second surface 506 is flat with respect to the reference plane 425 or is not sloped similar to one or more embodiments of the surgical instrument 400 and one or more of the cutting blades 512 on the second surface 506 include a height that gradually increases from the distal end 408 to the proximal end 410 such that the cutting blade(s) 512 upwardly increase in height from the distal end 408 to the proximal end 410.

Figure 6A:
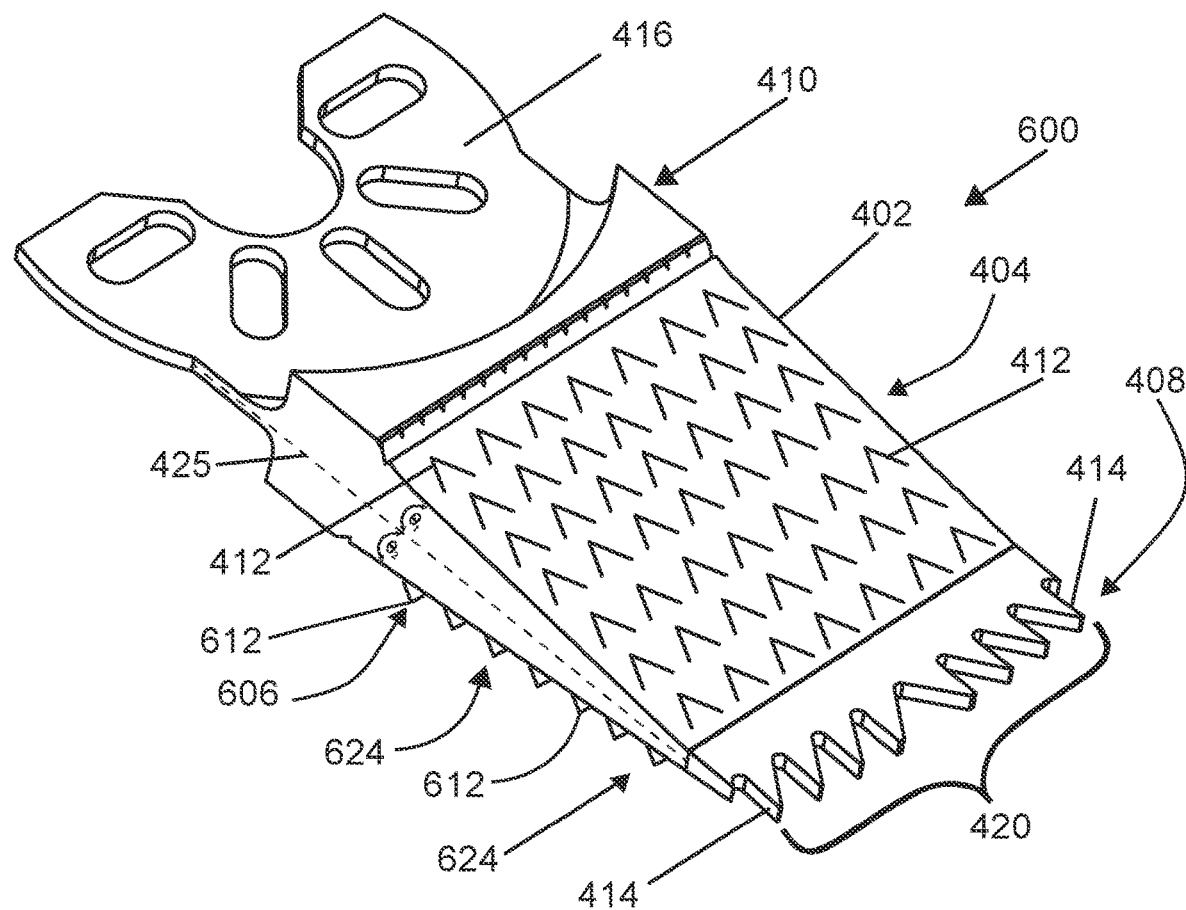
FIGS. 6A through 6C are schematic diagrams illustrating various embodiments of a double-sided surgical instrument including cutting burrs and rows of cutting blades.
Figure 6B:
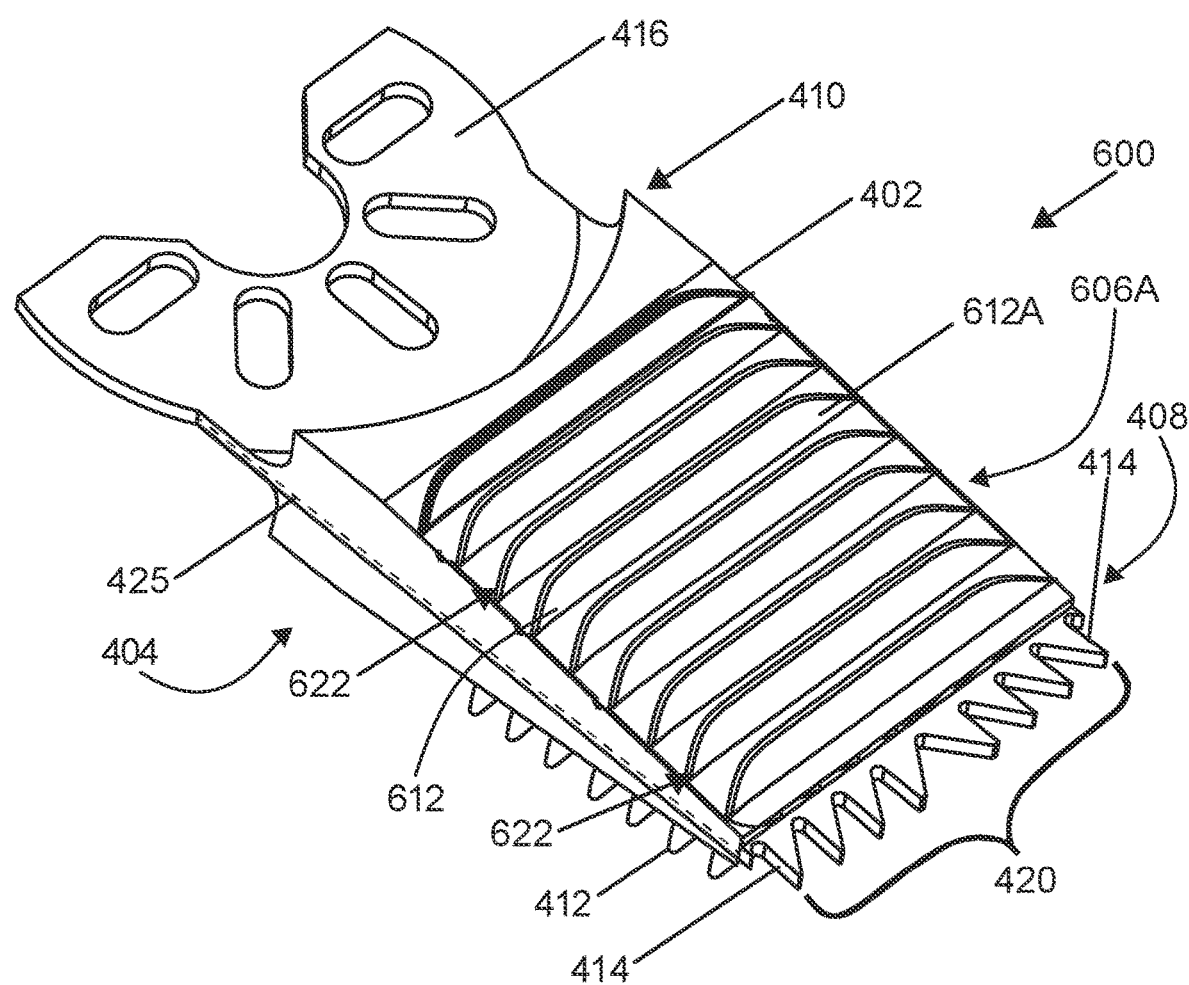
Figure 6C:
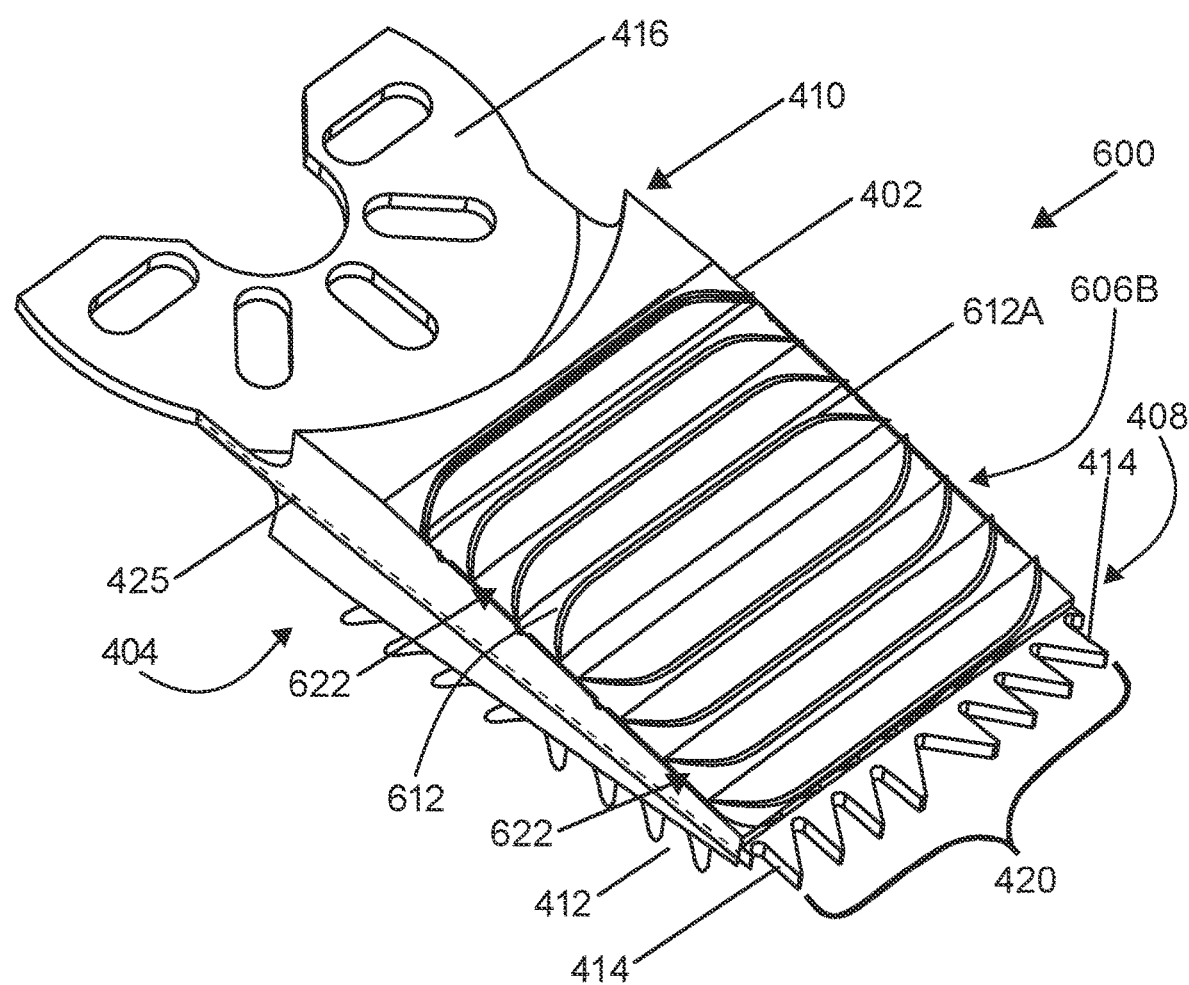

FIGS. 6A through 6C are diagrams illustrating embodiments of a surgical instrument 600. At least in the illustrated embodiment, the surgical instrument 600 includes a double-sided device for cutting bone and/or tissue (e.g., a cutting device) and/or a multi-sided (e.g., two or more sided) a cutting device. While the description below refers to the surgical instrument 600 as a double-sided cutting device, the below description(s) apply equally to the various embodiments of the surgical instrument 500 that include(s) more than two sides (e.g., three (3) or more sided cutting devices).

A surgical instrument 600 may be constructed of any suitable material that can cut bone. In various embodiments, the surgical instrument 600 is constructed of a sterilized suitable material that can cut bone. In some embodiments, the surgical instrument 600 includes stainless steel, carbon steel, aluminum, and titanium, among other suitable materials and combinations of materials that are possible and contemplated herein. In additional or alternative embodiments, the surgical instrument 600 includes surgical grade stainless steel, among other suitable surgical grade materials and combinations of materials that are possible and contemplated herein.

In various embodiments, the surgical instrument 600 forms at least a portion of a cutting blade and/or cutting device. In some embodiments, the surgical instrument 600 forms at least a portion of a sagittal blade and/or sagittal saw, among other cutting blades and/or cutting devices that are possible and contemplated herein.

At least in the embodiments illustrated in FIGS. 6A through 6C, the surgical instrument 600 includes, among other features, a body 402, a distal end 408, a proximal end 410, a set of cutting teeth 414, an attachment mechanism 416, and a cutting tip 420 similar to the body 402, distal end 408, proximal end 410, set of cutting teeth 414, attachment mechanism 416, and cutting tip 420 of the various embodiments of the surgical instrument 400 discussed herein with reference to FIGS. 4A through 4J. A surgical instrument 600 further includes, among other features and/or elements, a first surface 404 and a second surface 606 (see, e.g., FIG. 6A).

The first surface 404, in various embodiments, includes a set of cutting burrs 412 similar to any of the embodiments of a first surface 404 (e.g., first surfaces 404A through 404G) and/or embodiments of the cutting burr(s) 412 discussed with reference to FIGS. 4A through 4J. That is, the first surface 404 in the surgical instrument 600 may include any quantity of cutting burrs 412 arranged and/or positioned on the first surface 404 in any pre-set non-pattern configuration, random pattern, or patterned configuration similar to the various embodiments of the surgical instrument 400 discussed with reference to FIGS. 4A through 4J (see, e.g., cutting burrs 412 positioned and/or arranged on the first surfaces 404A through 404G). In some embodiments, the first surface 404 may include a set of cutting burrs 412 positioned and/or arranged on the first surface 404 in one or more rows 422 of cutting burrs 412 and/or one or more columns 424 of cutting burrs 412 similar to the various embodiments of the row(s) 422A of cutting burrs 412A and/or the column(s) 424A of cutting burrs 412A positioned and/or arranged on the first surface 404G (see. e.g., FIG. 4I).

In various embodiments, the second surface 606 includes a set of cutting blades 612 positioned thereon. As illustrated in at least FIGS. 6B and 6C, the set of cutting blades 612 are spaced apart and positioned vertically and/or at an angle with respect to the second surface 606 to form a set of rows 622 of cutting blades 612.

The cutting blade 612 may include any suitable structure, surface, and/or edge that is capable of cutting and/or performing an osteotomy. In some embodiments, the cutting blade 612 includes a single edge and/or a single smooth edge, among other blades and/or edges that are possible and contemplated herein.

A set of cutting blades 612 may include any suitable quantity of cutting blades 612 and/or quantity of rows 622 of cutting blades 612 that can facilitate and/or assist the surgical instrument 600 in performing an osteotomy (e.g., a wedge-shaped osteotomy, a straight-cut osteotomy, and/or a parallel-cut osteotomy). In various embodiments, the second surface 606 includes a suitable quantity of cutting blades 612 so that the surgical instrument 600 can perform an osteotomy in one cut and/or one pass.

In various embodiments, the second surface 606 includes a quantity of cutting blades 612 in the range of about 2 cutting blades 612 to about 40 cutting blades 612, among other ranges of quantities of cutting blades 612 and/or quantities of cutting blades 612 that are possible and contemplated herein. In some embodiments, the second surface 606 includes 9 cutting blades 612 (see, e.g., FIG. 6B), among other quantities of cutting blades 612 greater than or less than 9 cutting blades 612 that are possible and contemplated herein. In FIG. 6B, the cutting blades 612 are oriented perpendicular to the second surface 606, among other quantities and/or orientation(s) of cutting blades 612 that are possible and contemplated herein.

In other embodiments, the second surface 606 includes 8 cutting blades 612 (see, e.g., FIG. 6C), among other quantities of cutting blades 612 greater than or less than 8 cutting blades 612 that are possible and contemplated herein. In FIG. 6C, one or more blades 612 (e.g., 4 cutting blades 612) is/are oriented outwardly toward the distal end 408 (e.g., is not perpendicular to the second surface 606) and one or more blades 612 (e.g., 4 cutting blades 612) is/are oriented outwardly to the proximal end 410 (e.g., is not perpendicular to the second surface 606), among other quantities, relative quantities, and/or orientation(s) of cutting blades 612 that are possible and contemplated herein.

While the surgical instruments 600 shown in FIGS. 6B and 6C including 9 cutting blades 612 and 8 cutting blades 612, respectively, the various embodiments of the surgical instrument 600 are not limited to 9 cutting blades 612 and 8 cutting blades 612. That is, various other embodiments of a surgical instrument 600 can include a different quantity of cutting blades 612 such that the second surface 606 can include any suitable quantity of cutting blades 612 less than 8 cutting blades 612 and greater than 9 cutting blades 612.

In some embodiments, the cutting blades 612 may be included on the entirety or substantially the entirety of the second surface 606. In other embodiments, the cutting blades 612 may be included on at least a portion of the second surface 606. That is, the rows 624 of cutting blades 612 may extend at least partially from the distal end 608 to the proximal end 610.

The portion of the second surface 606 including the cutting blades 612 may include any suitable sized portion that can produce a wedge-shaped osteotomy, a straight-cut osteotomy, and/or a parallel-cut osteotomy. Various embodiments of the surgical instrument 600 may include varying sized portions of the second surface 606 including the cutting blades 612 so that different sized and/or shaped osteotomies can be obtained. That is, different embodiments may include cutting blades 612 with differing lengths to produce different sized and/or shaped osteotomies.

The cutting blade 612 may include any suitable shape that can facilitate and/or assist the surgical instrument 600 in performing an osteotomy (e.g., a wedge-shaped osteotomy, a straight-cut osteotomy, and/or a parallel-cut osteotomy). In various embodiments, the cutting blade 612 can include a curved blade (e.g., a vertically curved blade), a straight blade, a smooth edge blade, a single edge blade, a waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 612 can include a straight cutting edge, smooth cutting edge, and/or a serrated cutting edge, among other cutting edges that are possible and contemplated herein.

In some embodiments, all of the cutting blades 612 in the set of cutting blades 612 on the second surface 606 include the same or substantially the same shape. In alternative embodiments, at least two cutting blades 612 in the set of cutting blades 612 on the second surface 606 include different shapes or substantially different shapes. In one non-limiting example, at least one cutting blade 612 includes a straight blade and at least one cutting blade 612 includes a curved blade (or other non-straight blade), among other shapes and/or combinations of shapes that are possible and contemplated herein. In an additional or alternative non-limiting example, the straight blade(s) and/or the curved blade(s) include a serrated cutting edge.

A cutting blade 612 may include any suitable height that can facilitate and/or assist the surgical instrument 600 in performing an osteotomy (e.g., a wedge-shaped osteotomy). In various embodiments, the cutting blades 612 can include a height in the range of about 0.1 mm to about 30 mm, among other suitable heights that can facilitate cutting bone that are possible and contemplated herein. In some embodiments, the cutting blades 612 include a height of 0.75 mm.

In some embodiments, all of the cutting blades 612 in the set of cutting blades 612 on the second surface 606 include a uniform height. In certain embodiments, the second surface 606 includes a slope 418B and/or is sloped similar to one or more embodiments of the second surface 406 of the surgical instrument 400 (see, e.g., FIGS. 4E through 4H) and the cutting blades 612 on the second surface 606 include a uniform height to create one or more rows 622 of cutting blades 612 that effectively upwardly increase in height from the distal end 408 to the proximal end 410.

In alternative embodiments, the second surface 606 is flat with respect to the reference plane 425 or is not sloped similar to one or more embodiments of the surgical instrument 400 and the rows 622 of cutting blades 612 on the second surface 606 include a height that gradually increases from the distal end 408 to the proximal end 410 such that the rows 622 of cutting blade(s) 612 upwardly increase in height from the distal end 408 to the proximal end 410.

In various embodiments, the surgical instruments 400 through 600 each form at least a portion of a cutting blade and/or cutting device. In some embodiments, the surgical instruments 400 through 600 form at least a portion of a sagittal blade and/or sagittal saw, among other cutting blades and/or cutting devices that are possible and contemplated herein.

In various embodiments, the surgical instruments 400 through 600 can each be utilized to perform an osteotomy, which can include any suitable osteotomy that is known or developed in the future. In some embodiments, the osteotomy performed by the surgical instruments 400 through 600 includes cutting and/or preparing a single bone (e.g., a cuneiform, a metatarsal, calcaneus, metacarpal, humerus, and femur, etc.).

In additional or alternative embodiments, the surgical instruments 400 through 600 can each be utilized to perform two or more osteotomies. In certain embodiments, the surgical instruments 400 through 600 can each be utilized to simultaneously perform two or more osteotomies, which can include cutting two different bones at the same time (e.g., a cuneiform and a metatarsal, carpal and metacarpal, and humerus and scapula, etc.).

In one non-limiting example, a first bone may be cut/prepared with one side of a surgical instrument 400 through 600 and a second bone may be cut/prepared with another or different side of the surgical instrument 400 through 600. Here, the first and second bones may be cut/prepared in series (e.g., one at a time), cut/prepared in parallel (e.g., at the same time or simultaneously), and/or cut/prepared substantially in parallel and/or series.

In another non-limiting example, a first portion of a bone may be cut/prepared with one side of the surgical instrument 400 through 600 and a second or different portion of the same bone may be cut/prepared with another or different side of the surgical instrument 400 through 600. Here, the first and second bones may be cut/prepared in series (e.g., one at a time), cut/prepared in parallel (e.g., at the same time or simultaneously), and/or cut/prepared substantially in parallel and/or series.

In still another non-limiting example, a first bone and a second bone may be cut/prepared with the same side of the surgical instrument 400 through 600. Here, the first and second bones may be cut/prepared in series (e.g., one at a time), cut/prepared in parallel (e.g., at the same time or simultaneously), and/or cut/prepared substantially in parallel and/or series.

In yet another non-limiting example, a first portion and a second portion of the same bone may be cut/prepared with the same side of the surgical instrument 400 through 600. Here, the first and second bones may be cut/prepared in series (e.g., one at a time), cut/prepared in parallel (e.g., at the same time or simultaneously), and/or cut/prepared substantially in parallel and/or series.

In a further non-limiting example, the same portion of the same bone may be cut with different sides of the surgical instrument 400 through 600. Here, the first and second bones may be cut/prepared in series (e.g., one at a time), cut/prepared in parallel (e.g., at the same time or simultaneously), and/or cut/prepared substantially in parallel and/or substantially in series.

In various embodiments, at least one of the two or more osteotomies capable of being performed by a surgical instrument 400 through 600 includes a wedge-shaped osteotomy and at least one of the two or more osteotomies includes a straight-cut osteotomy or a parallel-cut osteotomy, among other types of osteotomies and/or combinations of osteotomies that are possible and contemplated herein. In other embodiments, at least one of the two or more osteotomies capable of being performed by the surgical instrument 400 through 600 includes a straight-cut osteotomy and at least one of the two or more osteotomies includes a wedge-cut osteotomy or a parallel-cut osteotomy, among other types of osteotomies and/or combinations of osteotomies that are possible and contemplated herein. In still other embodiments, at least one of the two or more osteotomies capable of being performed by the surgical instrument 400 through 1000 includes a parallel-cut osteotomy and at least one of the two or more osteotomies includes a wedge-cut osteotomy or a straight-cut osteotomy, among other types of osteotomies and/or combinations of osteotomies that are possible and contemplated herein.

In some embodiments, a surgical instrument 400 through 600 (e.g., via first surface and second surface) can perform and/or facilitate performance of a relatively large or larger wedge-shaped osteotomy between two bones (e.g., at a joint) and/or the first surface can perform and/or facilitate performance of a relatively small or smaller wedge-shaped osteotomy on a first bone and the second surface can perform and/or facilitate performance of another relatively small or smaller wedge-shaped osteotomy on a second bone, which can include the same size or a different size wedge-shaped osteotomy than the first surface. In other embodiments, the surgical instrument 400 through 600 (e.g., via first surface and second surface) can perform and/or facilitate performance of a relatively large or larger straight-cut osteotomy between two bones (e.g., at a joint) and/or the first surface can perform and/or facilitate performance of a relatively small or smaller straight-cut osteotomy on a first bone and the second surface can perform and/or facilitate performance of another relatively small or smaller straight-cut osteotomy on a second bone, which can include the same size or a different size straight-cut osteotomy than the first surface. In other embodiments, the surgical instrument 400 through 600 (e.g., via first surface and second surface) can perform and/or facilitate performance of a relatively large or larger parallel-cut osteotomy between two bones (e.g., at a joint) and/or the first surface can perform and/or facilitate performance of a relatively small or smaller parallel-cut osteotomy on a first bone and the second surface can perform and/or facilitate performance of another relatively small or smaller parallel-cut osteotomy on a second bone, which can include the same size or a different size parallel-cut osteotomy than the first surface.

Figure 7:
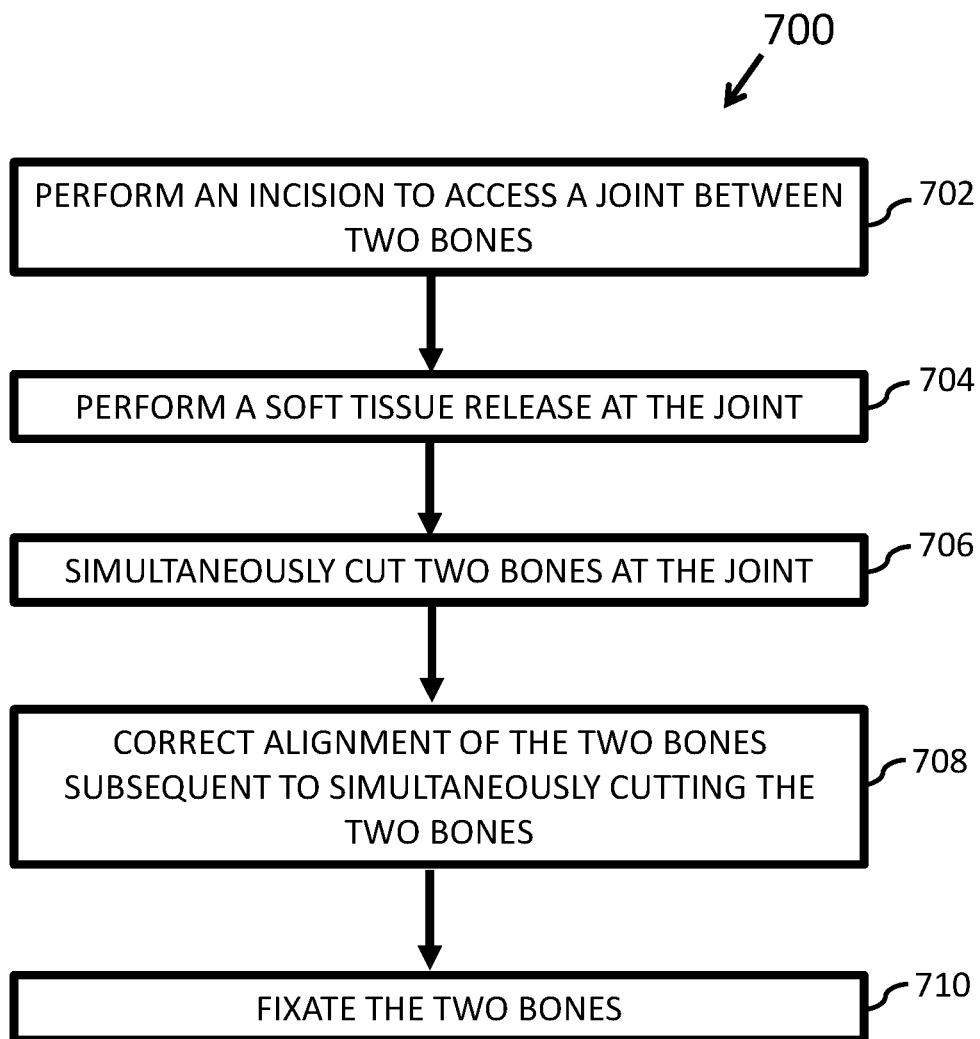
FIGS. 7 through 10 are schematic flow diagrams of various embodiments of a method for aligning two bones connected at a joint.

FIG. 7 is a schematic flow chart diagram illustrating one embodiment of a method 700 for aligning two bones connected at a joint. The two bones may be any two bones separated by any joint (e.g., in a human or animal).

At least in the illustrated embodiment, the method 700 begins by performing an incision in a patient to open and/or access a target joint (block 702). The target joint may include any suitable joint between any two bones. Further, the incision may be performed at any suitable location at the target joint and/or bone(s) that can enable access the target joint.

A soft tissue release is performed at the joint (block 704). The soft tissue release may include any suitable technique and/or procedure that can release the target joint and/or one or both of the bones at the target joint.

Two bones at the target joint are simultaneously cut and/or prepared (block 706). The two bones may be simultaneously cut using a double-sided surgical instrument. In some embodiments, simultaneously cutting the two bones at the target joint with the double-sided surgical instrument includes simultaneously cutting the two bones at the target joint with one or more embodiments of a surgical instrument 400. In other embodiments, simultaneously cutting the two bones at the target joint with the double-sided surgical instrument includes simultaneously cutting the two bones at the target joint with one or more embodiments of a surgical instrument 500. In still other embodiments, simultaneously cutting the two bones at the target joint with the double-sided surgical instrument includes simultaneously cutting the two bones at the target joint with one or more embodiments of a surgical instrument 600.

The alignment of the two bones is corrected subsequent to simultaneously cutting the two bones at the target joint (block 708). Correcting the alignment of the two bones includes, in various embodiments, correcting the alignment of the two bones in one plane, two planes, or three planes, which can include a transverse plane, a sagittal plane, and/or a frontal plane.

After correction of the alignment, the two bones are fixated (block 710). The bones may be fixated using any fixation technique(s) and/or fixation device(s) that is/are known or developed in the future. In various embodiments, the two bones are fixated using a fixation device manufactured by Fusion Orthopedics, LLC of Mesa, Arizona.

Figure 8:
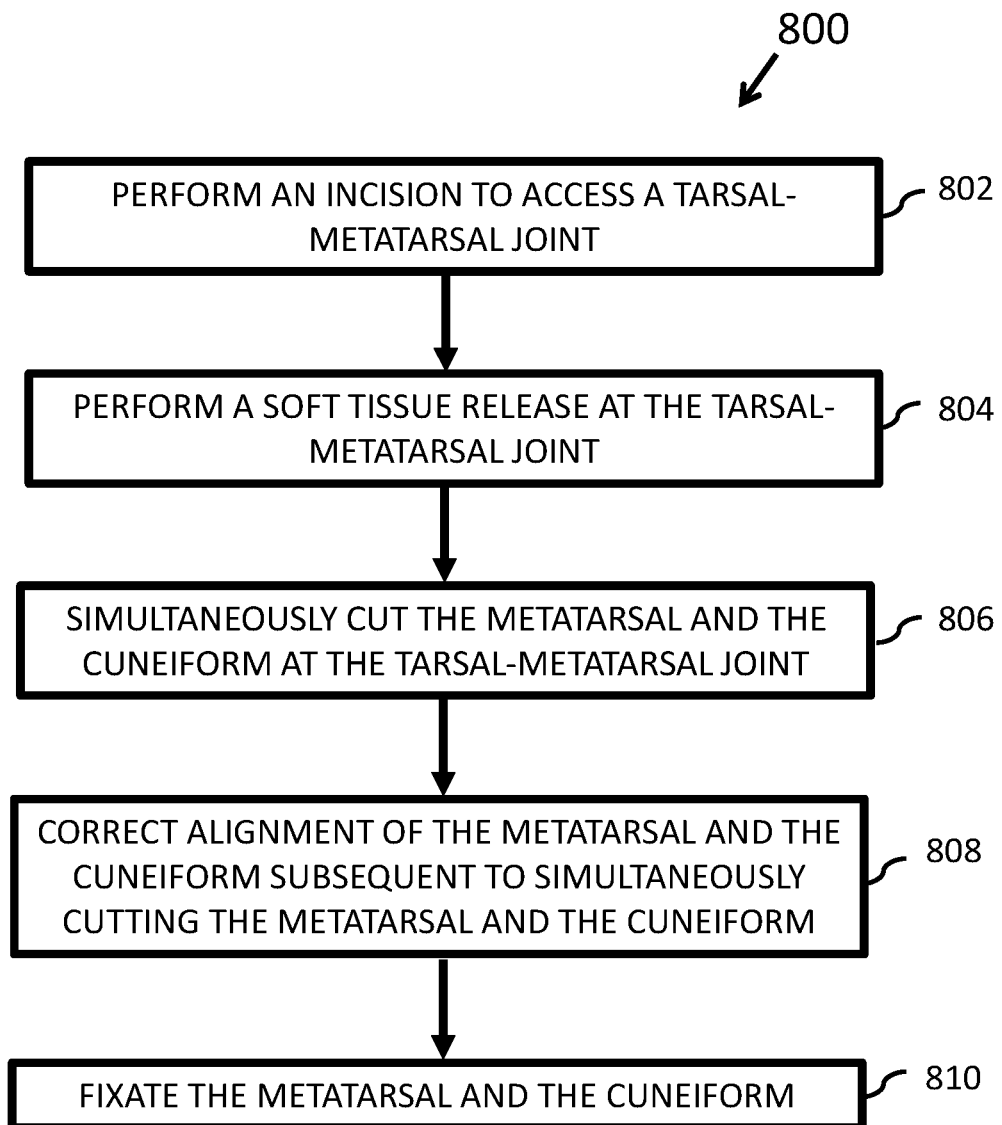

FIG. 8 is a schematic flow chart diagram illustrating another embodiment of a method 800 for aligning two bones connected at a joint. In various embodiments, the joint includes a tarsal-metatarsal joint and the two bones include a metatarsal and a cuneiform. In certain embodiments, the metatarsal includes the first metatarsal and cuneiform. Further, the method 800 may be utilized to correct a bunion. That is, the method 800 can include a bunionectomy.

At least in the illustrated embodiment, the method 800 begins by performing an incision in a patient to open and/or access a tarsal-metatarsal joint (block 802). The incision may be performed at any suitable location on and/or at the tarsal-metatarsal joint, metatarsal, and/or cuneiform. In various embodiments, the incision can be performed on the top and/or side of the metatarsal (e.g., the first metatarsal).

A soft tissue release is performed at the tarsal-metatarsal joint (block 804). The soft tissue release may include any suitable technique and/or procedure that can release soft tissue at the tarsal-metatarsal joint. In some embodiments, the soft tissue release includes a lateral release of soft tissue.

The metatarsal and cuneiform at the tarsal-metatarsal joint are simultaneously cut and/or prepared (block 806). The metatarsal and the cuneiform may be simultaneously cut using a double-sided surgical instrument. In some embodiments, simultaneously cutting the metatarsal and the cuneiform with the double-sided surgical instrument includes simultaneously cutting the metatarsal and the cuneiform with one or more embodiments of a surgical instrument 400. In other embodiments, simultaneously cutting the metatarsal and the cuneiform with the double-sided surgical instrument includes simultaneously cutting the metatarsal and the cuneiform with one or more embodiments of a surgical instrument 500. In still other embodiments, simultaneously cutting the metatarsal and the cuneiform with the double-sided surgical instrument includes simultaneously cutting the metatarsal and the cuneiform with one or more embodiments of a surgical instrument 600.

The alignment of the metatarsal and the cuneiform is corrected subsequent to simultaneously cutting the metatarsal and the cuneiform (block 808). Correcting the alignment of the metatarsal and the cuneiform includes, in various embodiments, correcting the alignment of the metatarsal and the cuneiform in one plane, two planes, or three planes, which can include a transverse plane, a sagittal plane, and/or a frontal plane.

After correction of the alignment, the metatarsal and the cuneiform are fixated to one another (block 810). The metatarsal and the cuneiform may be fixated using any fixation technique(s) and/or fixation device(s) that is/are known or developed in the future. In various embodiments, the metatarsal and the cuneiform are fixated using a fixation device manufactured by Fusion Orthopedics, LLC of Mesa, Arizona.

Figure 9:
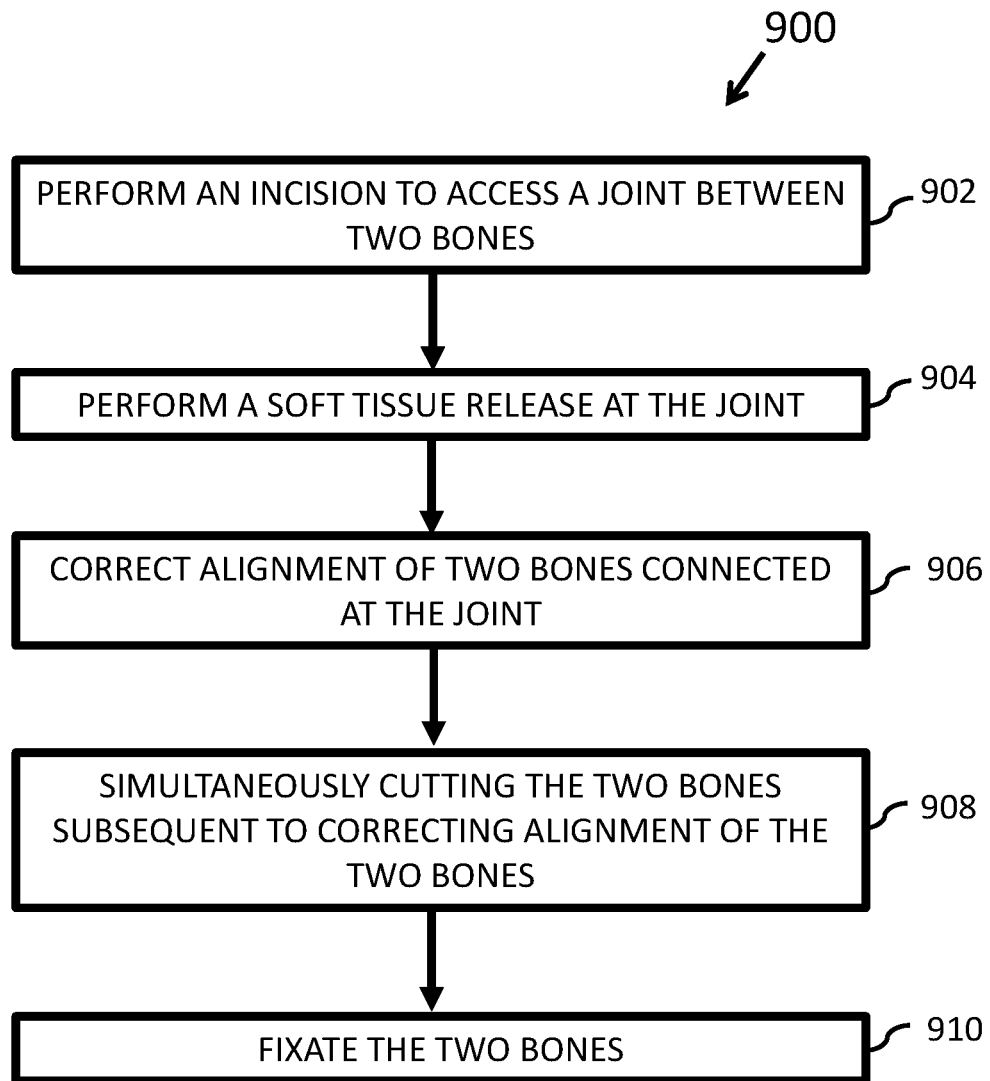

FIG. 9 is a schematic flow chart diagram illustrating yet another embodiment of a method 900 for aligning two bones connected at a joint. The two bones may be any two bones separated by any joint (e.g., in a human or animal).

At least in the illustrated embodiment, the method 900 begins by performing an incision in a patient to open and/or access a target joint (block 902). The target joint may include any suitable joint between any two bones. Further, the incision may be performed at any suitable location at the target joint and/or bone(s) that can enable access the target joint.

A soft tissue release is performed at the joint (block 904). The soft tissue release may include any suitable technique and/or procedure that can release the target joint and/or one or both of the bones at the target joint.

The alignment of two bones at the target joint is corrected (block 906). Correcting the alignment of the two bones includes, in various embodiments, correcting the alignment of the two bones in one plane, two planes, or three planes, which can include a transverse plane, a sagittal plane, and/or a frontal plane.

Subsequent to correcting the alignment, the two bones are simultaneously cut and/or prepared (block 908). The two bones may be simultaneously cut using a double-sided surgical instrument. In some embodiments, simultaneously cutting the two bones at the target joint with the double-sided surgical instrument includes simultaneously cutting the two bones at the target joint with one or more embodiments of a surgical instrument 400. In other embodiments, simultaneously cutting the two bones at the target joint with the double-sided surgical instrument includes simultaneously cutting the two bones at the target joint with one or more embodiments of a surgical instrument 500. In still other embodiments, simultaneously cutting the two bones at the target joint with the double-sided surgical instrument includes simultaneously cutting the two bones at the target joint with one or more embodiments of a surgical instrument 600.

After simultaneously cutting the two bones, the two bones are fixated (block 910). The bones may be fixated using any fixation technique(s) and/or fixation device(s) that is/are known or developed in the future. In various embodiments, the two bones are fixated using a fixation device manufactured by Fusion Orthopedics, LLC of Mesa, Arizona.

Figure 10:
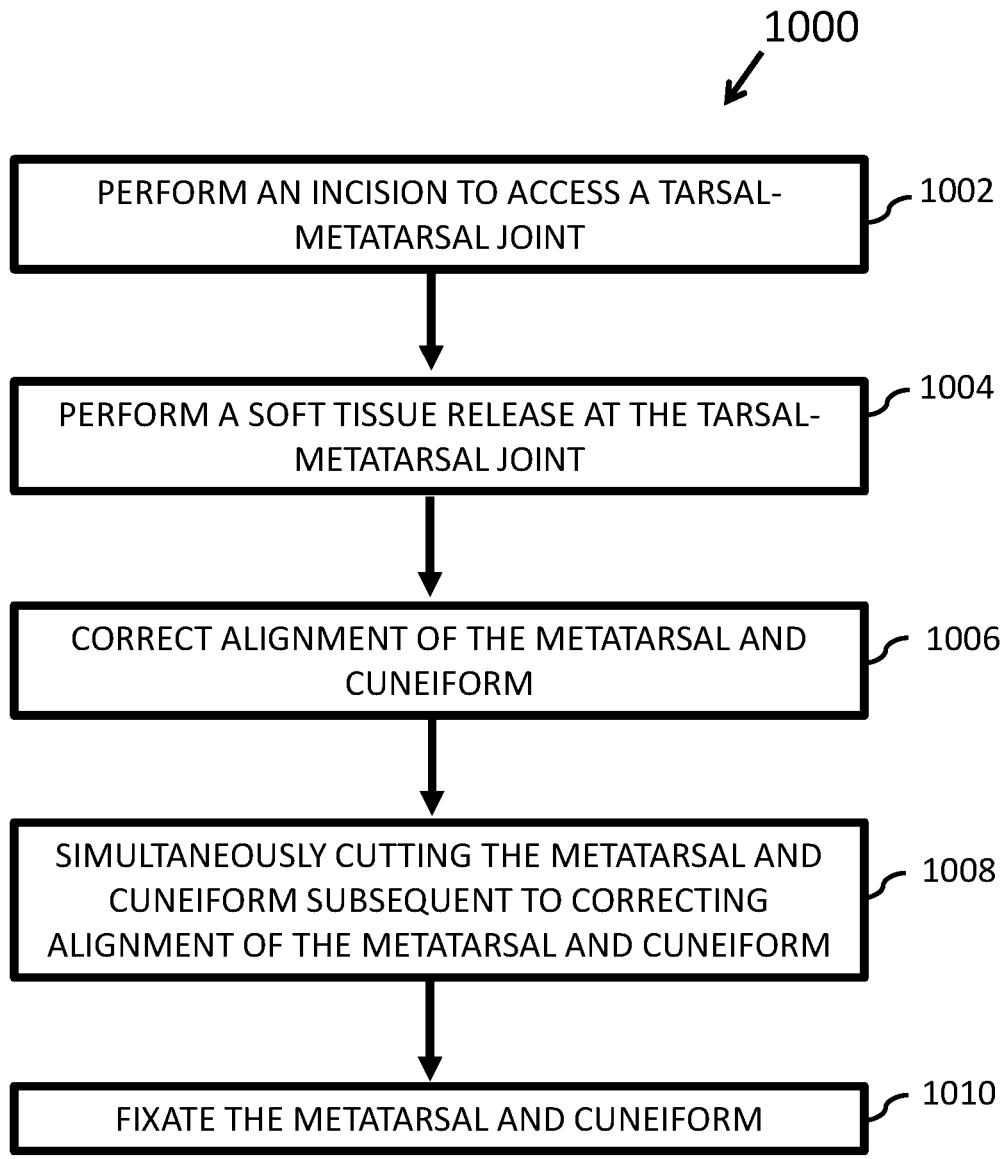

FIG. 10 is a schematic flow chart diagram illustrating still another embodiment of a method 1000 for aligning two bones connected at a joint. In various embodiments, the joint includes a tarsal-metatarsal joint and the two bones include a metatarsal and a cuneiform. In certain embodiments, the metatarsal includes the first metatarsal and cuneiform. Further, the method 1000 may be utilized to correct a bunion. That is, the method 1000 can include a bunionectomy.

At least in the illustrated embodiment, the method 1000 begins by performing an incision in a patient to open and/or access a tarsal-metatarsal joint (block 1002). The incision may be performed at any suitable location on and/or at the tarsal-metatarsal joint, metatarsal, and/or cuneiform. In various embodiments, the incision can be performed on the top and/or side of the metatarsal (e.g., the first metatarsal).

A soft tissue release is performed at the tarsal-metatarsal joint (block 1004). The soft tissue release may include any suitable technique and/or procedure that can release soft tissue at the tarsal-metatarsal joint. In some embodiments, the soft tissue release includes a lateral release of soft tissue.

The alignment of the metatarsal and the cuneiform is corrected (block 1006). Correcting the alignment of the metatarsal and the cuneiform includes, in various embodiments, correcting the alignment of the metatarsal and the cuneiform in one plane, two planes, or three planes, which can include a transverse plane, a sagittal plane, and/or a frontal plane.

Subsequent to correcting the alignment, the metatarsal and cuneiform at the tarsal-metatarsal joint are simultaneously cut and/or prepared (block 1008). The metatarsal and the cuneiform may be simultaneously cut using a double-sided surgical instrument. In some embodiments, simultaneously cutting the metatarsal and the cuneiform with the double-sided surgical instrument includes simultaneously cutting the metatarsal and the cuneiform with one or more embodiments of a surgical instrument 400. In other embodiments, simultaneously cutting the metatarsal and the cuneiform with the double-sided surgical instrument includes simultaneously cutting the metatarsal and the cuneiform with one or more embodiments of a surgical instrument 500. In still other embodiments, simultaneously cutting the metatarsal and the cuneiform with the double-sided surgical instrument includes simultaneously cutting the metatarsal and the cuneiform with one or more embodiments of a surgical instrument 600.

After simultaneously cutting the metatarsal and the cuneiform, the metatarsal and the cuneiform are fixated to one another (block 1010). The metatarsal and the cuneiform may be fixated using any fixation technique(s) and/or fixation device(s) that is/are known or developed in the future. In various embodiments, the metatarsal and the cuneiform are fixated using a fixation device manufactured by Fusion Orthopedics, LLC of Mesa, Arizona.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

The invention claimed is:

1. A surgical instrument, comprising:
    a single body comprising a distal end, a proximal end, a first non-curved surface, and a second surface;
    the single body further comprising a plurality of cutting burrs integral with the single body that are capable of cutting bone; and
    a plurality of columns of cutting blades integral with the single body that are capable of cutting bone,
    wherein:
        the plurality of burrs are positioned on one of the first surface and the second surface;
        the plurality of columns of cutting blades are positioned on one of the first surface and the second surface; and
        the plurality of burrs and the plurality of columns of cutting blades are on different surfaces.

2. The surgical instrument of claim 1, wherein:
    the plurality of cutting burrs are positioned on the first surface; and
    the plurality of columns of cutting blades are positioned on the second surface.

3. The surgical instrument of claim 2, wherein the first surface comprises a first slope greater than zero degrees relative to a reference plane, and the second surface comprises a second slope greater than zero degrees relative to the reference plane, wherein the reference plane is between the first surface and the second surface.

4. The surgical instrument of claim 1, wherein:
    the plurality of cutting burrs are positioned on the second surface; and
    the plurality of columns of cutting blades are positioned on the first surface.

5. The surgical instrument of claim 4, wherein the first surface comprises a first slope greater than zero degrees relative to a reference plane, and the second surface comprises a second slope greater than zero degrees relative to the reference plan, wherein the reference plane is between the first surface and the second surface.

6. The surgical instrument of claim 2, wherein the first surface comprises a first flat surface and the second surface comprises a second flat surface.

7. The surgical instrument of claim 2, wherein the first surface comprises a third slope greater than zero degrees relative to a reference plane, and the second surface comprises a third flat surface; and
    the first surface comprises a fourth flat surface and the second surface comprises a fourth slope greater than zero degrees relative to the reference plane, wherein the reference plane is between the first surface and the second surface.

8. The surgical instrument of claim 4, wherein the first surface comprises a first flat surface and the second surface comprises a second flat surface.

9. The surgical instrument of claim 4, wherein the first surface comprises a third slope greater than zero degrees relative to a reference plane between the first surface and the second surface, and the second surface comprises a third flat surface.

10. The surgical instrument of claim 4, wherein the first surface comprises a fourth flat surface and the second surface comprises a fourth slope greater than zero degrees relative to a reference plane between the first surface and the second surface.

11. A surgical instrument, comprising:
    a single body comprising a distal end, a proximal end, a first surface, a second surface, and a first width at the distal end;
    wherein the single body first surface and the single body second surface are opposing surfaces, and the first surface and the second surface are a separated by a distance that is substantially constant along the first width;
    the single body further comprising:
        a plurality of cutting burrs that are capable of cutting bone;
        a plurality of columns of cutting blades that are capable of cutting bone,
    wherein the plurality of burrs and the plurality of columns of cutting blades are positioned on different surfaces.

12. The surgical instrument of claim 11, wherein the first surface comprises a first slope greater than zero degrees relative to a reference plane between the first surface and the second surface, and the second surface comprises a second slope greater than zero degrees relative to the reference plane.

13. The surgical instrument of claim 11, wherein the first surface comprises a third slope equal to zero degrees relative to a reference plane between the first surface and the second surface, and the second surface comprises a fourth slope equal to zero degrees relative to the reference plane.

14. The surgical instrument of claim 11, wherein one of:
    the first surface comprises a first slope greater than zero degrees relative to a reference plane between the first surface and the second surface, and the second surface comprises a fourth slope equal to zero degrees relative to the reference plane; and
    the first surface comprises a third slope equal to zero degrees relative to the reference plane and the second surface comprises a second slope greater than zero degrees relative to the reference plane.

15. The surgical instrument of claim 11, wherein:
    the plurality of cutting burrs are positioned on the second surface; and
    the plurality of columns of cutting blades are positioned on the first surface.

16. The surgical instrument of claim 15, wherein the first surface comprises a first slope greater than zero degrees relative to a reference plane between the first surface and the second surface, and the second surface comprises a second slope greater than zero degrees relative to the reference plane.

17. The surgical instrument of claim 15, wherein the first surface comprises a third slope equal to zero degrees relative to a reference plane between the first surface and the second surface, and the second surface comprises a fourth slope equal to zero degrees relative to the reference plane.

18. The surgical instrument of claim 15, wherein one of:
- the first surface comprises a first slope greater than zero degrees relative to a reference plane between the first surface and the second surface, and the second surface comprises a fourth slope equal to zero degrees relative to the reference plane; and
- the first surface comprises a third slope equal to zero degrees relative to the reference plane and the second surface comprises a second slope greater than zero degrees relative to the reference plane.

\* \* \* \* \*